(12) United States Patent
Schwartz et al.

(10) Patent No.: US 7,138,413 B1
(45) Date of Patent: Nov. 21, 2006

(54) NON-IMIDAZOLE ALKYLAMINES AS HISTAMINE $H_3$-RECEPTOR LIGANDS AND THEIR THERAPEUTIC APPLICATIONS

(75) Inventors: Jean-Charles Schwartz, Paris (FR); Monique Garbarg, Paris (FR); Jeanne-Marie Lecounte, Paris (FR); Xavier Ligneau, Paris (FR); Walter G Schunacx, Berlin (DE); Hulger Stark, Berlin (DE); Charon Robin Ganellin, Welwyn (GB); Fabien Leurquin, London (GB); Sigurd Elz, Berlin (DE); Jean-Michel Arrang, Dourdan (FR)

(73) Assignee: Societe Civile Bioprojet, Paris (FR)

( * ) Notice: Subject to any disclaimer, the term of this patent is extended or adjusted under 35 U.S.C. 154(b) by 0 days.

(21) Appl. No.: 09/622,199

(22) PCT Filed: Jul. 29, 1999

(86) PCT No.: PCT/EP99/05744

§ 371 (c)(1),
(2), (4) Date: May 31, 2001

(87) PCT Pub. No.: WO00/06254

PCT Pub. Date: Feb. 10, 2000

(30) Foreign Application Priority Data

Jul. 29, 1998 (EP) .................................. 98401944
Dec. 31, 1998 (EP) .................................. 98403351

(51) Int. Cl.
*A61K 31/47* (2006.01)
(52) U.S. Cl. ....................... 514/312; 546/153
(58) Field of Classification Search ................ 546/153; 514/312
See application file for complete search history.

(56) References Cited

U.S. PATENT DOCUMENTS

| | | | |
|---|---|---|---|
| 2,870,151 A | 1/1959 | Wright et al. | |
| 3,312,696 A | 4/1967 | Turbanti | |
| 3,947,434 A | 3/1976 | Spencer et al. | |
| 4,751,302 A | 6/1988 | Ibuki et al. | |

OTHER PUBLICATIONS

Yamada, Chemical Abstracts 125:345266, abstract of JP 08227828, 1996.*
Fenton, CA 125:10758, abstract of Tetrahedron, vol. 52(16), pp 5913-5928, 1996.*
Psiorz, CA 116:41309, abstract of EP 450429, 1991.*
Witek, CA 99:210420, abstract of DE 2810066, 1978.*

* cited by examiner

*Primary Examiner*—D. Margaret Seaman
(74) *Attorney, Agent, or Firm*—B. Aaron Schulman; Stites & Harbison PLLC

(57) ABSTRACT

Use of a compound of formula (A), wherein: W is a residue which imparts antagonistic and/or agonistic activity at histamine $H_3$-receptors when attached to an imidazole ring in 4(5) position; $R^1$ and $R^2$ may be identical or different and represent each independently a lower alkyl or cycloalkyl, or taken together with the nitrogen atom to which they are attached, a saturated nitrogen-containing ring (i) as defined, a non-aromatic unsaturated nitrogen-containing ring (ii) as defined, a morpholino group, or a N-substituted piperazino group as defined for preparing medicaments acting as antagonists and/or agonists at the $H_3$-receptors of histamine

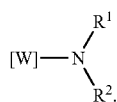

(A)

38 Claims, No Drawings

NON-IMIDAZOLE ALKYLAMINES AS HISTAMINE H₃-RECEPTOR LIGANDS AND THEIR THERAPEUTIC APPLICATIONS

The present invention relates to alkylamines of formula (A) as defined hereafter, to their preparation and to their therapeutic applications.

Antagonists of histamine H₃-receptor are known especially to increase synthesis and release of cerebral histamine. Through this mechanism, they induce an extended wakefullness, an improvement in cognitive processes, a reduction in food intake and a normalization of vestibular reflexes (Schwartz et al., Physiol. Rev., 1991, 71: 1–51).

Whence these agents are potentially useful in several central nervous system disorders such as Alzheimer disease, mood and attention alterations, cognitive deficits in psychiatric pathologies, obesity, vertigo and motion sickness.

Histamine H₃-receptor agonists are known to inhibit the release of several neurotransmitters including histamine, monoamines and neuropeptides and thereby exert sedative and sleep-promoting effects in brain. In peripheral tissues, H₃-receptor agonists exert namely anti-inflammatory, anti-nociceptive, gastro-intestinal, antisecretory smooth muscle decontracting activities.

All the H₃ receptor antagonist or agonist compounds known so far resemble histamine in possessing an imidazole ring generally monosubstituted in 4(5)-position (Ganellin et al., Ars Pharmaceutica, 1995, 36:3, 455–468; Stark et al., Drug of the Future, 1996, 21(5), 507–520).

Numerous patents and patent applications are directed to antagonist and/or agonist compounds having such structure, in particular EP 197 840, EP 494 010, WO 93/14070, WO 96/29315, WO 92/15 567, WO 93/20061, WO 93/20062, WO 95/11894, U.S. Pat. No. 5,486,526, WO 93/12107, WO 93/12108, WO 95/14007, WO 95/06037, WO 97/29092, EP 680 960, WO 96/38141, WO 96/38142, WO 96/40126.

In the litterature, Plazzi et al., Eur. J. Med. Chem. 1995, 30, 881, Clitherow et al., Bioorg. & Med. Chem. Lett. 6 (7), 833–838 (1996) Wolin et al., Bioorg. & Med. Chem. Lett; 8, 2157 (1998) can be cited also in this respect.

Nevertheless, such imidazole derivatives may show drawbacks such as poor blood-brain barrier penetration, interaction with cytochrome P-450 proteins and/or some hepatic and ocular toxicities.

Non-imidazole known neuro-active compounds such as betahistine (J-M. Arrang et al., Eur. J. Pharmacol. 1985, 111: 72–84), phencyclidine (J-M. Arrang et al., Eur. J. Pharmacol. 1988, 157: 31–35), dimaprit (J-C Schwartz et al., Agents Actions 1990, 30: 13–23), clozapine (M. Kathmann et al., Psychopharmacology 1994, 116: 464–468), and sesquiterpenes (M. Takigawa et al., JP 06 345 642 (20 Dec. 1994)) were suggested to display H₃-receptor antagonism but all these compounds have only very low potency.

These compounds were previously known as therapeutic agent before the discovery and characterization of the histamine H₃-receptor, in particular as neuro-active agents for example as neuroleptic (clozapine) or psychotomimetic (Phencyclidine) agent.

When tested at the H₃-receptor, these compounds were shown to display much lower potency than the imidazole-containing compounds described in patent applications quoted above.

Attempts at replacing the imidazole ring was generally not successful and no potent H₃-receptor ligands not containing such ring was reported in the literature up to now.

These investigations showed the importance of the 4(5)-imidazole moiety.

The objective of the invention is to provide new potent H₃-receptor ligands which may reduce the above-mentioned drawbacks.

The present invention provides new compounds, the structure of which does not contain an imidazole moiety, which are useful as histamine H₃-receptor ligands.

The compounds of the invention have the following general formula (A):

(A)

in which:

W is a residue which imparts antagonistic and/or agonistic activity at histamine H₃-receptors when attached to an imidazole ring in 4(5)-position;

R¹ and R² may be identical or different and represent each independently
a lower alkyl or cycloalkyl, or taken together with the nitrogen atom to which they are attached,
a saturated nitrogen-containing ring i) 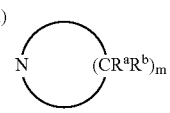

with m ranging from 2 to 8, or
a non-aromatic unsaturated nitrogen-containing ring ii) 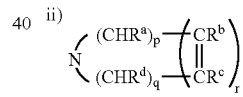

with p and q being from 0 to 3 independently and r being from 0 to 4, provided that p and q are not simulteously 0 and $2 \leq p+q+r \leq 8$, $R^{a-d}$ being independently a hydrogen atom or a lower alkyl, cycloalkyl, or carboalkoxy group, or
a morpholino group, or
a N-substituted piperazino group:

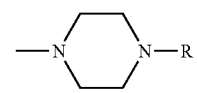

with R being a lower alkyl, cycloalkyl, carboalkoxy, aryl, arylalkyl, an alkanoyl or aroyl group.

The inventors have found, surprisingly, that antagonist and/or agonist compounds can be obtained by substituting a di(alkyl) or (cycloalkyl)amine, or a non-aromatic nitrogen-containing ring —NR¹R² as above-defined for the imidazole ring, in known antagonist and/or agonist imidazole derivatives.

It is also believed that antagonist and/or agonist activity can be foreseen, by equivalence, for compounds according to formula (A) having a W residue of imidazole derivatives which were suggested in the prior art as $H_3$ antagonists or agonists, and further for those W residues which would belong to future imidazole derivatives having substantial $H_3$ antagonist and/or agonist activity.

Moreover, the inventors have observed that such non-imidazole analogues can provide potent antagonist and/or agonist activity.

In this regards, they have prepared novel non-imidazole alkylamines analogues of formula (A) corresponding to known imidazole derivatives in particular from the above-mentioned prior art.

The invention also relates to the addition salts which the compounds form with pharmaceutically acceptable acids. The pharmaceutically acceptable salts comprise the non-toxic salt of inorganic or organic acids. Examples of these salts include the hydrochloride, the hydrobromide or the hydrogen maleate or hydrogen oxalate.

The present invention also encompasses the hydrates of the compounds, the hydrated salts of these compounds and the polymorphic crystalline structures.

When the compounds can exist in one or a number of isomeric forms according to the number of asymmetric centres in the molecule, the invention relates both to all the optical isomers and to their racemic modifications and the corresponding diastereoisomers. The separation of the diastereoisomers and/or of the optical isomers can be carried out according to methods known per se.

The present invention also encompasses all the possible tautomeric forms of the compounds, whether these tautomers occur in isolated form or in the form of mixtures.

According to the invention, lower alkyl or cycloalkyl is intended to mean a linear or branched alkyl group containing from 1 to 6 carbon atoms, or a saturated carbocycle containing 3 to 6 carbon atoms.

Typically examples of lower alkyl are methyl, ethyl, propyl, isopropyl and butyl groups.

A preferred group of compounds according to the invention comprises those with $R^1$ and $R^2$ representing independently a lower alkyl group, especially an ethyl group.

Preferred compounds are also those of formula (A) in which $R^1$ and $R^2$ taken together with the nitrogen atom to which they are attached, form a saturated nitrogen-containing ring:

i)

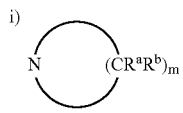

especially with m being 4, 5 or 6, optionally substituted with an alkyl group ($R^a$), preferably a methyl group.

The groups $R^a$ and $R^b$ are identical or different for each ($CR^aR^b$) moiety.

Piperidyl and pyrrolidinyl moieties are especially preferred.

Another preferred group of compounds comprises compounds (A) in which $R^1$ and $R^2$ taken together with the nitrogen atom to which they are attached, form a non-aromatic unsaturated nitrogen-containing ring:

ii)

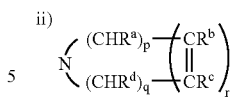

especially with p, q, and r being independently 1 or 2.

In this group, more preferred compounds are those with p being 2 and q and r each being 1.

A sub-class in this group comprises compounds with $R^{a-d}$ being each a hydrogen atom.

When $NR^1R^2$ is a nitrogen-containing ring i) or ii) as above-defined, the latter is preferably substituted with one or two lower alkyl group(s), especially a methyl group.

The position for substitution is preferably selected according the following order:

meta>para>ortho.

In this group, for nitrogen-containing ring bearing only one substituent, this latter is preferably in meta position with respect to the nitrogen-atom.

For nitrogen-containing ring bearing two substituents, meta—meta substitution is preferred, especially when these two substituents are in trans-relation.

According to the invention, piperidyl or pyrrolidinyl moiety substituted in meta or meta—meta position, especially with a methyl group, give particularly preferred compounds.

When $NR^1R^2$ represents a N-substituted piperazino group, R may be a lower alkyl e.g. methyl.

Typical examples of group R being an aryl or arylalkyl moiety are phenyl and benzyl.

R may be also an alkanoyl or aroyl group e.g. acetyl or benzoyl.

In all the possible groups for R, the alkyl moiety refers to a linear or branched chain containing from 1 to 6 carbon atoms.

The cycloalkyl group refers to a saturated carbocycle containing 3 to 7 carbon atoms.

When R represents an aryl or arylalkyl group, the aryl moiety is especially a phenyl group optionally substituted with one or more substituents selected from halogen atoms, advantageously selected from fluorine, chlorine and bromine, or a lower alkyl or cycloalkyl, a trifluoromethyl, aryl, alkoxy, aryloxy, nitro, formyl, alkanoyl, aroyl, arylalkanoyl, amino, carboxamido, cyano, alkyloximino, aryloximino, α-hydroxyalkyl, alkenyl, alkynyl, sulphamido, sulfamoyl, carboxamide, carboalkoxy, arylalkyl or oxime group.

R may be also an optionally substituted benzoyl, the substituent being as defined above with reference to the phenyl group.

Typical example of —$NR^1R^2$ representing a N-substituted piperazino group is N-acetylpiperazino.

According to one aspect, the compounds of the invention have the following general formula (I):

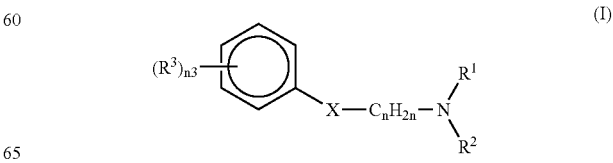

in which:

$C_nH_2n$ is a linear or branched hydrocarbon chain with n ranging from 2 to 8;

X is an oxygen or sulfur atom;

$n_3$ is an integer from 0 to 5;

$R^3$ represents each independently
  a halogen atom,
  a lower alkyl or cycloalkyl, a trifluoromethyl, aryl, alkoxy, α-alkyloxyalkyl, aryloxy, nitro, formyl, alkanoyl, aroyl, arylalkanoyl, amino, carboxamido, cyano, alkyloximino, alkylalkoximino, aryloximino, α-hydroxyalkyl, alkenyl, alkynyl, sulphamido, sulfamoyl, sulphonamido, carboxamide, carbonylcycloalkyl, alkylcarbonylalkyl, carboalkoxy, arylalkyl or oxime group,
  or taken together with the carbon atoms of the phenyl ring to which it is fused, a 5- or 6-membered saturated or unsaturated ring or a benzene ring.

$R^1$ and $R^2$ are as above-defined in formula (A).

A preferred group of compounds according to the invention is the group composed of compounds of formula (I) in which X is an oxygen atom.

Another preferred group of compounds comprises compounds (I) in which —$C_nH_{2n}$— is a linear chain —$(CH_2)_n$— with n being as previously defined.

Preferred compounds are also those with n varying from 3 to 5, and with n being more preferably 3.

A sub-class of compounds according to the invention comprises the compounds of formula (I) with $n_3$ being zero that is those having an unsubstituted phenyl moiety.

Another group of compounds according to the invention is composed of compounds containing one or more substituents $R^3$ which may be identical or different. In this group, the compounds having a mono- or di-substituted ($n_3$=1 or 2) phenyl moiety are preferred and those mono-substituted with one group $R^3$ as defined above in para-position are particularly preferred.

Among these compounds, ($n_3$ being 1) $R^3$ is preferably a halogen atom or a cyano, nitro, alkanoyl, alkyloximino or α-hydroxyalkyl group.

Still more preferred compounds are those with $R^3$ being CN, $NO_2$, $COCH_3$, $COC_2H_5$, $H_3C$—C=N—OH, $H_3C$—CH—OH and cycloalkyl-CO like cyclopropyl-CO.

$R^3$ being a halogen atom may be advantageously selected from fluorine, chlorine and bromine.

$R^3$ being an aryl group, may be especially a phenyl group.

In the other substituents $R^3$, the aryl moiety is advantageously a phenyl moiety.

$R^3$ being an aryloxy group may be especially a phenoxy group.

According to the invention, alkanoyl is intended to mean a group containing an alkyl moiety as defined above.

Typical examples of $R^3$ being an alkanoyl, aroyl or arylalkanoyl group are acetyl, butyryl and propionyl groups, benzoyl group or phenylacetyl group.

Typical examples of $R^3$ forming together with the carbon atoms of the phenyl ring to which it is fused, a saturated ring leads to 5,6,7,8-tetrahydronaphthyl or forming a benzene ring leads to a naphthyl moiety.

According to the invention, alkenyl or alkynyl group may contain advantageously from 1 to 8 carbon atoms, in particular from 1 to 6 carbon atoms and preferably 1 to 4 carbon atoms.

In carboalkoxy, carboxyamido, carbonylcycloalkyl, alkylcarbonylalkyl, or carboxamide groups, the hydrocarbon chain is saturated, linear or branched and contains an alkyl moiety as defined above.

In alkoxy, alkylalkoximino, alkyloximino, α-alkyloxyalkyl, arylalkyl or α-hydroxyalkyl group, the alkyl moiety is as previously defined also.

Particularly preferred compounds are:
1-(5-phenoxypentyl)-piperidine
1-(5-phenoxypentyl)-pyrrolidine
N-methyl-N-(5-phenoxypentyl)-ethylamine
1-(5-phenoxypentyl)-morpholine
N-(5-phenoxypentyl)-hexamethyleneimine
N-ethyl-N-(5-phenoxypentyl)-propylamine
1-(5-phenoxypentyl)-2-methyl-piperidine
1-(5-phenoxypentyl)-4-propyl-piperidine
1-(5-phenoxypentyl)-4-methyl-piperidine
1-(5-phenoxypentyl)-3-methyl-piperidine
1-acetyl-4-(5-phenoxypentyl)-piperazine
1-(5-phenoxypentyl)-3,5-trans-dimethyl-piperidine
1-(5-phenoxypentyl)-3,5-cis-dimethyl-piperidine
1-(5-phenoxypentyl)-2,6-cis-dimethyl-piperidine
4-carboethoxy-1-(5-phenoxypentyl)-piperidine
3-carboethoxy-1-(5-phenoxypentyl)-piperidine
1-[3-(4-cyclopropylcarbonylphenoxy)propyl]-piperidine
1-[3-(4-acetylphenoxy)-2-R-methylpropyl]piperidine
1-[3-(4-cyanophenoxy)propyl]-4-methylpiperidine
1-[3-(4-cyanophenoxy)propyl]-3-methylpiperidine
1-[3-(4-acetylphenoxy)-2-S-methylpropyl]piperidine
1-{3-[4-(3-oxobutyl)phenoxy]propyl}piperidine
1-[3-(4-cyano-3-fluorophenoxy)propyl]piperidine
1-[3-(4-nitrophenoxy)propyl]-3-methylpiperidine
1-[3-(4-cyanophenoxy)propyl]-2-methylpiperidine
1-[3-(4-nitrophenoxy)propyl]-2-methylpiperidine
1-[3-(4-nitrophenoxy)propyl]-4-methylpiperidine
1-[3-(4-cyanophenoxy)propyl]-2,6-dimethylpiperidine
1-[3-(4-propionylphenoxy)propyl]-3-methylpiperidine
1-[3-(4-cyclobutylcarbonylphenoxy)propyl]piperidine
1-[3-(4-cyclopentylcarbonylphenoxy)propyl]piperidine
1-[3-(4-cyanophenoxy)propyl]-cis-2-methyl-5-ethylpiperidine
1-[3-(4-cyanophenoxy)propyl]-trans-2-methyl-5-ethylpiperidine
1-[3-(4-cyanophenoxy)propyl]-cis-3,5-dimethylpiperidine
1-[3-(4-propionylphenoxy)propyl]4-methylpiperidine
1-[3-(4-propionylphenoxy)propyl]-2-methylpiperidine
1-{3-[4-(1-hydroxypropyl)phenoxy]propyl}-3-methylpiperidine
1-{3-[4-(1-hydroxypropyl)phenoxy]propyl}-4-methylpiperidine
1-[3-(4-propionylphenoxy)propyl]-2-methylpiperidine
1-[3-(4-propionylphenoxy)propyl]-4-methylpiperidine methoxime
1-[3-(4-cyanophenoxy)propyl]-trans-3,5-dimethylpiperidine
1-[3-(4-cyclopropylcarbonylphenoxy)propyl]-trans-3,5-dimethylpiperidine
1-[3-(4-cyclopropylcarbonylphenoxy)propyl]-cis-3,5-dimethylpiperidine
1-[3-(4-carbomethoxyphenoxy)propyl]piperidine
1-[3-(4-propenylphenoxy)propyl]-2-methylpiperidine
1-[3-(4-propionylphenoxy)propyl]-2-methylpiperidine
1-{3-[4-(1-ethoxypropyl)phenoxy]propyl}-2-methylpiperidine
1-[3-(4-propionylphenoxy)propyl]-4-methylpiperidine
1-[3-(4-bromophenoxy)propyl]piperidine
1-[3-(4-nitrophenoxy)propyl]piperidine
1-[3-(4-N,N-dimethylsulfonamidophenoxy)propyl]piperidine
1-[3-(4-isopropylphenoxy)propyl]piperidine
1-[3-(4-sec-butylphenoxy)propyl]piperidine 1-[3-(4-propylphenoxy)propyl]piperidine
1-[3-(4-ethylphenoxy)propyl]piperidine
1-(5-phenoxypentyl)-1,2,3,6-tetrahydropyridine
1-[5-(4-nitrophenoxy)-pentyl]-pyrrolidine
1-[5-(4-chlorophenoxy)-pentyl]-pyrrolidine
1-[5-(4-methoxyphenoxy)-pentyl]-pyrrolidine
1-[5-(4-methylphenoxy)-pentyl]-pyrrolidine
1-[5-(4-cyanophenoxy)-pentyl]-pyrrolidine
1-[5-(2-naphthyloxy)-pentyl]-pyrrolidine
1-[5-(1-naphthyloxy)-pentyl]-pyrrolidine
1-[5-(3-chlorophenoxy)-pentyl]-pyrrolidine
1-[5-(4-phenylphenoxy)-pentyl]-pyrrolidine
1-{5-[2-(5,6,7,8-tetrahydronaphthyl)-oxy]-pentyl}-pyrrolidine
1-[5-(3-phenylphenoxy)-pentyl]-pyrrolidine
1-(5-phenoxypentyl)-2,5-dihydropyrrole
1-{5-[1-(5,6,7,8-tetrahydronaphthyl)-oxy]-pentyl}-pyrrolidine
1-(4-phenoxybutyl)-pyrrolidine
1-(6-phenoxyhexyl)-pyrrolidine
1-(5-phenylthiopentyl)-pyrrolidine
1-(4-phenylthiobutyl)-pyrrolidine
1-(3-phenoxypropyl)-pyrrolidine
1-[5-(3-nitrophenoxy)-pentyl]-pyrrolidine
1-[5-(4-fluorophenoxy)-pentyl]-pyrrolidine
1-[5-(4-nitrophenoxy)-pentyl]-3-methyl-piperidine
1-[5-(4-acetylphenoxy)-pentyl]-pyrrolidine
1-[5-(4-aminophenoxy)-pentyl]-pyrrolidine
1-[5-(3-cyanophenoxy)-pentyl]-pyrrolidine
N-[3-(4-nitrophenoxy)-propyl]-diethylamine
N-[3-(4-cyanophenoxy)-propyl]-diethylamine
1-[5-(4-benzoylphenoxy)-pentyl]-pyrrolidine
1-{5-[4-(phenylacetyl)-phenoxy]-pentyl}-pyrrolidine
N-[3-(4-acetylphenoxy)-propyl]-diethylamine
1-[5-(4-acetamidophenoxy)-pentyl]-pyrrolidine
1-[5-(4-phenoxyphenoxy)-pentyl]-pyrrolidine
1-[5-(4-N-benzamidophenoxy)-pentyl]-pyrrolidine
1-{5-[4-(1-hydroxyethyl)-phenoxy]-pentyl}-pyrrolidine
1-[5-(4-cyanophenoxy)-pentyl]-diethylamine
1-[5-(4-cyanophenoxy)-pentyl]-piperidine
N-[5-(4-cyanophenoxy)-pentyl]-dimethylamine
N-[2-(4-cyanophenoxy)-ethyl]-diethylamine
N-[3-(4-cyanophenoxy)-propyl]-dimethylamine
N-[4-(4-cyanophenoxy)-butyl]-diethylamine
N-[5-(4-cyanophenoxy)-pentyl]-dipropylamine
1-[3-(4-cyanophenoxy)-propyl]-pyrrolidine
1-[3-(4-cyanophenoxy)-propyl]-piperidine
N-[3-(4-cyanophenoxy)-propyl]-hexamethyleneimine
N-[6-(4-cyanophenoxy)-hexyl]-diethylamine
N-[3-(4-cyanophenoxy)-propyl]-dipropylamine
N-3-[4-(1-hydroxyethyl)-phenoxy]-propyl-diethylamine
4-(3-diethylaminopropoxy)-acetophenone-oxime
1-[3-(4-acetylphenoxy)-propyl]-piperidine
1-[3-(4-acetylphenoxy)-propyl]-3-methyl-piperidine
1-[3-(4-acetylphenoxy)-propyl]-3,5-trans-dimethyl-piperidine
1-[3-(4-acetyl phenoxy)-propyl]-4-methyl-piperidine
1-[3-(4-propionylphenoxy)-propyl]-piperidine
1-[3-(4-acetylphenoxy)-propyl]-3,5-cis-dimethyl-piperidine
1-[3-(4-formylphenoxy)-propyl]-piperidine
1-[3-(4-isobutyrylphenoxy)-propyl]-piperidine
N-[3-(4-propionylphenoxy)-propyl]-diethylamine
1-[3-(4-butyrylphenoxy)-propyl]-piperidine
1-[3-(4-acetylphenoxy)-propyl]-1,2,3,6-tetrahydropyridine More preferred compounds are:
1-[5-(4-nitrophenoxy)-pentyl]-pyrrolidine
N-[3-(4-cyanophenoxy)-propyl]-diethylamine
N-[3-(4-acetylphenoxy)-propyl]-diethylamine
1-{5-[4-(1-hydroxyethyl)-phenoxy]-pentyl}-pyrrolidine
N-[4-(4-cyanophenoxy)-butyl]-diethylamine
1-[3-(4-cyanophenoxy)-propyl]-piperidine
N-[3-(4-cyanophenoxy)-propyl]-hexamethyleneimine
N-3-[4-(1-hydroxyethyl)-phenoxy]-propyl-diethylamine
4-(3-diethylaminopropoxy)-acetophenone-oxime
1-[3-(4-acetylphenoxy)-propyl]-3-methyl-piperidine
1-[3-(4-acetylphenoxy)-propyl]-4-methyl-piperidine
1-[3-(4-propionylphenoxy)-propyl]-piperidine Compounds of formula (I) in which:
—$NR^1R^2$ is a pyrrolidinyl group, $C_nH_{2n}$ is a linear chain —$(CH_2)_n$— and $n_3$ is zero, X being an oxygen atom with n ranging from 3 to 5, or X being a sulfur atom with n being 4 or 5;
—$NR^1R^2$ is a piperidinyl group, $C_nH_{2n}$ is a linear chain —$(CH_2)_n$— and X is an oxygen atom, $n_3$ being zero with n being 2, 5 or 8 or $n_3$ being 1 with $R^3$ being 4-CN and n being 5;
—$NR^1R^2$ is a diethylamine group, X is an oxygen atom, $C_nH_{2n}$ is a linear chain —$(CH_2)_n$— and $n_3$ is 1, $R^3$ being 4-$NO_2$ or 4-$COCH_3$ with n being 3 or $R^3$ being 4-CN with n being 2 to 4;
—$NR^1R^2$ is a dimethylamine group, X is an oxygen atom, $C_nH_{2n}$ is a linear chain —$(CH_2)_n$— and $n^3$ is 1, $R^3$ being 4-CN with n being 3, are known in the art.

A subject of the invention is thus the use of these compounds as ligands of the histamine $H_3$-receptors in particular as $H_3$-antagonists, agonists and/or partial agonists, in particular to prepare medicaments acting as ligands for the histamine $H_3$-receptors in particular as $H_3$-antagonists and/or agonists, intended for the treatments detailed below.

According to a second aspect, the object of the present invention is non-imidazole compounds analogous to the compounds disclosed in WO 96/29315 and WO 93/14070.

Thus, a first sub-class of the compounds (A) of the invention is defined by the compounds having the following general formula (IIa) and (IIb):

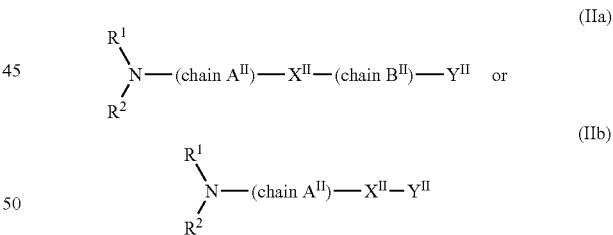

in which
—$R^1$ and $R^2$ are as defined with reference to general formula (A);
the chain $A^{II}$ represents a saturated or unsaturated, straight or branched hydrocarbon chain containing 1 to 6 carbon atoms, it being possible for the saturated hydrocarbon chain to be interrupted by a hetero atom such as a sulphur atom;
$X^{II}$ represents an oxygen or sulphur atom, —NH—, —NHCO—, —N(alkyl)CO—, —NHCONH—, —NH—CS—NH—, —NHCS—, —O—CO—, —CO—O—, —OCONH—, —OCON(alkyl)—, —OCON(alkene), —OCONH—CO—, —CONH—, —CON(alkyl)—, —SO—, —CO—, —CHOH—, —N(saturated or unsaturated alkyl), —S—C(=NY″)—NH—Y‴— with the Y″ identical or different and as defined previously, or —NR″$_{II}$—C(=NR″$_{II}$)—NR'$_{II}$—, R$_{II}$ and R'$_{II}$ denoting a hydrogen atom or a lower alkyl radical and R"$_{II}$ a hydrogen atom or another powerful electronegative group, such as a cyano or COY$_1^{II}$ group, Y$_1^{II}$ denoting an alkoxy group;

the chain B$^{II}$ represents an aryl, arylalkyl or arylalkanoyl group, a straight alkylene chain —(CH$_2$)$_{nII}$—, n being an integer which can vary between 1 and 5 or a branched alkylene chain containing from 2 to 8 carbon atoms, the alkylene chain being optionally interrupted by one or a number of oxygen or sulphur atoms, or a group —(CH$_2$)$_{nII}$—O— or —(CH$_2$)$_{nII}$—S— where n$_{11}$ is an integer equal to 1 or 2;

Y$^{II}$ represents a straight or branched alkyl group containing 1 to 8 carbon atoms; a cycloalkyl containing 3 to 6 carbon atoms; a bicycloalkyl group; a cycloalkenyl group; an aryl group such as an optionally substituted phenyl group; a 5- or 6-membered heterocyclic radical containing one or two heteroatoms chosen from nitrogen and sulphur atoms, the said heterocyclic radical optionally being substituted; or also a bicyclic radical resulting from the fusion of a benzene ring to a heterocycle as defined above.

The chain A can be a straight alkylene chain —(CH$_2$)$_{nII}$—, n$_{II}$ representing an integer between 1 and 6 carbon atoms, preferably between 1 and 4 carbon atoms, or a branched alkylene chain, preferably a chain substituted by one or a number of methyl or ethyl radicals.

The chain A$^{II}$ can also be a straight or branched unsaturated alkylene chain, and can be, for example, the allyl group.

When Y$^{II}$ represents a cycloalkyl group, the latter can be, for example, cyclopentyl, cyclohexyl or a bicycloalkyl group.

When Y$^{II}$ represents a substituted phenyl group, the phenyl group can be mono- or polysubstituted, for example, by a halogen, by a lower alkyl, for example CH$_3$, by CF$_3$, CN, COCH$_3$, COOR$^{II}_1$, or OR$^{II}_1$, R$^{II}_1$ representing a lower alkyl, for example COOCH$_3$, the NO$_2$ group or the group NR$^{II}_2$R$^{II}_3$, R$^{II}_2$ and R$^{II}_3$ representing a hydrogen atom and/or a lower alkyl radical ("lower alkyl" means an alkyl radical containing at most 6 carbon atoms).

When Y$^{II}$ represents a heterocyclic radical, the latter can be, for example, the pyridyl radical, the pyridyl N-oxide radical or the pyrazinyl radical, optionally mono- or polysubstituted by NO$_2$, CF$_3$, CH$_3$, NH$_2$, a halogen such as Cl, the COOCH$_3$ group or also the thiazolyl radical.

When Y$^{II}$ represents a polycyclic radical resulting from condensed aromatic or heteroaromatic moieties the radical can be, for example, the benzothiazolyl, quinolinyl, isoquinolinyl radical or related moieties.

A second sub-class of the compounds (A) according to the invention comprises the compounds having the above-formulae ([la) and (lib) in which:

R$^1$R$^2$ are as defined with reference to general formula (A);

the chain A" represents an unbranched, branched or unsaturated alkyl group —(CH$_2$)$_{nII}$— where n$_{II}$ is an integer which can vary between 1 and 8 and preferably between 1 and 4; an unbranched or branched alkene group comprising from 1 to 8 carbon atoms and preferably 1 to 4 carbon atoms; an unbranched or branched alkyne group comprising from 1 to 4 carbon atoms;

the group X$^{II}$ represents —OCONH—; —OCON(alkyl)—; —OCON(alkene)—; —OCO—; —OCSNH—; —CH$_2$—; —O—; —OCH$_2$CO—; —S—; —CO—; —CS—; amine; saturated or unsaturated alkyl;

the chain B$^{II}$ represents an unbranched, branched or unsaturated lower alkyl comprising from 1 to 8 carbon atoms and preferably 1 to 5 carbon atoms; —(CH$_2$)$_{nII}$(hetero atom)— where the hetero atom is preferably a sulphur or oxygen atom; n$_{II}$ being an integer which can vary between 1 and 5, preferably between 1 and 4;

the group Y$^{II}$ represents a phenyl group, unsubstituted or mono- or polysubstituted with one or more identical or different substituents selected from halogen atoms, OCF$_3$, CHO, CF$_3$, SO$_2$N(alkyl)$_2$ such as SO$_2$N(CH$_3$)$_2$, NO$_2$, S(alkyl), S(aryl), SCH$_2$(phenyl), an unbranched or branched alkene, an unbranched or branched alkyne optionally substituted with a trialkylsilyl radical, —O(alkyl), —O(aryl), —CH$_2$CN, a ketone, an aldehyde, a sulphone, an acetal, an alcohol, a lower alkyl, —CH=CH—CHO, —C(alkyl)=N—OH, —C(alkyl)=N—O(alkyl) and other keto derivatives, —CH=NOH, —CH=NO(alkyl), and other aldehyde derivatives, —C(alkyl)=NH—NH—CONH$_2$, an O-phenyl or —OCH$_2$(phenyl) group, —C(cycloalkyl)=NOH, —C(cycloalkyl)=N—O(alkyl), an optionally substituted heterocycle; a heterocycle comprising a sulphur hetero atom; a cycloalkyl; a bicyclic group and preferably a norbornyl group; a phenyl ring fused to a heterocycle comprising a nitrogen hetero atom or to a carbocycle or a heterocycle bearing a keto function; an unbranched or branched lower alkyl comprising from 1 to 8 carbon atoms; an unbranched or branched alkyne comprising from 1 to 8 carbon atoms and preferably 1 to 5 carbon atoms; a linear or branched alkyl mono- or polysubstituted with phenyl groups which are either unsubstituted or mono- or polysubstituted; a phenyl alkyl ketone in which the alkyl group is branched or unbranched or cyclic; a substituted or unsubstituted benzophenone; a substituted or unsubstituted, unbranched or branched or cyclic phenyl alcohol; an unbranched or branched alkene; a piperidyl group; a phenylcycloalkyl group; a polycyclic group, in particular a fluorenyl group, a naphthyl or polyhydronaphthyl group or an indanyl group; a phenol group; a ketone or keto derivative; a diphenyl group; a phenoxyphenyl group; a benzyloxyphenyl group.

According to the invention, group X$^{II}$ representing an amine is understood to mean a secondary or tertiary amine.

The alkyl, alkene, alkyne, keto, aldehyde, cycloalkyl, S-alkyl, O-alkyl, phenyl alcohol and phenyl-cycloalkyl groups mentioned above as well as in the remainder of the description and the claims of the present patent comprise from 1 to 8 carbon atoms, and preferably 1 to 5.

Likewise, keto derivatives are understood to mean any oxime, alkyloxime, hydrazone, acetal, aminal, ketal, thione, carbazone or semicarbazone group and the thio analogues of these derivatives.

Likewise, by mono- or polysubstituted phenyl and/or benzophenone groups, it is understood to mean that these groups are substituted with one or more identical or different substituents selected from halogen atoms, OCF$_3$, CHO, CF$_3$, SO$_2$N(alkyl)$_2$, SO$_2$N(CH$_3$)$_2$, NO$_2$, S(alkyl), S(aryl), SCH$_2$(phenyl), an unbranched or branched alkene, an unbranched or branched alkyne optionally substituted with a trialkylsilyl radical, —O(alkyl), —O(aryl), —CH$_2$CN, a ketone, an aldehyde, a sulphone, an acetal, an alcohol, a lower alkyl, —CH=CH—CHO, —C(alkyl)=N—OH, —C(alkyl)=N—O(alkyl) an other keto derivatives, —CH=NOH, —CH=NO(alkyl), and other aldehyde derivatives, —C(alkyl)=NH—NH—CONH$_2$, an O-phenyl or —OCH$_2$(phenyl) group, —C(cycloalkyl)=NOH, —C(cycloalkyl)=N—O(alkyl), an optionally substituted heterocycle.

The keto substituent is preferably selected from a linear- or branched-chain aliphatic ketone, it being possible for the said chain to comprise from 1 to 8 carbon atoms and optionally to bear a hydroxyl group, a cycloalkyl ketone, an aryl alkyl ketone or aryl alkenyl ketone in which the aryl group is unsubstituted or mono- or polysubstituted, or a heteroaryl ketone in which the heteroaryl unit is preferably monocyclic.

The acetal substituent preferably consists of an aliphatic acetal comprising from 1 to 8 carbon atoms and optionally bearing a hydroxyl radical.

Group $Y^{II}$ representing a ketone is understood to mean, in particular, a ketone substituted with an alkyl or aryl group, it being possible for these groups to be substituted or unsubstituted.

As regards the heterocycles, these comprise from 1 to 3 hetero atoms, preferably sulphur, oxygen or nitrogen atoms.

The heterocycle substituent is preferably selected from an oxadiazole or an imidazole.

Preferred compounds (IIa) and (IIb) are those in which $X^{II}$ is selected from —O—, —NH—, —CH$_2$—, —OCONH—, —NHCO—, —NHCONH—. $X^{II}$ represents more preferably an oxygen atom.

Preferred compounds (IIa) and (IIb) are also those in which $Y^{II}$ is selected from a linear or branched alkyl group as above defined; a cycloalkyl group as above-defined, in particular cyclopentyl or cyclohexyl group; a phenyl group unsubstituted or mono-substituted, preferred substituent being halogen atom, in particular chorine; a heterocyclic radical, in particular pyridyl N-oxide or pyrazinyl radicals; a bicyclic radical such as a benzothiazolyl radical.

$Y^{II}$ is preferably a phenyl group at least mono-substituted with —CHO, a ketone, an aldehyde, —CH═CH—CHO, —C(alkyl)═N—OH, —C(alkyl)═N—O(alkyl) and other keto derivatives, —CH═N—OH, —CH═NO(alkyl) and other aldehyde derivatives, —C(cycloalkyl)═NOH, —C(cycloalkyl)═N—O(alkyl).

According to the invention, $Y^{II}$ represents especially a phenyl group at least mono-substituted with a keto-substituent or an oxime-substituent, or an halogen atom.

Particularly preferred keto-substituent is cycloalkylketone.

Other preferred compounds are those wherein $Y^{II}$ represents a phenyl group fused to a carbocycle bearing a keto-function.

Yet other preferred $Y^{II}$ are phenylalkyl ketone in which the alkyl group is branched or unbranched or cyclic; an optionally substituted benzophenone, a ketone.

Particularly preferred group $Y^{II}$ are a phenyl group unsubstituted or mono-substituted as above-defined.

The chain $A^{II}$ is preferably a chain —(CH$_2$)$_{n}$$^{II}$— with $n_{II}$ varying from 1 to 6, preferably from 1 to 4. The chain $A^{II}$ represents especially —(CH$_2$)$_3$—.

Preferred chain $B^{II}$ is —(CH$_2$)$_2$— or —(CH$_2$)$_3$—.

Among compounds (IIa) and (IIb), particularly preferred compounds are those in which $X^{II}$ is an oxygen atom, the chain $A^{II}$ represents —(CH$_2$)$_3$— and, for compounds of formula (IIa), the chain $B^{II}$ represents —(CH$_2$)$_3$— also.

In this group, $Y^{II}$ is preferably an aryl group. Preferred group $R^1$ and $R^2$ are as above-defined with reference to formula (A).

Examples of compounds (IIa) and (IIb) are:
3,3-Dimethylbutyl 3-piperidinopropylether
3-Phenylpropyl 3-piperidinopropylether
3-(4-Chlorophenyl)propyl 3-piperidinopropylether
2-Benzothiazolyl 3-piperidinopropylether
3-Phenylpropyl 3-(4-methylpiperidino)propylether
3-Phenylpropyl 3-(3,5-cis-dimethylpiperidino)propylether
3-Phenylpropyl 3-(3,5-trans-dimethylpiperidino)propylether
3-Phenylpropyl 3-(3-methylpiperidino)propylether
3-Phenylpropyl 3-pyrrolidinopropylether
3-(4-Chlorophenyl)propyl 3-(4-methylpiperidino)propylether
3-(4-Chlorophenyl)propyl 3-(3,5-cis-dimethylpiperidino)propylether
3-(4-Chlorophenyl)propyl 3-(3,5-trans-dimethylpiperidino)propylether
3-Phenylpropyl 3-(N,N-diethylamino)propylether
N-Phenyl-3-piperidinopropyl carbamate
N-Pentyl-3-piperidinopropyl carbamate
(S)-(+)-N-[2-(3,3-Dimethyl)butyl]-3-piperidinopropyl carbamate
3-Cyclopentyl-N-(3-(1-pyrrolidinyl)propyl)propanamide
N-Cyclohexyl-N'-(1-pyrrolidinyl-3-propyl)urea
2-((2-Piperidinoethyl)amino)benzothiazole
5-Piperidinopentylamine
2-Nitro-5-(6-piperidinohexyl)pyridine
3-Nitro-2-(6-piperidinohexylamino)pyridine
2-(6-Piperidinohexylamino)pyrimidine
N-(6-Phenylhexyl)piperidine
N-(3-(N,N-Diethylamino)propyl)N'-phenylurea
N-Cyclohexyl methyl-N'-(3-piperidinopropyl)guanidine According to a third aspect, the object of the present invention is non-imidazole compounds analogous to the compounds disclosed in EP 197 840.

Thus, a sub-class of compounds (A) according to the invention comprises compounds having the following formula (III)

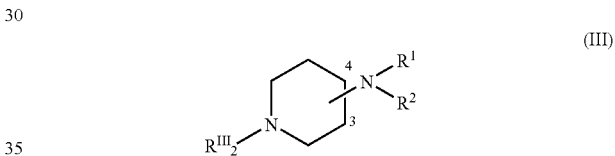

in which:
NR$^1$R$^2$ is either in 3-position or in 4-position on the piperidyl moiety, R$^1$ and R$^2$ being as defined with reference to formula (A);
R$_2$$^{III}$ denotes a linear or branched alkyl group having 1 to 6 carbon atoms; a piperonyl group, a 3-(1-benzimidazolonyl)propyl group; a group of formula

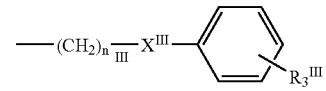

in which $n_{III}$ is 0, 1, 2 or 3, $X^{III}$ is a single bond or alternatively —O—, —S—, —NH—, —CO—, —CH═CH— or

and R$_3$$^{III}$ is H, CH$_3$, halogen, CN, CF$_3$ or an acyl group —COR$_4$$^{III}$, R$_4$$^{III}$ being a linear or branched alkyl group having 1 to 6 carbon atoms, a cycloalkyl group having 3 to 6 carbon atoms or a phenyl group which can bear a $CH_3$ or F substituent; or alternatively a group of formula $$-\underset{\underset{Z^{III}}{\|}}{C}-NH-R_5^{III}$$

in which $Z^{III}$ denotes an O or S atom or a divalent group NH, N—$CH_3$ or N—CN and $R_5^{III}$ denotes a linear or branched alkyl group having 1 to 8 carbon atoms, a cycloalkyl group having 3 to 6 carbon atoms which can bear a phenyl substituent, a ($C_3$–$C_6$ cycloalkyl) (linear or branched, $C_1$–$C_3$ alkyl) group, a phenyl group which can bear a $CH_3$, halogen or $CF_3$ substituent, a phenyl(linear or branched, $C_1$–$C_3$ alkyl) group or a naphthyl, adamantyl or p-toluenesulphonyl group.

Preferred compounds (III) are those with $R^{III}$ representing the group $$-\underset{\underset{Z^{III}}{\|}}{C}-NH-R^{III}_5$$

, $Z^{III}$ and $R^{III}_5$ being as above-defined and $Z^{III}$ is especially O, S or NH.

Preferred group $R^{III}_5$ is a ($C_3$–$C_6$)cycloalkyl group.

Preferred $R^1$ and $R^2$ groups are as above-described in formula (A).

An example of such compound (III) is N'-Cyclohexylthiocarbamoyl-N-1,4'-bipiperidine (compound 123).

According to a fourth aspect, a sub-class of compounds (A) includes the compounds which have the following formula (IV), analogous to compounds disclosed in EP 494 010:

(IV)

in which $R^1$ and $R^2$ are as defined with reference to general formula (A);

$R^{IV}$ represents a hydrogen atom or a group $COR_3^{IV}$, in which $R_3^{IV}$ represents (a) a linear or branched aliphatic group containing 1 to 11, and in particular 1 to 9, carbon atoms;

(b) a cyclane ring-system such as cyclopropane, phenylcyclopropane, cyclobutane, cyclopentane, cyclohexane, cycloheptane, norbornane, adamantane, noradamantane, chlorooxonorbornane, chloroethylenedioxynorbornane, bromoethylenedioxynorbornane and the anhydride group of hydroxycarboxy-1,2,2-trimethylcyclopentanecarboxylic acid;

(c) a benzene ring, unsubstituted or substituted at the para-position with a linear or branched aliphatic group containing 3 to 5 carbon atoms, as well as with a halogen;

(d) a group $(CH_2)_{m_{IV}}R_4^{IV}$ in which $m_{IV}$ is a number between 1 and 10, and $R_4^{IV}$ represents a cyclane ring system such as cyclopropane, cyclobutane, cyclopentane, cyclopentene, cyclohexane, cycloheptane, norbornane, noradamantane, adamantane and 6,6-dimethylbicyclo[3.1.1]heptene; a benzene ring, unsubstituted or monosubstituted with a fluorine atom, a chlorine atom, a methyl group or a methoxy group; a thiophene ring grafted via its ring-position 2 or its ring-position 3; a carboxylic acid ester group $COOR_5^{IV}$, in which $R_5^{IV}$ is a cyclane ring-system such as cyclopropane, cyclobutane, cyclopentane, cyclohexane or norbornane; a carboxylic acid amide group of structure $CONHR_6^{IV}$, in which $R_6^{IV}$ represents a cyclane ring-system such as cyclopropane, cyclobutane, cyclopentane, cyclohexane or norbornane; a carboxylic acid amide group of structure $$CON\overset{\diagup}{\diagdown}\quad N\overset{\diagup}{\diagdown}$$

in which the group represents pyrrolidine, piperidine or 2,6-dimethylmorpholine; or an ether group —O—$R_7^{IV}$, it being possible for $R_7^{IV}$ to be a benzene ring, unsubstituted or monosubstituted with a chlorine or fluorine atom or disubstituted with a chlorine atom and with a methyl group;

(e) a group —CH=$CHR_8^{IV}$, in which $R_8^{IV}$ represents a cyclane ring-system such as cyclopropane, cyclobutane, cyclopentane, cyclohexane, norbornane or norbornene;

(f) a secondary amine group —$NH(CH_2)_{n_{IV}}R_9^{IV}$, in which $n_{IV}$ is a number between 1 and 5 and $R_9^{IV}$ constitutes a cyclane ring-system such as cyclopropane, cyclobutane, cyclopentane, cyclohexane or norbornane, or a benzene ring, unsubstituted, mono-substituted with a fluorine or chlorine atom or with a methoxy group or trisubstituted with methoxy groups;

$R^{IV}$ also represents a hydroxyalkenyl group $$\underset{HO}{\overset{\diagdown}{\diagup}}C=CH(CH_2)_{p_{IV}}R_{10}^{IV}$$

in which $p_{IV}$ is a number between 2 and 9 and $R_{10}^{IV}$, represents a benzene ring or a phenoxy group; as well as a group $CSNH(CH_3)_{n_{IV}}R_9^{IV}$ in which $n_{IV}$ is a number between 1 and 5 and $R_9^{IV}$ has the meaning stated above.

Preferred compounds (IV) are those in which $R^{IV}$ represents the group $COR_3^{IV}$, $R_3^{IV}$ representing especially an aliphatic group a).

An example of compound (IV) is N-Heptanoyl-1,4'-bipiperidine or 1-(5-Cyclohexylpentanoyl)-1,4-bipiperidine.

According to a fifth aspect, the invention is relative to non-imidazole compounds analogous to those disclosed by Plazzi et al. (Eur. J. Med. Chem. 1995, 30, 881).

Thus, another sub-class of compounds (A) comprises compounds having the following formula (V):

(V)

in which

R¹ and R² are as defined with reference to formula (A) in claim 1;

$q^V$ is 2 to 5

$Z^V$ represents NH, O or S $X_V$ represents a heterocycle, optionally condensed, containing one or more heteroatoms like nitrogen, oxygen or sulfur, unsubstituted or substituted by one or more groups like aryl, lower alkyl and halogen.

Preferred compounds are those with $X^V$ being an heterocycle like:

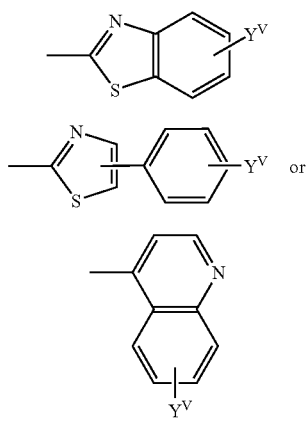

with $Y^V$ representing an hydrogen atom, an halogen or a lower alkyl.

Examples of compounds (V) are:

2-((2-Piperidinoethyl)amino)benzothiazole
2-(6-Piperidinohexylamino)benzothiazole
4-(6-Piperidinohexylamino)quinoline
2-Methyl 4-(3-piperidinopropylamino)quinoline
2-Methyl 4-(6-piperidinohexylamino)quinoline
7-Chloro-4-(3-piperidinopropylamino)quinoline
7-Chloro-4-(4-piperidinobutylamino)quinoline
7-Chloro-4-(8-piperidinooctylamino)quinoline
7-Chloro-4-(10-piperidinodecylamino)quinoline
7-Chloro-4-(12-piperidinododecylamino)quinoline
7-Chloro-4-(4-(3-piperidinopropoxy)phenylamino)quinoline
7-Chloro-4-(2-(4-(3-piperidinopropoxy)phenyl)ethylamino)quinoline According to a sixth aspect, the present invention concerns non-imidazole compounds which are analogous to those disclosed in WO 95/14007.

Thus, another subclass of compounds (A) includes the compounds having the following formula (VI):

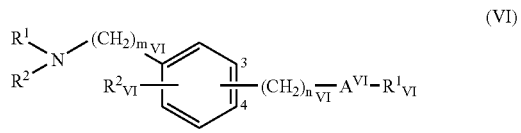

wherein:

$A^{VI}$ is selected from —O—CO—$NR^1_{VI}$—, —O—CO—, —$NR^1_{VI}$—CO—, —$NR^1_{VI}$—, —$NR^1_{VI}$—CO—, —$NR^1_{VI}$—, —O—, —CO—$NR^1_{VI}$—, —CO—O—, and —C(=$NR^1_{VI}$)—$NR^1_{VI}$—;

the groups $R^1_{VI}$, which may be the same or different when there are two or three such groups in the molecule of formula VI, are selected from hydrogen, and lower alkyl, aryl, cycloalkyl, heterocyclic and heterocyclyl-alkyl groups, and groups of the formula —$(CH_2)_{y_{VI}}$—$G^{VI}$, where $G^{VI}$ is selected from $CO_2R^3_{VI}$, $COR^3_{VI}$, $CONR^3_{VI}R^4_{VI}$, $OR^3_{VI}$, $SR^3_{VI}$, $NR^3_{VI}R^4_{VI}$, heteroaryl and phenyl, which phenyl is optionally substituted by halogen, lower alkoxy or polyhaloloweralkyl, and $y_{VI}$ is an integer from 1 to 3;

$R^2_{VI}$ is selected from hydrogen and halogen atoms, and alkyl, alkenyl, alkynyl and trifluoromethyl groups, and groups of the formula $OR^3_{VI}$, $SR^3_{VI}$ and $NR^3_{VI}R^4_{VI}$;

$R^3_{VI}$ and $R^4_{VI}$ are independently selected from hydrogen, and lower alkyl and cycloalkyl groups, or $R^3_{VI}$ and $R^4_{VI}$, together with the intervening nitrogen atom can form a saturated ring containing 4 to 6 carbon atoms that can be substituted with one or two lower alkyl groups;

the group —$(CH_2)_{n_{VI}}$—$A^{VI}$—$R^1_{VI}$ is at the 3- or 4-position, and the group $R^2_{VI}$ is at any free position;

$m_{VI}$ is an integer from 1 to 3;

and $n_{VI}$ is 0 or an integer from 1 to 3.

When used herein, the following terms have the given meanings:

lower alkyl (including the alkyl portions of lower alkoxy)—represents a straight or branched, saturated hydrocarbon chain having from 1 to 6 carbon atoms, preferably from 1 to 4;

lower alkenyl (in $R^2_{VI}$)—represents a straight or branched aliphatic hydrocarbon radical having at least one carbon-to-carbon double bond (preferably in conjugation with the benzene ring that the group $R^2$ substitutes) and having from 2 to 6 carbon atoms;

lower alkynyl (in $R^2_{VI}$)—represents a straight or branched aliphatic hydrocarbon radical having at least one carbon-to-carbon triple bond (preferably in conjugation with the benzene ring that the group $R^2$ substitutes) and having from 2 to 6 carbon atoms;

aryl—represents a carbocyclic group having from 6 to 14 carbon atoms and having at least one benzenoid ring, with all available substitutable aromatic carbon atoms of the carbocyclic group being intended as possible points of attachment, said carbocyclic group being optionally substituted with 1 to 3 $Y_{VI}$ groups, each independently selected from halo, alkyl, hydroxy, loweralkyoxy, phenoxy, amino, loweralkylamino, diloweralkylamino, and polyhaloloweralkyl. Preferred aryl groups include 1-naphthyl, 2-naphthyl and indanyl, and especially phenyl and substituted phenyl;

cycloalkyl—represents a saturated carbocyclic ring having from 3 to 8 carbon atoms, preferably 5 or 6;

halogen—represents fluorine, chlorine, bromine and iodine;

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms; e.g., 2- or 3-piperidinyl, 2- or 3-piperazinyl, 2- or 3-morpholinyl, or 2- or 3-thiomorpholinyl;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 2-, 4- or 5-pyrimidinyl, 2-pyrazinyl, or 3- or 4-pyridazinyl, etc.

Preferred heteroaryl groups are 2-, 3- and 4-pyridyl;

heterocyclyl-alkyl—represents a heterocyclic group defined above substituting an alkyl group; e.g., 2-(3-piperidinyl)-ethyl, (2-piperazinyl)-methyl, 3-(2-morpholinyl)-propyl, (3-thiomorpholinyl)-methyl, 2-(4-pyridyl)-ethyl, (3-pyridyl)-methyl, or (2-thienyl)-methyl.

Preferably, $A^{VI}$ is —$CH_2$—$NR^1_{VI}$— or especially —C(=NH)—$NR^1_{VI}$— preferred compounds include those wherein $m_{VI}$ is 1 or 2, and $n_{VI}$ is 0, 1 or 2.

Other preferred values of A include —O—CO—$NR^1_{VI}$—, —O—, and —CO—O—. In all these compounds, the groups $R^1_{VI}$ are as defined above, and the side chain is preferably at the 4-position. In compounds of formula VI, one group $R^1_{VI}$ is preferably selected from hydrogen, 2-phenylethyl, 4-chlorophenylmethyl, 4-methoxyphenylmethyl, 4-trifluoromethylphenylmethyl and 4-pyridylmethyl, but is especially 4-chlorophenylmethyl; any other group $R^1_{VI}$ that is present is preferably a hydrogen atom or a methyl group.

Particularly preferred compounds are those wherein $n_{VI}$ and $m_{VI}$ are each 1, and $A^{VI}$ represents an oxygen atom.

$R^1_{VI}$ is preferably an aryl or —$(CH_2)_{yVI}$—$G^{VI}$ with $G^{VI}$ being a phenyl.

$R^1$ and $R^2$ are preferably selected as specified with reference to formula (A).

Another sub-class of compounds (A) comprises compounds of formula (VI) wherein $R^1_{VI}$ represents an aryl group, especially a phenyl optionally substituted with a keto substituent, $R^2_{VI}$, $n_{VI}$, $m_{VI}$ and $A^{VI}$ having the above-meaning.

The keto substituent is as above-defined in $Y^{II}$ with reference to compounds (IIa) and (IIb).

Preferred compounds are those with $n_{VI}$ and $m_{VI}$ being each 1 and $A^{VI}$ being an oxygen atom.

Examples of compounds VI are:

α-(Acetylphenoxy)-α'-piperidino p-xylol
α-(4-Acetylphenoxy)-α'-(1-pyrrolidinyl)p-xylol
α-(3-Phenylpropoxy)-α'-piperidino p-xylol
α-(4-Acetylphenoxy)-α'-(4-methylpiperidino)p-xylol
α-(4-Acetylphenoxy)-α'-(3,5-cis-dimethylpiperidino)p-xylol
α-(4-Acetyl phenoxy)-α'-(3,5-trans-dimethylpiperidino)p-xylol
α-(4-Acetylphenoxy)-α'-(2-methylpyrrolidino)p-xylol
α-(4-Cyclopropylcarbonylphenoxy)-α'-piperidino-p-xylol
α-(4-Cyclopropylcarbonylphenoxy)-α'-(4-methylpiperidino)p-xylol
α-(4-Cyclopropylcarbonylphenoxy)-α'-pyrrolidino-p-xylol
N-(4-Chlorobenzyl)-2-(4-piperidino methyl) phenyl)ethanamidine According to a seventh aspect, the present invention is directed to another sub-class of compounds (A) including non-imidazole compounds having the following formula (VII) which are analogous to compounds disclosed in Clitherow et al. (Bioorg. & Med. Chem. Lett., 6 (7), 833, 1996):

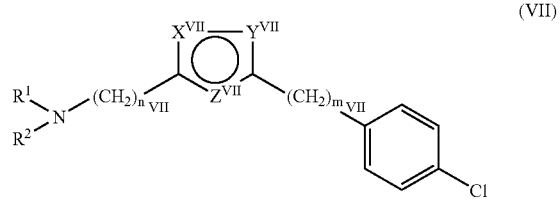

(VII)

in which

—$R^1$ and $R^2$ are as defined in reference to formula (A);

$X^{VII}$, $Y^{VII}$ and $Z^{VII}$ are identical or different and represent O, N or S;

$n_{VII}$ is varying from 1 to 3;

$m_{VII}$ is 1 or 2.

$n_{VII}$ is preferably 2 or 3, especially 2 and $m_{VII}$ is preferably 1.

Preferred compounds are those with $X^{VII}$ being 0 and $Y^{VII}$ and $Z^{VII}$ each being N to represent a 1,2,4-oxadiazolyl group.

An illustrative compound is given in example 130.

According to a eighth aspect, the present invention is directed to another sub-class of compounds (A) including the non-imidazole compounds having the following formula (VIII), which are analogous to those disclosed in WO 95/06037:

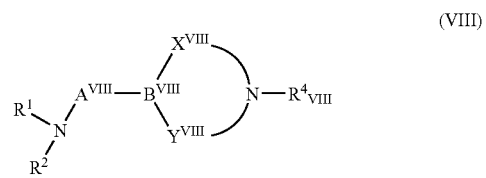

(VIII)

wherein $R^1$ and $R^2$ are as defined with reference to formula (A) and wherein $A^{VIII}$ is 1) a group of the formula $(CH_2)_{mVIII}$, wherein $m_{VIII}$=0–9; or 2) a group of the formula:

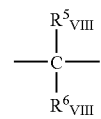

wherein $R^5_{VIII}$ represents hydrogen, $(C_1$–$C_3)$alkyl-, aryl $(C_1$–$C_3)$alkyl-, aryl-, wherein aryl may optionally be substituted, hydroxyl-, $(C_1$–$C_3)$alkoxy-, halogen, amino-, cyano- or nitro; and $R^6_{VIII}$ represents hydrogen, $(C_1$–$C_3)$ alkyl-, aryl$(C_1$–$C_3)$alkyl-, or aryl-, wherein aryl may optionally be substituted; or 3) a group of the formula:

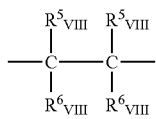

wherein $R^5_{VIII}$ and $R^6_{VIII}$ are as defined above; or
   4) a group of the formula:

if $B^{VIII}$ is a group of the formula:

such that $A^{VIII}$ and $B^{VIII}$ together form a group of the formula:

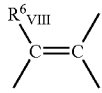

wherein $R^6_{VIII}$ is as defined above; or
   5) a group of the formula:

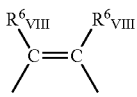

wherein $R^6_{VIII}$ is as defined above; or
   6) a group of the formula:

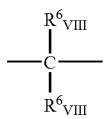 if $B^{VIII}$ is a group of the formula: 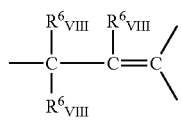

such that $A^{VIII}$ and $B^{VIII}$ together form a group of the formula:

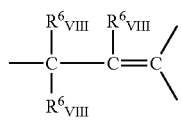

wherein $R^6_{VIII}$ is as defined above; or 7) a group of the formula:

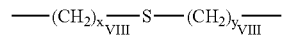

wherein $x_{VIII} + y_{VIII} = m_{VIII} - 1$;
$B^{VII}$ is
   1) a group of the formula:

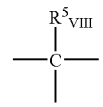

wherein $R^5_{VIII}$ is as defined above; or
   2) a group of the formula:

if A is a group of one of the formulas:

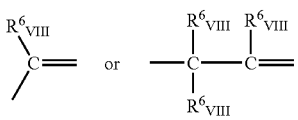

such that A and B together form a group of one of the formulas:

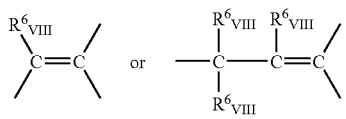

wherein $R^6_{VIII}$ is as defined above; or
   3) a group of the formula:

if $X^{VIII}$ is a group of the formula:

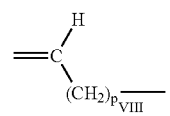

such that $B^{VIII}$ and $X^{VIII}$ together form a group of the formula

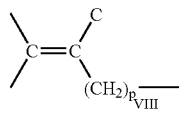

wherein $p_{VIII}=1\text{-}3$; or $X^{VIII}$ is 1) a group of the formula $(CH_2)_{n_{VIII}}$ wherein $n_{VIII}=2\text{-}4$; or
2) a group of the formula:

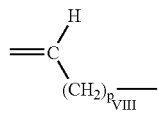

if $B^{VIII}$ is a group of the formula:

such that $X^{VIII}$ and $B^{VIII}$ together form a group of the formula:

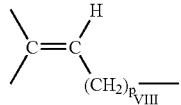

wherein $p_{VIII}=1\text{-}3$; or 3) two hydrogens (one on the carbon and one on the nitrogen); or
4) one hydrogen on the carbon atom and one $R^7_{VIII}$ group on the nitrogen atom, wherein $R^7_{VIII}$ represents hydrogen, $(C_1\text{-}C_{10})$alkyl-, aryl $(C_1\text{-}C_{10})$alkyl-, or aryl, wherein aryl may optionally be substituted;

$Y^{VIII}$ is a group of the formula $(CH_2)_{k_{VIII}}$, wherein $k_{VIII}=0\text{-}2$;

$R^4_{VIII}$ represents hydrogen, $(C_1\text{-}C_{10})$alkyl-, $(C_1\text{-}C_3)$alkyl-sulfonamide-, aryl$(C_1\text{-}C_{10})$alkyl-, aryl, wherein aryl may optionally be substituted;

or a group of the formula:

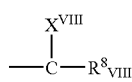

or a group of the formula:

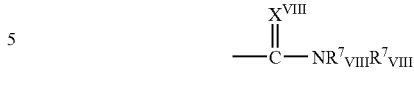

wherein $X^{VIII}$ represents O, S, or NH, $R^7_{VIII}$ is as defined as above;

$R^8_{VII}$ represents $(C_1\text{-}C_{10})$alkyl-, aryl$(C_1\text{-}C_{10})$alkyl- or aryl, wherein aryl may optionally be substituted and wherein aryl is phenyl, substituted phenyl, naphtyl, substituted naphtyl, pyridyl.

The present invention comprises both linear and ring-structured compounds.

The linear compounds have for example one of the formulas

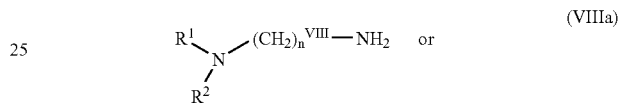

(VIIIa)

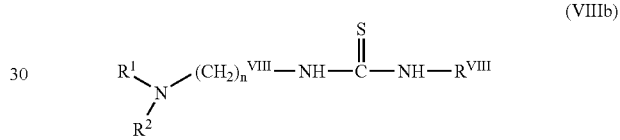

(VIIIb)

Preferred $R^1$ and $R^2$ groups are as defined with reference to formula (A).

A compound (VIII) is described in examples 132 and 169.

According to a ninth aspect, the invention is relative to a sub-class of compounds (A) consisting of compounds having the following formula (IX) which are analogous to those described in WO 97/29092:

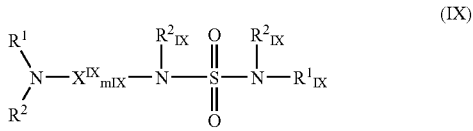

(IX)

wherein:

$R^1$ and $R^2$ are as defined with reference to formula (A)

$R^1_{IX}$ is $C_4$ to $C_{20}$ hydrocarbyl (in which one or more hydrogen atoms may be replaced by halogen, and up to four carbon atoms [and especially from 0 to 3 carbon atoms] may be replaced by oxygen, nitrogen or sulphur atoms, provided that $R^1_{IX}$ does not contain an —O—O-group), $R^2_{IX}$ identical or different, are H or $C_1$ to $C_{15}$ hydrocarbyl (in which one or more hydrogen atoms may be replaced by halogen, and up to three carbon atoms may be replaced by oxygen, nitrogen or sulphur atoms, provided that $R^2_{IX}$ does not contain an —O—O-group), $m_{IX}$ is from 1 to 15 (preferably 1 to 10, more preferably 3 to 10, eg. 4 to 9)

each $X^{IX}$ group is independently

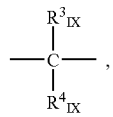

or one $X^{IX}$ group is —N($R^4_{IX}$)—, —O— or —S— (provided that this $X^{IX}$ group is not adjacent the —$NR^2_{IX}$— group) and the remaining $X^{IX}$ groups are independently

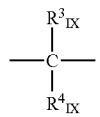

,wherein $R^3_{IX}$ is H, $C_1$ to $C_6$ alkyl, $C_2$ to $C_6$ alkenyl, —$CO_2R^5_{IX}$, —$CON(R^5_{IX})_2$, —$CR^5_{IX2}OR^6_{IX}$ or —$OR^5_{IX}$ (in which $R^5_{IX}$ and $R^6_{IX}$ are H or $C_1$ to $C_3$ alkyl), and $R^4_{IX}$ is H or $C_1$ to $C_6$ alkyl.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups.

A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above.

When reference is made herein to a substituted carbocyclic group (such as substituted phenyl), or a substituted heterocyclic group, the substituents are preferably from 1 to 3 in number and selected from $C_1$ to $C_6$ alkyl, $C_1$ to $C_6$ alkoxy, $C_1$ to $C_6$ alkylthio, carboxy, $C_1$ to $C_6$ carboalkoxy, nitro, trihalomethyl, hydroxy, amino, $C_1$ to $C_6$ alkylamino, di($C_1$ to $C_6$ alkyl)amino, aryl, $C_1$ to $C_6$ alkylaryl, halo, sulphamoyl and cyano.

The term "halogen", as used herein, refers to any of fluorine, chlorine, bromine and iodine.

Preferably, $R^2_{IX}$ is selected from H, $C_1$ to $C_6$ alkyl, $C_1$ to $C_6$ cycloalkyl, $C_1$ to $C_6$ hydroxyalkyl, $C_1$ to $C_6$ alkylhydroxyalkyl, aryl $C_1$ to $C_6$ alkyl and substituted aryl $C_1$ to $C_6$ alkyl. For example, $R^2_{IX}$ may be H or $C_1$ to $C_3$ alkyl.

In certain embodiments, —$X^{IX}_{mIX}$— is a $C_1$ to $C_8$ alkylene group, e.g. a butylene group.

Included in the definition of $R^1_{IX}$ are aryl-containing groups (such as phenyl, substituted phenyl, naphthyl and substituted naphthyl), and (cycloalkyl)alkyl groups (such as cyclohexylpropyl and adamantylpropyl).

Preferably, $R^1_{IX}$ is a group of the formula

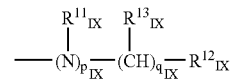

wherein $p_{IX}$ is 0 or 1, $R^{11}_{IX}$ is H or $C_1$ to $C_3$ alkyl, $q_{IX}$ is from 0 to 4, $R^{12}_{IX}$ is a carboxyclic, substituted carbocyclic, heterocyclic or substituted heterocyclic group, and $R^{13}_{IX}$ is independently selected from H, $C_1$ to $C_6$ alkyl, $C_1$ to $C_6$ cycloalkyl, $C_1$ to $C_6$ hydroxyalkyl, $C_1$ to $C_6$ alkylhydroxyalkyl, aryl $C_1$ to $C_6$ alkyl and substituted aryl C, to $C_6$ alkyl.

Preferably, $R^{13}_{IX}$ is hydrogen.

Compounds (IX) wherein $R^1_{IX}$ is a group —NH—$CH_2$— Ph where Ph represents an optionally substituted phenyl, are preferred.

Preferred groups $R^1$ and $R^2$ are as specified with reference to formula (A).

An illustrative example is compound 173.

According to a tenth aspect, the present invention is relative to another sub-class of compounds (A) comprising compounds having the following formula (X), which are analogous to compounds disclosed by Wolin et al. (Bioorg. & Med. Chem. Lett., 8, 2157 (1998)):

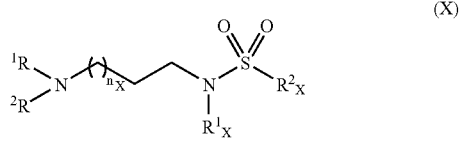

wherein:

$R^1$ and $R^2$ are as defined with reference to formula (A);

$R^1_X$ is H or $CH_3$;

$R^2_X$ is selected from a phenyl optionally substituted with a halogen atom, preferably chlorine, a ($C_1$–$C_4$)alkyl, a ($C_1$–$C_4$)alkoxy, $CF_3$, $OCF_3$, $NO_2$, $NH_2$; or a $CH_2$-phenyl optionally substituted as above-specified;

$n_X$ is from 0 to 3.

$n_X$ is preferably 1. $R^2$ is preferably a phenyl group, especially a mono-substituted phenyl group.

Preferred $R^1$ and $R^2$ are as above-specified for formula (A).

Compound 174 is illustrative of compounds (X).

According to a eleventh aspect, the invention is directed to non-imidazole compounds which are analogous to those disclosed in WO 96/38142.

Thus, another sub-class of compounds (A) of the invention is directed to compounds having the following formula (XI):

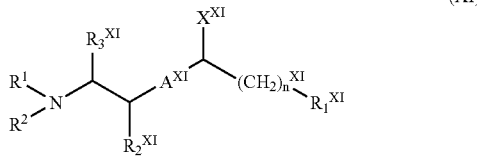

where $R^1$ and $R^2$ are as defined with reference to formula (A);

where $A^{XI}$ is —NHCO—, —N(CH$_3$)—CO—, —NHCH$_2$—, —N(CH$_3$)—CH$_2$—, —CH=CH—, —COCH$_2$—, CH$_2$CH$_2$—, —CH(OH)CH$_2$—, or —C≡C—;

$X^{XI}$ is H, CH$_3$, NH$_2$, NH(CH$_3$), N(CH$_3$)$_2$, OH, OCH$_3$, or SH;

$R_2^{XI}$ is hydrogen or a methyl or ethyl group;

$R_3^{XI}$ is hydrogen or a methyl or ethyl group;

$n^{XI}$ is 0, 1, 2, 3, 4, 5 or 6; and $R_1^{XI}$ is selected from the group consisting of C$_3$ to C$_8$ cycloalkyl; phenyl or substituted phenyl; decahydronaphthalene and octahydroindene; or $R_1^{XI}$ and $X^{XI}$ may be taken together to denote a 5,6 or 6,6 saturated bicyclic ring structure when $X^{XI}$ is NH, O, S, or SO$_2$.

Preferably for compounds of formula (XI):

$A^{XI}$ is —NHCO—, —N(CH$_3$)—CO—, —NHCH$_2$—, —N(CH$_3$)—CH$_2$—, —CH=CH—, —COCH$_2$—, —CH$_2$CH$_2$—, —CH(OH)CH$_2$—, or —C≡C—;

$X^{XI}$ is H, CH$_3$, NH$_2$, NH(CH$_3$), N(CH$_3$)$_2$, OH, OCH$_3$, or SH;

$R_2^{XI}$ is hydrogen or a methyl or ethyl group;

$R_3^{XI}$ is hydrogen or a methyl or ethyl group;

$n^{XI}$ is 0, 1, 2, 3, 4, 5, or 6; and $R_1^{XI}$ is selected from the group consisting of (a) C$_3$ to C$_8$ cycloalkyl; (b) phenyl or substituted phenyl; (d) heterocyclic (e) decahydronaphthalene and (f) octahydroindene; or $R_1^{XI}$ and $X^{XI}$ may be taken together to denote a 5,6 or 6,6 saturated bicyclic ring structure when $X^{XI}$ can be NH, O, or S.

More preferably, the present invention provides compounds where $A^{XI}$ is —NHCH$_2$—, —N(CH$_3$)—CH$_2$—, —CH=CH—, —COCH$_2$—, —CH$_2$CH$_2$, —CH(OH)CH$_2$—, or —C≡C—;

$X^{XI}$ is H, CH$_3$, NH$_2$, NH(CH$_3$), N(CH$_3$)$_2$, OH, OCH$_3$, or SH;

$R_2^{XI}$ is hydrogen or a methyl or ethyl group;

$R_3^{XI}$ is hydrogen or a methyl or ethyl group;

$n^{XI}$ is 0, 1, 2, 3, 4, 5, or 6; and $R_1^{XI}$ is selected from the group consisting of (a) C$_3$ to C$_8$ cycloalkyl; (b) phenyl or substituted phenyl; (d) heterocyclic; (e) decahydronaphthalene and (f) octahydroindene; or $R_1^{XI}$ and $X_{XI}$ may be taken together to denote a 5,6 or 6,6 saturated bicyclic ring structure when $X^{XI}$ can be NH, O, or S.

Most preferably, the present invention provides compounds where $A^{XI}$ is —CH=CH or —C≡C—;

$X^{XI}$ is H, CH$_3$ or NH$_2$;

$R_2^{XI}$ and $R_3^{XI}$ are H;

$n^{XI}$ is 1, 2, or 3;

$R_1^{XI}$ is selected from the group consisting of (a) C$_3$ to C$_8$ cycloalkyl; (b) phenyl or substituted phenyl; (d) heterocyclic; (e) decahydronaphthalene and (f) octahydroindene; or $R_1^{XI}$ and $X^{XI}$ may be taken together to denote a 5,6 or 6,6 saturated bicyclic ring structure when $X^{XI}$ is NH, O, or S.

The term "substituted phenyl" as used herein refers to a phenyl group substituted by one or more groups such as alkyl, halogen, amino, methoxy and cyano groups.

The term "alkyl" refers to straight or branched chain radicals. Representative examples of alkyl groups include methyl, ethyl, n-propyl, isopropyl, n-butyl, sec-butyl, isobutyl, tert-butyl and the like.

Compounds (XI) where $A^{XI}$ is —CH=CH— or —C≡C—, $X^{XI}$, $R_2^{XI}$ and $R_3^{XI}$ are each H, $n_{XI}$ is 1 and $R_1^{XI}$ is a C$_3$–C$_8$ cycloalkyl, are especially preferred.

$R^1$ and $R^2$ are preferably selected as above-indicated in reference to formula (A).

Representative particularly preferred compounds are compounds 177, 178 or 179.

According to a twelfth aspect, the invention concerns non-imidazole compounds which are analogous to those disclosed in WO 96/38141.

Thus, the invention is relative to compounds having the following formula (XII):

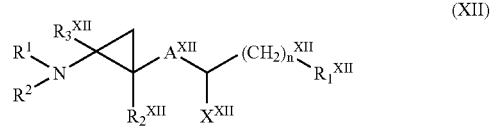

where $R^1$ and $R^2$ are as defined in reference to formula (A), where $R_2^{XII}$ is a hydrogen or a methyl or ethyl group;

$R_3^{XII}$ is a hydrogen or a methyl or ethyl group;

$n^{XII}$ is 0, 1, 2, 3, 4, 5, or 6; and $R_1^{XII}$ is selected from the group consisting of (a) C$_3$ to C$_8$ cycloalkyl; (b) phenyl substituted or not by one or more groups such as a halogen atom, a lower alkyl or cycloalkyl, a trifluoromethyl, aryl, alkoxy, α-alkyloxyalkyl, aryloxy, nitro, formyl, alkanoyl, aroyl, arylalkanoyl, amino, carboxamido, cyano, alkyloximino, alkylalkoximino, aryloximino, α-hydroxyalkyl, alkenyl, alkynyl, sulphamido, sulfamoyl, sulphonamido, carboxamide, carbonylcycloalkyl, alkylcarbonylalkyl, carbalkoxy, arylalkyl or oxime group, or two substituants taken together with the carbon atoms of the phenyl ring to which it is fused form 5- or 6-membered saturated or unsaturated ring or a benzene ring; (c) alkyl; (d) heterocyclic; (e) decahydronaphthalene; and (f) octahydroindene;

with the provisos that when $X^{XII}$ is H, $A^{XII}$ can be —CH$_2$CH$_2$—, —COCH$_2$—, —CONH—, —CON(CH$_3$)—, —CH=CH—, —C=C—, —CH$_2$—NH—, —CH$_2$—N(CH$_3$)—, —CH(OH)CH$_2$—, —NH—CH$_2$—, —N(CH$_3$)—CH$_2$—, —CH$_2$O—, —CH$_2$S—, or —NHCOO—;

when $X^{XII}$ is NH$_2$, NH(CH$_3$), N(CH$_3$)$_2$, OH, OCH$_3$, CH$_3$, SH or SCH$_3$; $A^{XII}$ can be —NHCO—, —N(CH$_3$)—CO—, —NHCH$_2$—, —N(CH$_3$)—CH$_2$—, —CH=CH—, —COCH$_2$—, —CH$_2$CH$_2$—, —CH(OH)CH$_2$—, or —C≡C—; and when R$_1^{XII}$ and X$^{XII}$ taken together denote a 5,6 or 6,6 saturated bicyclic ring structure X$^{XII}$ can be NH, O, or S.

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "substituted phenyl" as used herein refers to a phenyl group substituted by one or more groups such as alkyl, halogen, amino, methoxy, and cyano groups.

The term "bicyclic alkyl" as used herein refers to an organic compound having two ring structures connected to an alkyl group. They may or may not be the same type of ring and the rings may be substituted by one or more groups. Representative bicyclic alkyl groups include adamanthyl, decahydronaphthalene and norbornane.

The cyclopropane attached to the NR$^1$R$^2$ moiety is preferably in trans configuration.

More preferably, the present invention provides compounds of the general formula (XII):

where A$_{XII}$ is —CONH, —CH=CH—, —NHCOO—, or —C≡C—;

X$^{XII}$ is H or NH$_2$;

R$_2^{XII}$ and R$_3^{XII}$ are H;

n$^{XII}$ is 0, 1, 2 or 3;

R$_1^{XII}$ is cyclohexyl, phenyl or substituted phenyl.

In compounds (XII), A$^{XII}$ is especially —CH=CH— or —C≡C—;

R$_2^{XII}$, R$_3^{XII}$ and X$^{XII}$ are each especially a hydrogen atom; n$_{XII}$ is preferably 1 and R$_1^{XII}$ is especially an alkyl group.

R$^1$ and R$^2$ are preferably selected as above-indicated with reference to formula (A).

Representative example of compounds (XII) is compound 180.

According to a thirteenth aspect, the invention is directed to non-imidazole compounds analogous to those disclosed in WO 95/11894.

Thus, the present invention is relative to a sub-class of compounds (A) comprising compounds having the following formula (XIII):

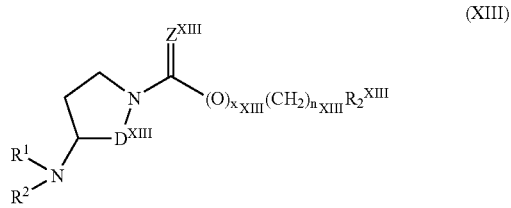

wherein R$^1$ and R$^2$ are as defined with reference to formula (A)

wherein D$^{XIII}$ is CH$_2$ or CH$_2$—CH$_2$, Z$^{XIII}$ represents sulfur (S) or oxygen (O), preferably O, X$_{XIII}$ is 0 or 1, n$_{XIII}$ is an integer from 0 to 6, and R$_2^{XIII}$ represents a substituted or unsubstituted linear chain or branched chain alkyl group of up to about 20 carbon atoms, a substituted or unsubstituted carbocyclic group of up to about 20 carbon atoms including mono and bicyclic moieties, and a substituted or an unsubstituted aryl group of up to about 20 carbon atoms, or any combination of above-mentioned groups, or salts thereof and with the substituents being represented by one or more groups such as a halogen atom, a lower alkyl or cycloalkyl, a trifluoromethyl, aryl, alkoxy, α-alkyloxyalkyl, aryloxy, nitro, formyl, alkanoyl, aroyl, arylalkanoyl, amino, carboxamido, cyano, alkyloximino, alkylalkoximino, aryloximino, α-hydroxyalkyl, alkenyl, alkynyl, sulphamido, sulfamoyl, sulphonamido, carboxamide, carbonylcycloalkyl, alkylcarbonylalkyl, carboalkoxy, arylalkyl or oxime group, or two substituants taken together with the carbon atoms of the phenyl ring to which it is fused form 5- or 6-membered saturated or unsaturated ring or a benzene ring.

In a specific embodiment, R$_2^{XIII}$ can represents a di-substituted methyl, such as but not limited to dicyclohexyl methyl (—CH(C$_6$H$_{11}$)$_2$), diphenyl methyl (—CH(C$_6$H$_5$)$_2$), and the like. If R$_2^{XIII}$ is tert-butyl, cyclohexyl, or dicyclohexylmethyl, X$_{XIII}$ or n$_{XIII}$ must not be 0. If R$_2^{XIII}$ is adamantane, the sum of x$_{XIII}$ and n$_{XIII}$ must be greater than 1.

In a preferred embodiment, D$^{XIII}$ is CH$_2$—CH$_2$, resulting in a piperidine ring structure. However, it is contemplated that D$^{XIII}$ can be CH$_2$, yielding a pyrrolidine ring structure. In yet another embodiment, D$^{XIII}$ can be (CH$_2$)$_3$, yielding a cycloheptimide (seven membered heterocycle with one nitrogen).

In a specific embodiment, a tetramethylene bound to the amide or carbamate group is used. Preferably a cyclic alkyl or aryl group is linked to the amide or carbamate via the straight chain alkyl group. In a specific embodiment, tetramethylene cyclohexane (cyclohexylbutyl) is bound to an amide. Although specific hydrophobic alkyl and aryl groups have been mentioned, one of ordinary skill in the art will recognize that there are many possible hydrophobic groups for use in the compounds of the invention. These fall within the scope of the instant invention.

Thus, R$_2^{XIII}$ can be one or more bulky substituent groups. As stated above, in a preferred aspect of the invention, the bulky substituents are removed from the amide or carbamate group on the piperidyl, by increasing n$_{XIII}$. In one embodiment, R$_2^{XIII}$ is CHR$_3^{XIII}$R$_4^{XIII}$, in which n$_{XIII}$ is 3 or 4 and R$_3^{XIII}$ and R$_4^{XIII}$ are cyclohexyl, phenyl, or the like. R$_3^{XIII}$ and R$_4^{XIII}$ can be the same group or different groups. In another embodiment, R$_2^{XIII}$ is decalin or adamantane or the like. If R$_2^{XIII}$ is adamantane, preferably n$_{XIII}$ is greater than 1, but the sum of x$_{XII}$ and n$_{XII}$ must be greater than 1.

As used herein, the phrase linear chain or branched chained alkyl groups of up to about 20 carbon atoms means any substituted or unsubstituted acyclic carbon-containing compounds, including alkanes, alkenes and alkynes. Examples of alkyl groups include lower alkyl, for example, methyl, ethyl, n-propyl, iso-propyl, n-butyl, iso-butyl or tert-butyl; upper alkyl, for example, octyl, nonyl, decyl, and the like; and lower alkylene, for example, ethylene, propylene, propyldiene, butylene, butyldiene, and the like. The ordinary skilled artisan is familiar with numerous linear and branched alkyl groups, which are with the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few.

As used herein, substituted and unsubstituted carbocyclic groups of up to about 20 carbon atoms means cyclic carbon-containing compounds, including but not limited to cyclopentyl, cyclohexyl, cycloheptyl, admantyl, and the like. Such cyclic groups may also contain various substituents in which one or more hydrogen atoms has been replaced by a functional group. Such functional groups include those described above, and lower alkyl groups as describe above. The cyclic groups of the invention may further comprise a heteroatom. For example, in a specific embodiment, $R_2^{XIII}$ is cyclohexanol.

As used herein, substituted and unsubstituted aryl groups means a hydrocarbon ring bearing a system of conjugated double bonds, usually comprising six or more even number of π(pi) electons. Examples of aryl groups include, by are not limited to, phenyl, naphthyl, anisyl, toluyl, xylenyl and the like. According to the present invention, aryl also includes heteroaryl groupss, e.g., pyrimidine or thiophene. These aryl groups may also be substituted with any number of a variety of functional groups. In addition to the functional groups described above in connection with substituted alkyl groups and carbocyclic groups, functional groups on the aryl groups can be nitro groups.

As mentioned above, $R_2^{XIII}$ can also represents any combination of alkyl, carbocyclic or aryl groups, for example, 1-cyclohexylpropyl, benzyl cyclohexylmethyl, 2-cyclohexylpropyl, 2,2-methylcyclohexylpropyl, 2,2-methylphenylpropyl, 2,2-methylphenylbutyl.

In a specific embodiment, $R_2$ represents cyclohexane, and $n_{XIII}=4$ (cyclohexylvaleroyl). In another specific embodiment, $R_2^{XIII}$ represents cinnamoyl.

Particularly preferred are compounds (XIII) wherein $Z^{XIII}$ is an oxygen atom and wherein $x_{XIII}$ is 0 or 1, $n_{XIII}$ is an integer from 0 to 6, more preferably $n_{XIII}=3–6$, and most preferably $n_{XIII}=4$, and $R_2^{XIII}$ is as defined above. Examples of preferred alkyl groups for $R_2^{XIII}$ include but are not limited to cyclopentyl, cyclohexyl, admantane methylene, dicyclohexyl methyl, decanyl and t-butyryl and the like. Examples of preferred aryl and substituted aryl groups include but are not limited to phenyl, aryl cyclohexyl methyl and the like.

Preferred $R^1$ and $R^2$ are selected as indicated with reference to formula (A).

Representative examples are compounds 123 and 176.

According to a fourteenth aspect, the present invention is directed to compounds analogous to those disclosed in WO 93/12107.

Thus, a sub-class of compounds (A) of the invention concerns compounds having the following formula (XIV)

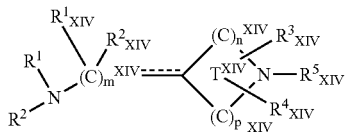

(XIV)

wherein $R^1$ and $R^2$ are as defined in reference of formula (A);

(A) $m_{XIV}$ is an integer selected from the group consisting of: 1 and 2;

(B) $n_{XIV}$ and $p_{XIV}$ are intergers and are each independently selected from the group consisting of: 0, 1, 2, 3, and 4 such that the sum of $n_{XIV}$ and $p_{XIV}$ is 4 and $T^{XIV}$ is a 6-membered ring;

(C) $R^3_{XIV}$ and $R^4_{XIV}$ are each independently bound to the same or different carbon atom of ring $T^{XIV}$ such that there is only one $R^3_{XIV}$ group and one $R^4_{XIV}$ group in ring $T^{XIV}$, and each $R^1_{XIV}$, $R^2_{XIV}$, $R^3_{XIV}$ and $R^4_{XIV}$ is independently selected from the group consisting of:

(1) H;
(2) $C_1$ to $C_6$ akyl; and
(3) —(CH$_2$)$_{qXIV}$—R$^6_{XIV}$ wherein $q_{XIV}$ is an integer of: 1 to 7, and $R^6_{XIV}$ is selected from the group consisting of: phenyl, substituted phenyl, —OR$^7_{XIV}$, —C(O)OR$^7_{XIV}$, —C(O)R$^7_{XIV}$, —OC(O)R$^7_{XIV}$, —C(O)NR$^7_{XIV}$R$^8_{XIV}$, CN and —SR$^7_{XIV}$ wherein R$^7_{XIV}$ and R$^8_{XIV}$ are as defined below, and wherein the substituents on said substituted phenyl are each independently selected from the group consisting of: —OH, —O—(C$_1$ to C$_6$)alkyl, halogen, C$_1$ to C$_6$ alkyl, —CF$_3$, —CN, and —NO$_2$, and wherein said substituted phenyl contains from 1 to 3 substituents;

(D) $R^5_{XIV}$ is selected from the group consisting of:
(1) H;
(2) $C_1$ to $C_{20}$ alkyl;
(3) $C_3$ to $C_6$ cycloalkyl;
(4) —C(O)OR$^{7'}_{XIV}$; wherein R$^{7'}_{XIV}$ is the same as R$^7_{XIV}$ defined below except that R$^{7'}_{XIV}$ is not H;
(5) —C(O)R$^{7'}_{XIV}$;
(6) —C(O)NR$^{7'}_{XIV}$R$^8_{XIV}$;
(7) allyl;
(8) propargyl; and
(9) —(CH$_2$)$_q$—R$^6_{XIV}$ wherein $q_{XIV}$ and R$^6_{XIV}$ are as defined above, and when $q_{XIV}$ is equal to 1, then R$^6_{XIV}$ is not OH or SH;

(E) $R^7_{XIV}$ and $R^8_{XIV}$ are each independently selected from the group consisting of: H, $C_1$ to $C_6$ alkyl, and $C_3$ to $C_6$ cycloalkyl;

(F) the dotted line (--------) represents a double bond that is optionally present when $m_{XIV}$ is 1, and $n_{XIV}$ is not 0, and p is not 0 (i.e., the nitrogen in the ring is not bound directly to the carbon atom bearing the double bond), and when said double bond is present then $R^2_{XIV}$ is absent; and (G) when $m_{XIV}$ is 2, each $R^1_{XIV}$ is the same or different substituent for each $m_{XIV}$, and each $R^2_{XIV}$ is the same or different substituent for each $m_{XIV}$, and at least two of the substituents $R^1_{XIV}$ and/or $R^2_{XIV}$ are H.

Those skilled in the art will appreciate that the total number of substituents on each of the —(C)$_n^{XIV}$— and —(C)$_p^{XIV}$— groups is two, and that such substituents are independently selected from the group consisting of hydrogen, $R^3_{XIV}$ and $R^4_{XIV}$ such that there is a total of only one $R^3_{XIV}$ and one $R^4_{XIV}$ substituent in ring $T^{XIV}$.

As used herein the following terms have the following meanings unless indicated otherwise:

alkyl—represents a straight or branched, saturated hydrocarbon chain having from 1 to 20 carbon atoms;

cycloalkyl—represents a saturated carbocyclic ring having from 3 to 6 carbon atoms;

halogen (halo)—represents fluoro, chloro, bromo or iodo.

Preferably, for compounds of formula (XIV) m is 1; $R^5_{XIV}$ is selected from the group consisting of H and $C_1$ to $C_{15}$ alkyl; and $R^1_{XIV}$ to $R^4_{XIV}$ are each independently selected from the group consisting of: H, $C_1$ to $C_6$ alkyl, and —(CH$_2$)$_{qXIV}$—R$^6_{XIV}$ wherein R$^6_{XIV}$ is phenyl. Most preferably, $R^5_{XIV}$ is selected from the group consisting of H and $C_1$ to $C_6$ alkyl with H and methyl being even more preferable; and $R^3_{XIV}$ and $R^4_{XIV}$ are each independently selected from the group consisting of: H and methyl.

Representative compounds of this invention include compounds of the formula:

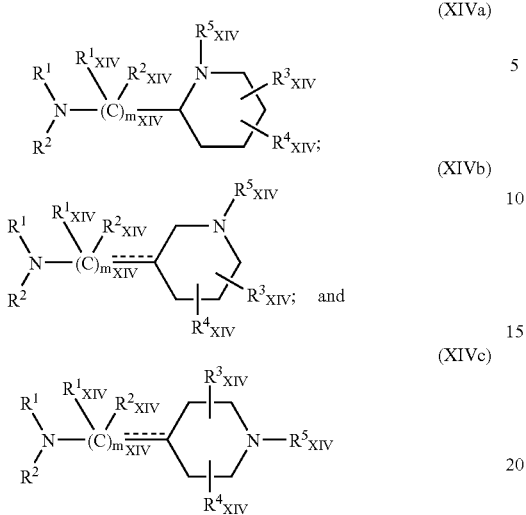

For formula (XIVa), (XIVb) or (XIVc), $R^5{}_{XIV}$ is preferably H or CH$_3$; $R^3{}_{XIV}$ and $R^4{}_{XIV}$ are preferably each an hydrogen atom.

Preferred $R^1$ and $R^2$ are as specified for formula (A).

According to a fifteenth aspect, the invention is directed to compounds analogous to those disclosed in WO 93/12108.

Thus, the invention concerns compounds having the following formula (XV):

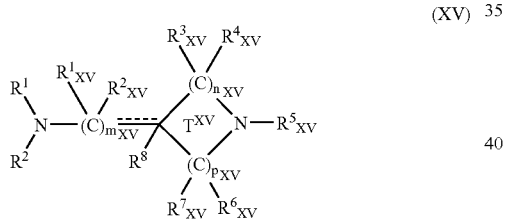

wherein $R^1$ and $R^2$ are as defined in reference to formula (A)

(A) $m_{XV}$ is an integer selected from the group consisting of: 0, 1, and 2;

(B) $n_{XV}$ and $p_{XV}$ are integers and are each independently selected from the group consisting of: 0, 1, 2, and 3 such that the sum of $n_{XV}$ and $p_{XV}$ is 2 or 3 such that when the sum of $n_{XV}$ and $p_{XV}$ is 2, $T^{XV}$ is a 4-membered ring and when the sum of $n_{XV}$ and $p_{XV}$ is 3, $T^{XV}$ is a 5-membered ring;

(C) each $R^1{}_{XV}$, $R^2{}_{XV}$, $R^3{}_{XV}$, $R^4{}_{XV}$, $R^6{}_{XV}$, $R^7{}_{XV}$ and $R^8{}_{XV}$ is independently selected from the group consisting of:
(1) H;
(2) $C_1$ to $C_6$ alkyl;
(3) $C_3$ to $C_6$ cycloalkyl; and
(4) —(CH$_2$)$_q{}^{XV}$—$R^9{}_{XV}$ wherein $q_{XV}$ is an integer of: 1 to 7, and $R^9{}_{XV}$ is selected from the group consisting of: phenyl, substituted phenyl, —OR$^{10}{}_{XV}$, —C(O)OR$^{10}{}_{XV}$, —C(O)R$^{10}{}_{XV}$, —OC(O)R$^{10}{}_{XV}$, —C(O)NR$^{10}{}_{XV}$R$^{11}{}_{XV}$, CN and —SR$^{10}{}_{XV}$ wherein $R^{10}{}_{XV}$ and $R^{11}{}_{XV}$ are as defined below, and wherein the substituents on said substituted phenyl are each independently selected from the group consisting of: —OH, —O—($C_1$ to $C_6$) alkyl, halogen, $C_1$ to $C_6$ alkyl, —CF$_3$, —CN, and —NO$_2$, and wherein said substituted phenyl contains from 1 to 3 substituents; examples of —(CH$_2$)$_{qXV}$—R$^9{}_{XV}$ include benzyl, substituted benzyl and the like, wherein the substitutents on the substituted benzyl are as defined above for said substituted phenyl;

(D) $R^5{}_{XV}$ is selected from the group consisting of:
(1) H;
(2) $C_1$ to $C_{20}$ alkyl;
(3) $C_3$ to $C_6$ cycloalkyl;
(4) —C(O)OR$^{10'}{}_{XV}$; wherein R$^{10'}{}_{XV}$ is the same as R$^{10}{}_{XV}$ defined below except that R$^{10'}{}_{XV}$ is not H;
(5) —C(O)R$^{10}{}_{XV}$;
(6) —C(O)NR$^{10}{}_{XV}$R$^{11}{}_{XV}$;
(7) allyl;
(8) propargyl; and
(9) —(CH$_2$)$_q{}^{XV}$—R$^9{}_{XV}$, wherein $q_{XV}$ and R$^9{}_{XV}$ are as defined above with the proviso that when $q_{XV}$ is 1 then R$^9{}_{XV}$ is not —OH or —SH;

(E) R$^{10}{}_{XV}$ and R$^{11}{}_{XV}$ are each independently selected from the group consisting of: H, $C_1$ to $C_6$ alkyl, and $C_3$ to $C_6$ cycloalkyl; and, for the substituent —C(O)NR$^{10}{}_{XV}$R$^{11}{}_{XV}$, R$^{10}{}_{XV}$ and R$^{11}{}_{XV}$, together with the nitrogen to which they are bound, can form a ring having 5, 6, or 7 atoms;

(F) the dotted line (-----) represents a double bond that is optionally present when $m_{XV}$ is 1, and $T^{XV}$ is a 5-membered ring, and $n_{XV}$ is not 0, and $p_{XV}$ is not 0 (i.e., the nitrogen in the ring is not bound directly to the carbon atom bearing the double bond), and when said double bond is present then R$^2{}_{XV}$ and R$^8{}_{XV}$ are absent;

(G) when $m_{XV}$ is 2, each R$^1{}_{XV}$ is the same or different substituent for each $m_{XV}$, and each R$^2{}_{XV}$ is the same or different substituent for each $m_{XV}$;

(H) when $n_{XV}$ is 2 or 3, each R$^3$XV is the same or different substituent for each $n_{XV}$, and each R$^4{}_{XV}$ is the same or different substituent for each $n_{XV}$; and (I) when $p_{XV}$ is 2 or 3, each R$^6{}_{XV}$ is the same or different substituent for each p, and each R$^7{}_{XV}$ is the same or different substituent for each $p_{XV}$.

As used herein the following terms have the following meanings unless indicated otherwise:

alkyl—represents a straight or branched, saturated hydrocarbon chain having from 1 to 20 carbon atoms;

cycloalkyl—represents a saturated carbocyclic ring having from 3 to 6 carbon atoms; and halogen (halo)—represents fluoro, chloro, bromo or iodo.

Preferably, for compounds of formula (XV) $m_{XV}$ is 0 or 1; R$^5$XV is selected from the group consisting of H and $C_1$ to $C_{20}$ alkyl; and R$^1{}_{XV}$ to R$^4{}_{XV}$, and R$^6{}_{XV}$ to R$^8{}_{XV}$ are each independently selected from the group consisting of: H, $C_1$ to $C_6$ alkyl, and —(CH$_2$)$_{XV}$—R$^9{}_{XV}$ wherein R$^9{}_{XV}$ is phenyl. Most preferably, R$^5{}_{XV}$ is selected from the group consisting of H and methyl; and R$^1{}_{XV}$, R$^2$XV, R$^3{}_{XV}$, R$^4{}_{XV}$, R$^6$XV, R$^7{}_{XV}$, and R$^8{}_{XV}$ are each independently selected from the group consisting of: H, methyl, ethyl, pentyl, benzyl, and 2-phenylethyl.

Representative compounds of this invention include compounds of the formula:

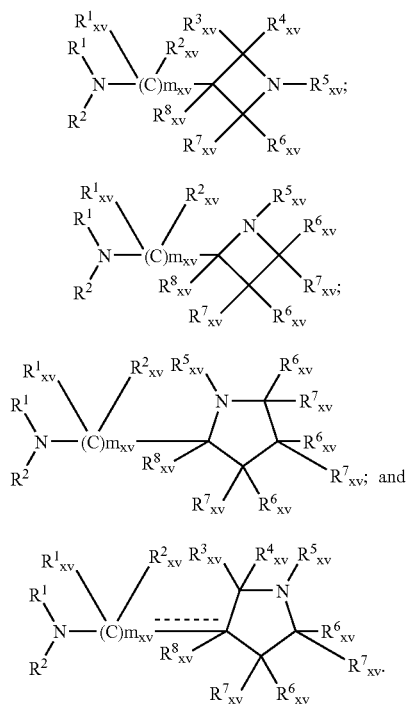

(XVa)

(XVb)

(XVc)

(XVd)

wherein $m_{XV}$ and $R^1_{XV}$ to $R^8_{XV}$ are as defined for formula (XV)

Compounds (XVc) or (XVd) are preferred.

Representative compounds (XVa) to (XVd) are those wherein $R^5_{XV}$ is H or CH$_3$.

Preferably, only one or two of substituents $R^3_{XV}$, $R^4_{XV}$, $R^6_{XV}$, $R^7_{XV}$, $R^8_{XV}$ is different from H and represents especially CH$_3$.

$R^1$ and $R^2$ are preferably selected as indicated in reference to formula (A).

According to a sixteenth aspect, the invention is directed to compounds analogous to those disclosed in WO 92/15567.

Thus, the invention is relative to a sub-class of compounds (A) consisting of compounds having the following formula (XVI)

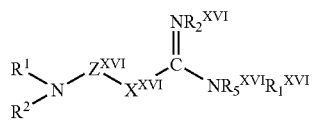

(XVI)

wherein $R^1$ and $R^2$ are as defined in reference to formula (A)

$Z^{XVI}$ is a group of the formula $(CH_2)_{m_{XVI}}$ wherein $m_{XVI}$=1–5 or a group of the formula:

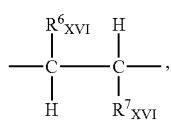

, wherein $R^6_{XVI}$=(C$_1$–C$_3$)alkyl $R^7_{XVI}$=(C$_1$–C$_3$)alkyl wherein $Z^{XVI}$ may optionally comprise other substituents selected such that the activity of the derivative is not negatively affected, $X^{XVI}$ represents S, NH or CH$_2$ $R^1_{XVI}$ represents hydrogen, (C$_1$–C$_3$)alkyl-, aryl(C$_1$–C$_{10}$)alkyl, wherein aryl may optionally be substituted, aryl, (C$_5$–C$_7$)cycloalkyl(C$_1$–C$_{10}$)alkyl-, or a group of the formula:

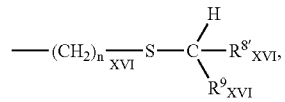

wherein $n_{XVI}$=1–4, $R^8_{XVI}$ is aryl, aryl(C$_1$–C$_{10}$)alkyl-, (C$_5$–C$_7$)cycloalkyl- or (C$_5$–C$_7$) cycloalkyl(C$_1$–C$_{10}$)alkyl-, and $R^9_{XVI}$ is hydrogen, (C$_1$–C$_{10}$)alkyl- or aryl; $R_2^{XVI}$ and $R_5^{XVI}$ represent hydrogen, (C$_1$–C$_3$)alkyl-, aryl or arylalkyl-, wherein aryl may optionally be substituted; wherein aryl is phenyl, substituted phenyl, naphthyl, substituted napththyl, pyridyl or substituted pyridyl;

$R_2^{XVI}$ and $R_5^{XV}$ are preferably a hydrogen atom.

$m_{XVI}$ is preferably 2 or 3

$X^{XVI}$ is preferably S or NH $R_1^{XVI}$ is preferably selected from H or an optionally substituted aryl.

Preferred $R^1$ and $R^2$ are selected as specified for formula A.

According to a seventeenth aspect, a sub-class of compounds (A) of the invention comprises compounds having the following formula (XVII), which can be considered as analogous to those disclosed in EP 680 960:

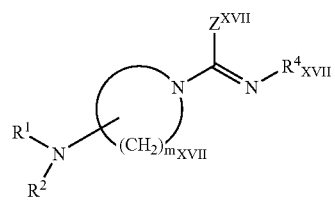

XVII

Wherein $m_{XVII}$ represents an integer of from 4 to 6.

$R^4_{XVII}$ represents a hydrogen atom, a linear or branched alkyl group, a cycloalkyl group, a cycloalkylalkyl group, a substituted or unsubstituted aryl group or a substituted or unsubstituted aralkyl group; and $Z^{XVII}$ represents $R^5_{XVII}$ or $A^{XVII}$—$R^6_{XVII}$, wherein $A^{XVII}$ represents S or O, $R_5^{XVII}$ represents a hydrogen atom, a lower alkyl group, a substituted or unsubstituted aryl group or a substituted or unsubstituted aralkyl group, and $R_6^{XVII}$ represents a lower alkyl group, a lower alkenyl group, a lower alkynyl group or a substituted or unsubstituted aralkyl group;

The lower alkyl groups are preferably linear or branched alkyl groups having 1 to 6 carbon atoms. Specific examples thereof include methyl, ethyl, n-propyl, iso-propyl, n-butyl, iso-butyl, sec-butyl, tert-butyl, n-pentyl and n-hexyl groups.

The linear or branched alkyl groups are preferably those having 1 to 8 carbon atoms. Specific examples thereof include methyl, ethyl, n-propyl, iso-propyl, n-butyl, isobutyl, sec-butyl, tert-butyl, n-pentyl, n-hexyl, 1,1-dimethylpropyl, 1,2-dimethylpropyl and 1,2,2-trimethylpropyl groups.

The cycloalkyl groups are preferably those having 3 to 10 carbon atoms. The cycloalkyl groups include not only monocycloalkyl groups (for example, cyclopentyl, cyclohexyl and cycloheptyl) but also polycycloalkyl groups (for example, bicycloalkyl and tricycloalkyl). Examples of the bicycloalkyl groups include norbornyl (for example, exo-2-norbornyl and endo-2-norbornyl), 3-pinanyl and bicyclo [2.2.2]oct-2-yl groups, while examples of the tricycloalkyl groups include adamantyl groups (for example, 1-adamantyl and 2-adamantyl). Such a cycloalkyl group may be substituted by alkyl group(s), etc.

The cycloalkylalkyl groups are preferably those composed of a cycloalkyl group having 3 to 10 carbon atoms with a linear or branched alkyl group having 1 to 3 carbon atoms. Specific examples thereof include 1-cyclohexylethyl and 1-cyclopropylethyl groups.

The lower alkenyl groups are preferably linear or branched alkenyl groups having 3 to 6 carbon atoms. Specific examples thereof include allyl, 1-methyl-2-propenyl, 2-methyl-2-propenyl, cis-2-butenyl, trans-2-butenyl and 3-methyl-2-butenyl groups.

The lower alkynyl groups are preferably those having 3 to 6 carbon atoms. A specific example thereof includes a 2-propynyl group.

The substituted aryl groups are preferably phenyl and naphthyl groups which may be substituted by halogen atoms and trifluoromethyl, lower alkyl, lower alkoxy, lower alkylthio, cyano and nitro groups.

Specific examples thereof include phenyl, 1-naphthyl, 2-chlorophenyl, 3-chlorophenyl, 4-chlorophenyl, 4-trifluoromethylphenyl, 3-fluorophenyl, 4-fluorophenyl, 2-methoxyphenyl, 4-methoxyphenyl, 2-tolyl and 3-tolyl groups.

The aralkyl groups are preferably benzyl, diarylmethyl and trityl groups.

The substituted aralkyl groups are preferably arylalkyl groups is composed of a phenyl or naphthyl group, which may be substituted by halogen atoms and trifluoromethyl, lower alkyl, lower alkoxy, lower alkylthio, cyano and nitro groups, and a linear or branched alkyl group having 1 to 4 carbon atoms.

Specific examples thereof include benzyl, α-methylbenzyl, phenethyl, 3-phenylpropyl, 4-phenylbutyl, 4-chlorobenzyl, 4-fluorobenzyl, 4-methoxybenzyl, 4-chloro-α-methylbenzyl, 4-fluoro-αmethylbenzyl and 4-methoxy-α-methylbenzyl groups.

Among the compounds represented by the general formula (XVII) preferable examples include those wherein:
  $m^{XVII}$ is from 4 to 6;
  $R^4_{XVII}$ is a hydrogen atom; a linear or branched alkyl group having 1 to 8 carbon atoms, a cycloalkyl group having 3 to 10 carbon atoms, a cycloalkylalkyl group composed of a cycloalkyl moiety having 3 to 10 carbon atoms and an alkyl moiety having 1 to 3 carbon atoms, a substituted or unsubstituted aryl group or a substituted or unsubstituted aralkyl group carrying an alkyl moiety having 1 to 4 carbon atoms;
  $R^5_{XVII}$ is a hydrogen atom, an alkyl group having 1 to 6 carbon atoms, a substituted or unsubstituted aryl group or a substituted or unsubstituted aralkyl group carrying an alkyl moiety having 1 to 4 carbon atoms; and
  $R^6_{XVII}$ is an alkyl group having 1 to 6 carbon atoms, an alkenyl group having 3 to 6 carbon atoms, an alkynyl group having 3 to 6 carbon atoms or a substituted or unsubstituted aryl group.

Preferable examples of the compounds represented by the general formula (XVII) are those satisfying the following requirements:

(1) A compound wherein $m^{XVII}$ is 5 and $R^1$, $R^2$ and $R^3$ are each a hydrogen atom.

A compound wherein $R^4_{XVII}$ is a cycloalkyl group, such as monocycloalkyl, bicycloalkyl and tricycloalkyl groups. A preferable example of the monocycloalkyl group is a cyclohexyl group. A preferable example of the bicycloalkyl group is a norbornyl group, more preferably a 2-exo-norbornyl group. A preferable example of the tricycloalkyl group is an adamantyl group, more preferably a 1-adamantyl group.

(3) A compound wherein $R^4_{XVII}$ is a substituted or unsubstituted phenyl group or a substituted or unsubstituted phenylalkyl group.

(4) A compound wherein $R^5_{XVII}$ is a hydrogen atom.

(5) A compound wherein $A^{XVII}$ is S and $R^6_{XVII}$ is a lower alkyl group.

(6) A compound wherein a lower alkyl group is a methyl group.

$R^1$ and $R^2$ are preferably selected as specified for the formula (A).

According to a eighteenth aspect, the invention is directed to non imidazole compounds having the following formula (XVIII), analogous to those disclosed in Van der Goot et al. (Eur. J. Med. Chem. (1992) 27, 511–517):

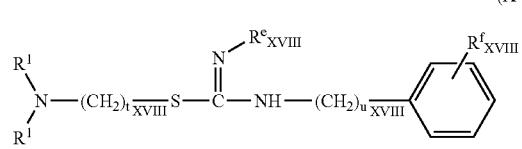

(XVIII)

in which:
  $R^1$ and $R^2$ are as defined with reference to formula (A);
  $R^e_{XIII}$ is H, alkyl or cycloalkyl;
  $R^f_{XVIII}$ is H or halogen, in particular Cl, F, Br, or an alkyl;
  $t_{XVIII}$ is 1 to 3;
  $u_{XVIII}$ is 1 to 4.

Preferred groups $R^1$ and $R^2$ are as defined with reference to formula (A).

Representative example is compound 122 and 167.

According to the invention, the W residue as defined in formula (A) and in particular as illustrated by formulae (I) to (XVIII), preferably contains no imidazole moiety attached in 4(5)-position and more preferably W contains no imidazole moiety.

The compounds according to the invention may be prepared according to one of the following schemes:

More specifically, compounds of formula (I) can be obtained by the schemes 1 to 5:

In these schemes, $R^1$, $R^2$, $R^3$, X and n are as defined in general formula (I).

Me and Et are intended to mean methyl and ethyl.

SCHEME 1 (methods A, B, C, D, H and K):
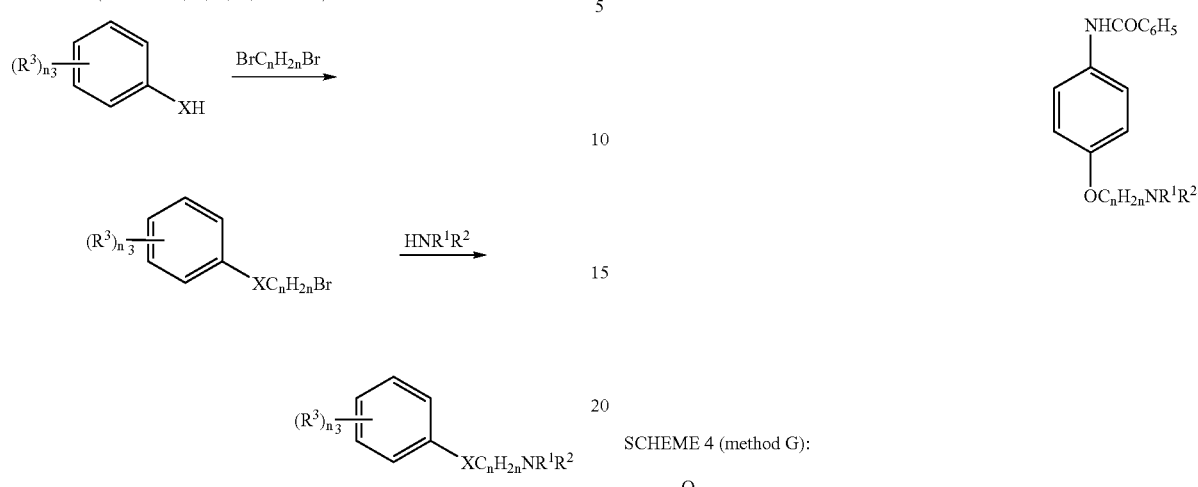
SCHEME 2 (methods F and L):
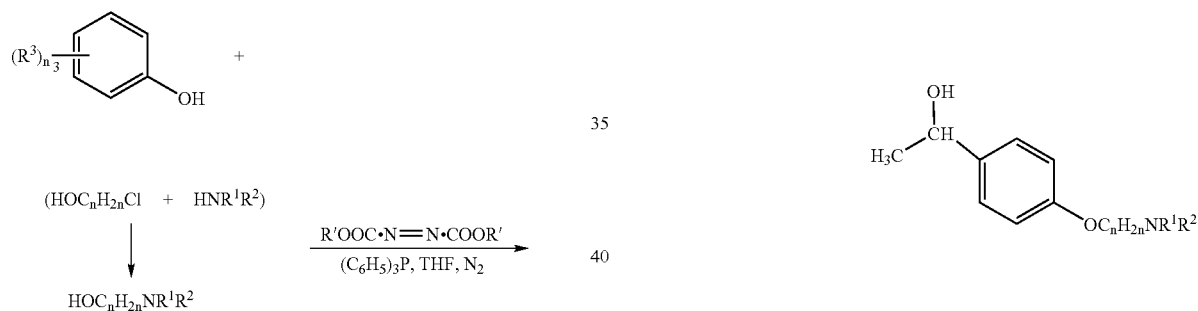
SCHEME 3 (method E):
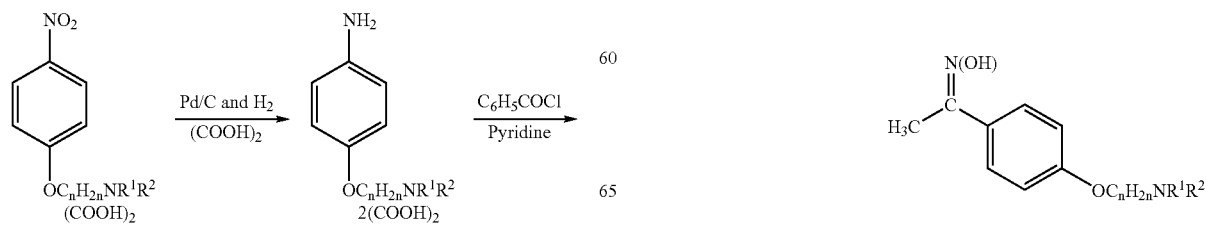
SCHEME 4 (method G):
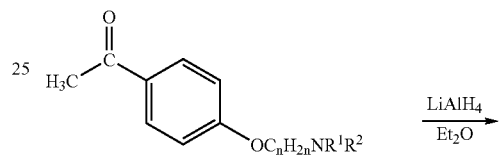
SCHEME 5 (method J):
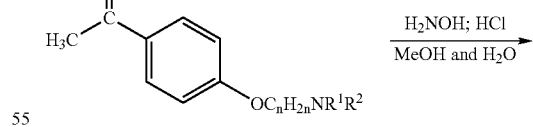

SCHEME 6:
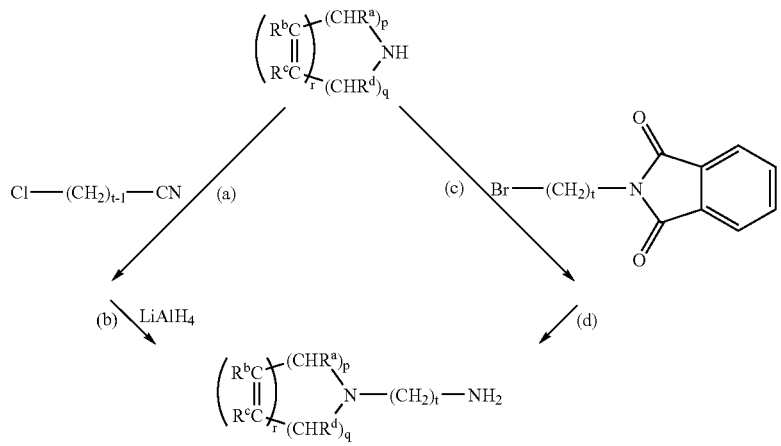
For example: (a) KI, K₂CO₃, EtOH, 6 h, reflux; (b) THF, 3 h, reflux.
(c) KI, K₂CO₃, EtOH, 3 h, 60 °C; 6N HCl, 2h, 100 °C.
$R^{a-d}$ = H or lower alkyl
p, q, r = 0–3 (independently)
t = 2–8
SCHEME 7:
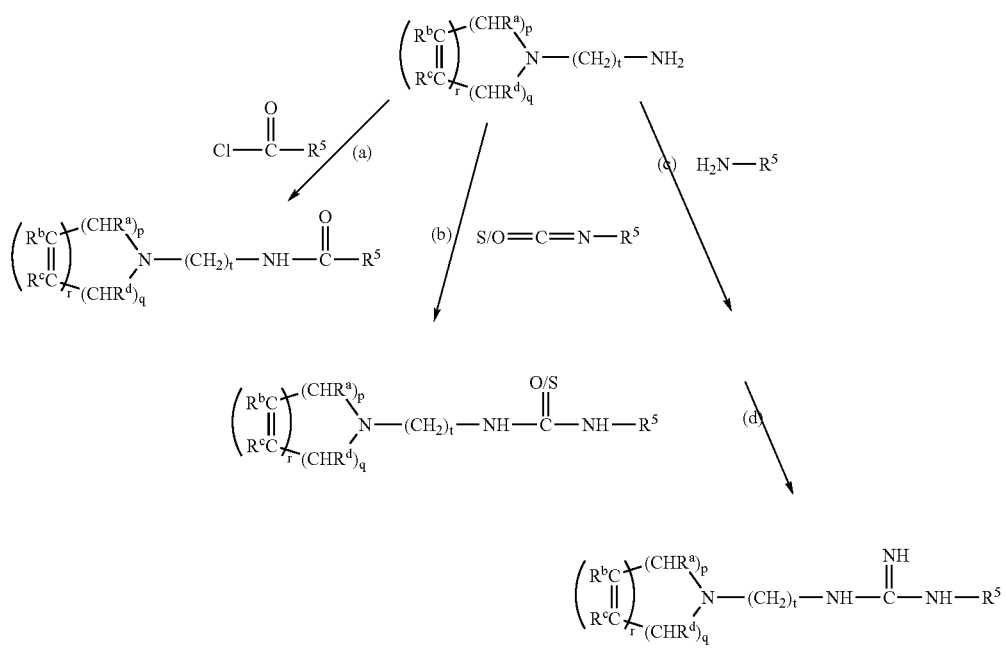
$R^{a-d}$ = H or lower alkyl; $R^5$ = alkyl, cycloalkyl, or aryl.
p, q, r = 0–3 (independently); t = 2–5.

For example: (a) dioxane/H$_2$O (1+1), 4 h, 0° C.; (b) acetonitrile, 5 min, r.t.; (c) N-Boc-diphenylimido carbonate, 10 h, reflux; (d) 1 N HCl, 0.5 h, reflux.

SCHEME 8:

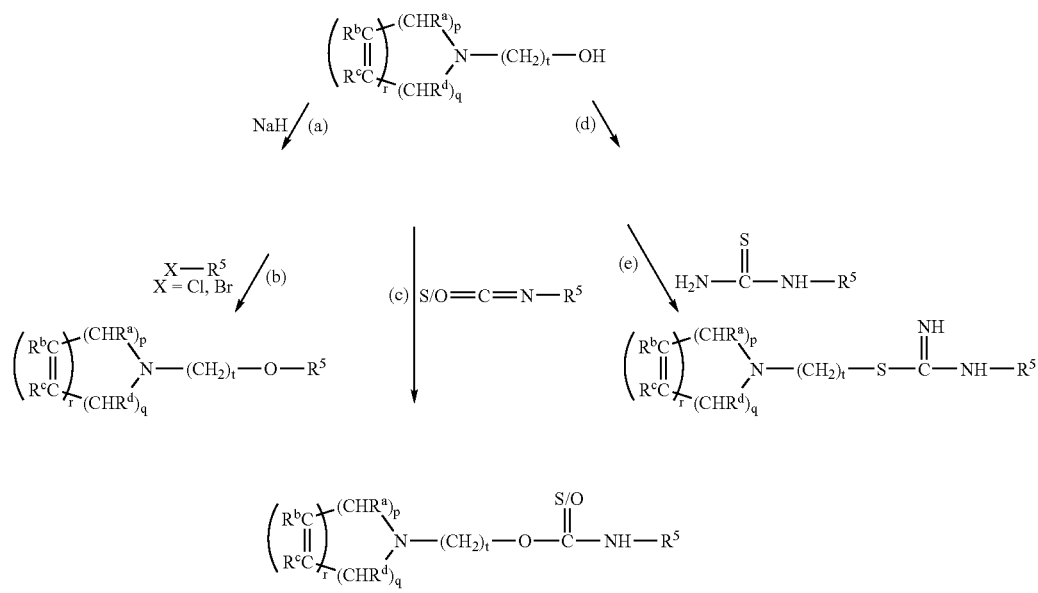

R$^{a-d}$=H or lower alkyl; R$^5$=alkyl, cycloalkyl, or aryl.
p, q, r=0–3 (independently); t=2–5.

For example: (a) toluene, 12 h, r.t.; (b) toluene, tetrabutylammonium iodide, 15-crown-5, 12 h, 80° C.; (c) acetonitrile, 4 (d) thionyl chloride, THF, 12 h, 50° C.; (e) K$_2$CO$_3$, H$_2$O, EtOH, 2 days, reflux.

SCHEME 9:

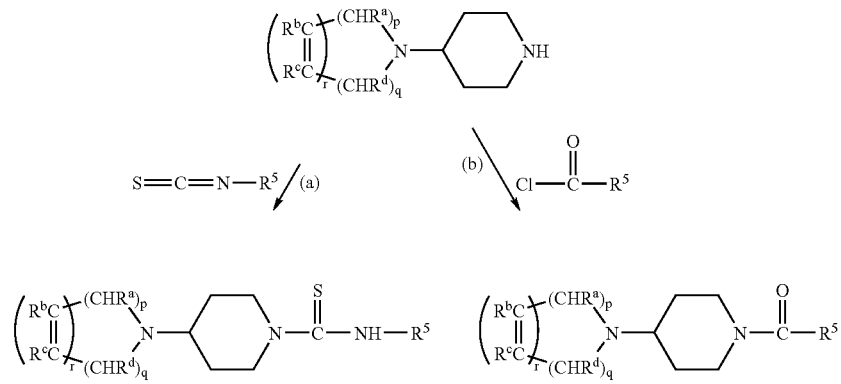

R$^{a-d}$=H or lower alkyl; R$^5$=alkyl, cycloalkyl, or aryl.
p, q, r=0–3 (independently).

For example: (a) diethyl ether, 2 h, r.t.; (b) dioxane/H$_2$O (1+1), 4 h, 0° C.

For example: (a) acetone, triethylamine, 8 h, 50° C.; (b) NaH, MeOH, DMF, 6 h, 80° C.
SCHEME 10:
SCHEME 11:
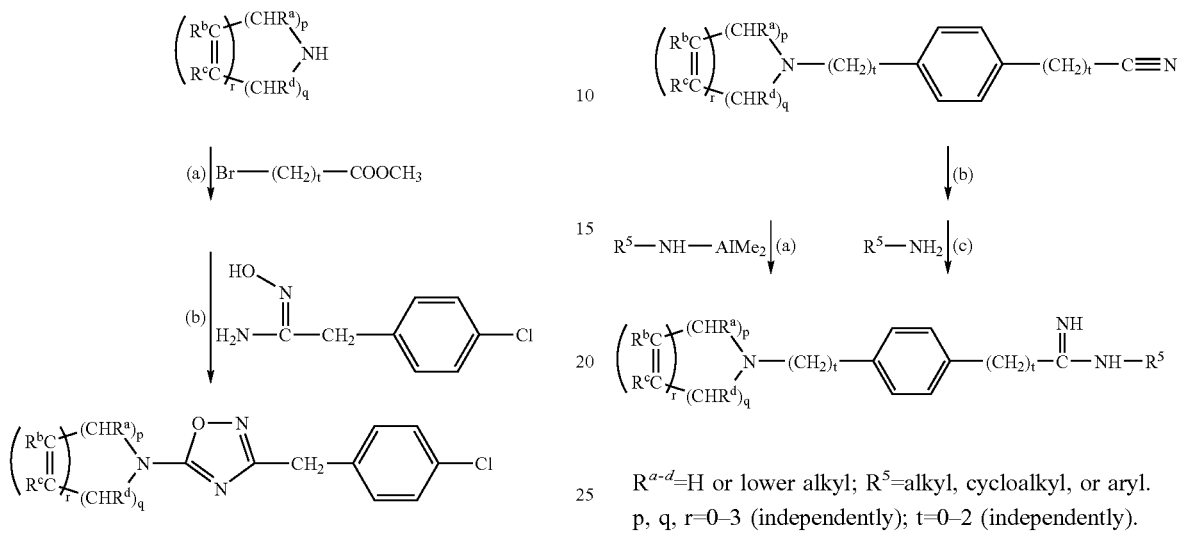
$R^{a-d}$=H or lower alkyl.
p, q, r=0–3 (independently); t=2–5.
$R^{a-d}$=H or lower alkyl; $R^5$=alkyl, cycloalkyl, or aryl.
p, q, r=0–3 (independently); t=0–2 (independently).
For example: (a) toluene, 100° C., nitrogen atmosphere, 12 h; (b) MeOH, $SOCl_2$; (c) triethylamine, MeOH.
SCHEME 12
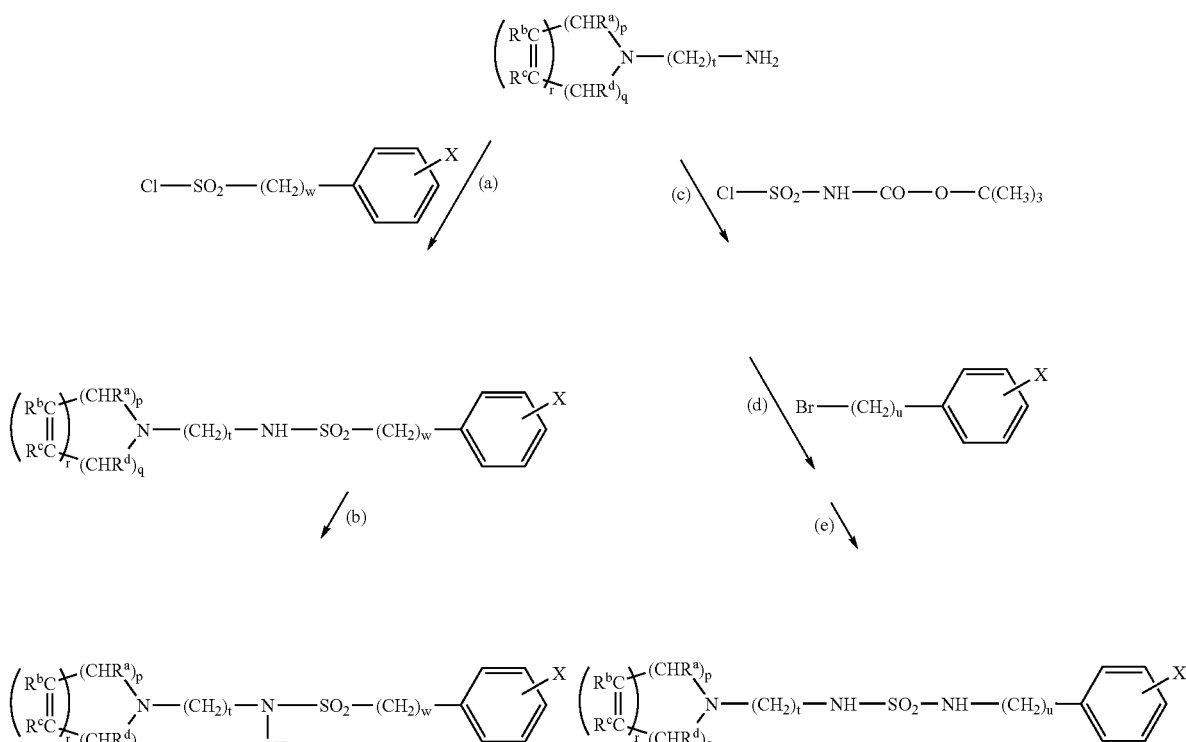

$R^{a-d}$=H or lower alkyl; X=Cl, Br, etc.
p, q, r=0–3 (independently); t=2–5; u=1–5; w=0–2.

For example: (a) triethylamine, $CH_2Cl_2$, 24 h, r.t; (b) N,N, N',N'-tetramethylazodicarboxamide, tributylphosphine, MeOH, benzene, 24 h, r.t.; (c) triethylamine, $CH_2Cl_2$, argon atmosphere, 0° C., 18 h; (d) NaH, DMF, argon atmosphere, −15° C.; (e) 1N HCl, MeOH, 18 h, reflux.

SCHEME 13

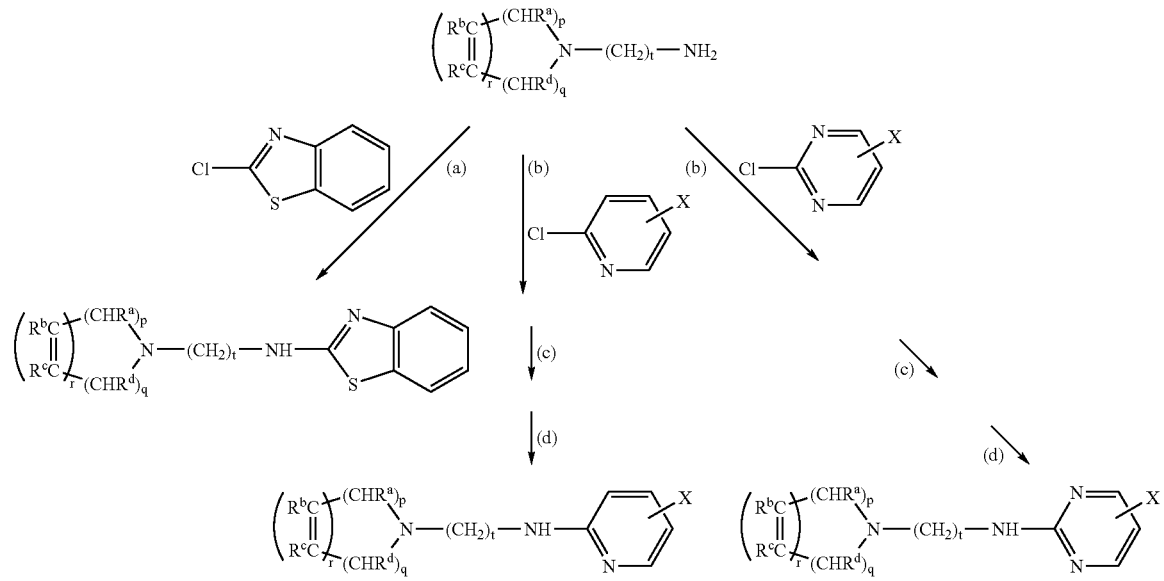

$R^{a-d}$=H or lower alkyl; X=$NO_2$, $NH_2$, $OCH_3$, etc.
p, q, r=0–3 (independently); t=2–6.

For example: (a) triethylamine, $CH_2Cl_2$, 24 h, 50° C.; (b) triethylamine, KI, EtOH, 6 h, reflux; (c) thionyl chloride, THF, 2 h, 0° C.; (d) $K_2CO_3$, KI, EtOH, 6 h, reflux.

SCHEME 14:

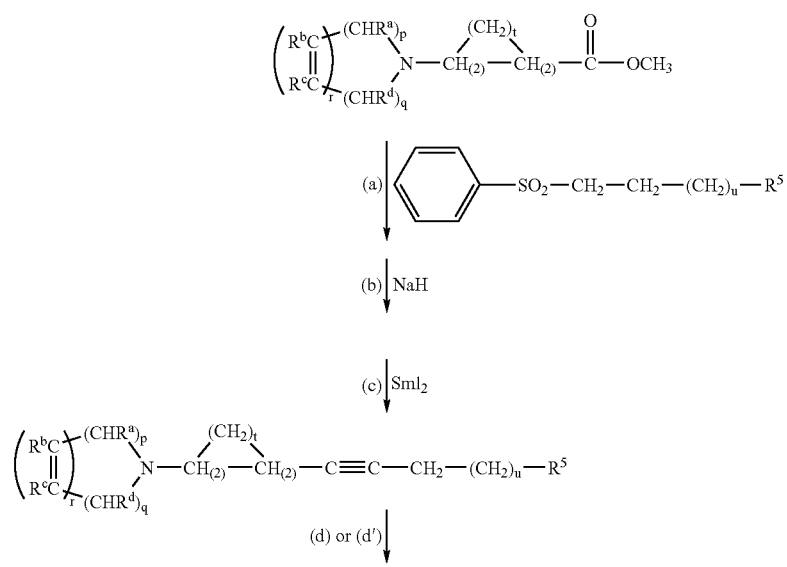

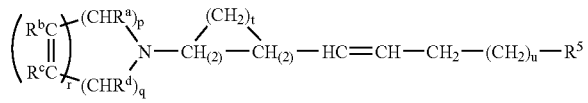

(e) ↓

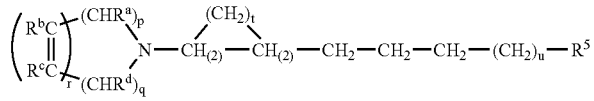

$R^{a-d}$=H or lower alkyl; $R^5$=alkyl, cycloalkyl, or aryl.
p, q, r=0–3 (independently); t, u=0–3.

For example: (a) n-BuLi, −78° C.; (b) THF, ClP(O)OEt$_2$; (c) THF, 4 mole % HMPA; (d) H$_2$, quinoline, ethyl acetate (cis); (d') Na/NH$_3$ (trans); (e) H$_2$, Pd (black), MeOH.

Detailed synthesis procedures are given in the examples.

The compounds of formula (A) according to the invention have antagonistic and/or agonistic properties at the histamine H$_3$-receptors. They affect the synthesis and release of histamine monoamines or neuropeptides in brain and peripheral tissues.

This property makes the compounds of the invention useful derivatives in human or veterinary medicine.

Their therapeutical applications are those known for H$_3$-antagonist and/or agonist compounds and especially relate to the central nervous system disorders.

Regarding antagonistic activity, the compounds according to the invention can be used in the treatment of Alzheimer disease, mood and attention alterations, cognitive deficits in psychiatric pathologies, obesity, vertigo and motion sickness.

Regarding agonistic activity, the compounds according to the invention can be used in the treatment of various allergic and inflammatory diseases and as a sedative agent.

Therefore, the compounds of formula (A) according to the invention are advantageously used as active ingredient of medicaments which act as ligand for H$_3$-receptors of histamine and in particular as an antagonist and/or agonist of H$_3$-receptors of histamine.

The present invention is also directed to the use of at least one following compounds
1-(5-phenoxypentyl)-piperidine
1-(5-phenoxypentyl)-pyrrolidine
N-methyl-N-(5-phenoxypentyl)-ethylamine
1-(5-phenoxypentyl)-morpholine
N-(5-phenoxypentyl)-hexamethyleneimine
N-ethyl-N-(5-phenoxypentyl)-propylamine
1-(5-phenoxypentyl)-2-methyl-piperidine
1-(5-phenoxypentyl)-4-propyl-piperidine
1-(5-phenoxypentyl)-4-methyl-piperidine
1-(5-phenoxypentyl)-3-methyl-piperidine
1-acetyl-4-(5-phenoxypentyl)-piperazine
1-(5-phenoxypentyl)-3,5-trans-dimethyl-piperidine
1-(5-phenoxypentyl)-3,5-cis-dimethyl-piperidine
1-(5-phenoxypentyl)-2,6-cis-dimethyl-piperidine
4-carboethoxy-1-(5-phenoxypentyl)-piperidine
3-carboethoxy-1-(5-phenoxypentyl)-piperidine
1-[3-(4-cyclopropylcarbonylphenoxy)propyl]-piperidine
1-[3-(4-acetylphenoxy)-2-R-methylpropyl]piperidine
1-[3-(4-cyanophenoxy)propyl]-4-methylpiperidine
1-[3-(4-cyanophenoxy)propyl]-3-methylpiperidine
1-[3-(4-acetylphenoxy)-2-S-methylpropyl]piperidine
1-{3-[4-(3-oxobutyl)phenoxy]propyl}piperidine
1-[3-(4-cyano-3-fluorophenoxy)propyl]piperidine
1-[3-(4-nitrophenoxy)propyl]-3-methylpiperidine
1-[3-(4-cyanophenoxy)propyl]-2-methylpiperidine
1-[3-(4-nitrophenoxy)propyl]-2-methylpiperidine
1-[3-(4-nitrophenoxy)propyl]4-methylpiperidine
1-[3-(4-cyanophenoxy)propyl]-2,6-dimethylpiperidine
1-[3-(4-propionylphenoxy)propyl]-3-methylpiperidine
1-[3-(4-cyclobutylcarbonylphenoxy)propyl]piperidine
1-[3-(4-cyclopentylcarbonylphenoxy)propyl]piperidine
1-[3-(4-cyanophenoxy)propyl]-cis-2-methyl-5-ethylpiperidine
1-[3-(4-cyanophenoxy)propyl]-trans-2-methyl-5-ethylpiperidine
1-[3-(4-cyanophenoxy)propyl]-cis-3,5-dimethylpiperidine
1-[3-(4-propionylphenoxy)propyl]-4-methylpiperidine
1-[3-(4-propionylphenoxy)propyl]-2-methylpiperidine
1-{3-[4-(1-hydroxypropyl)phenoxy]propyl}-3-methylpiperidine
1-{3-[4-(1-hydroxypropyl)phenoxy]propyl}-4-methylpiperidine
1-[3-(4-propionylphenoxy)propyl]-2-methylpiperidine
1-[3-(4-propionylphenoxy)propyl]4-methylpiperidine methoxime
1-[3-(4-cyanophenoxy)propyl]-trans-3,5-dimethylpiperidine
1-[3-(4-cyclopropylcarbonylphenoxy)propyl]-trans-3,5-dimethylpiperidine
1-[3-(4-cyclopropylcarbonylphenoxy)propyl]-cis-3,5-dimethylpiperidine
1-[3-(4-carbomethoxyphenoxy)propyl]piperidine
1-[3-(4-propenylphenoxy)propyl]-2-methylpiperidine
1-[3-(4-propionylphenoxy)propyl]-2-methylpiperidine
1-{3-[4-(1-ethoxypropyl)phenoxy]propyl}-2-methylpiperidine
1-[3-(4-propionylphenoxy)propyl]-4-methylpiperidine
1-[3-(4-bromophenoxy)propyl]piperidine
1-[3-(4-nitrophenoxy)propyl]piperidine
1-[3-(4-N,N-dimethylsulfonamidophenoxy)propyl]piperidine
1-[3-(4-isopropylphenoxy)propyl]piperidine
1-[3-(4-sec-butylphenoxy)propyl]piperidine
1-[3-(4-propylphenoxy)propyl]piperidine
1-[3-(4-ethylphenoxy)propyl]piperidine
1-(5-phenoxypentyl)-1,2,3,6-tetrahydropyridine
1-[5-(4-nitrophenoxy)-pentyl]-pyrrolidine
1-[5-(4-chlorophenoxy)-pentyl]-pyrrolidine
1-[5-(4-methoxyphenoxy)-pentyl]-pyrrolidine 1-[5-(4-methylphenoxy)-pentyl]-pyrrolidine
1-[5-(4-cyanophenoxy)-pentyl]-pyrrolidine
1-[5-(2-naphthyloxy)-pentyl]-pyrrolidine
1-[5-(1-naphthyloxy)-pentyl]-pyrrolidine
1-[5-(3-chlorophenoxy)-pentyl]-pyrrolidine
1-[5-(4-phenylphenoxy)-pentyl]-pyrrolidine
1-{5-[2-(5,6,7,8-tetrahydronaphthyl)-oxy]-pentyl}-pyrrolidine
1-[5-(3-phenylphenoxy)-pentyl]-pyrrolidine
1-(5-phenoxypentyl)-2,5-dihydropyrrole
1-{5-[1-(5,6,7,8-tetrahydronaphthyl)-oxy]-pentyl}-pyrrolidine
1-(4-phenoxybutyl)-pyrrolidine
1-(6-phenoxyhexyl)-pyrrolidine
1-(5-phenylthiopentyl)-pyrrolidine
1-(4-phenylthiobutyl)-pyrrolidine
1-(3-phenoxypropyl)-pyrrolidine
1-[5-(3-nitrophenoxy)-pentyl]-pyrrolidine
1-[5-(4-fluorophenoxy)-pentyl]-pyrrolidine
1-[5-(4-nitrophenoxy)-pentyl]-3-methyl-piperidine
1-[5-(4-acetylphenoxy)-pentyl]-pyrrolidine
1-[5-(4-aminophenoxy)-pentyl]-pyrrolidine
1-[5-(3-cyanophenoxy)-pentyl]-pyrrolidine
N-[3-(4-nitrophenoxy)-propyl]-diethylamine
N-[3-(4-cyanophenoxy)-propyl]-diethylamine
1-[5-(4-benzoylphenoxy)-pentyl]-pyrrolidine
1-{5-[4-(phenylacetyl)-phenoxy]-pentyl}-pyrrolidine
N-[3-(4-acetylphenoxy)-propyl]-diethylamine
1-[5-(4-acetamidophenoxy)-pentyl]-pyrrolidine
1-[5-(4-phenoxyphenoxy)-pentyl]-pyrrolidine
1-[5-(4-N-benzamidophenoxy)-pentyl]-pyrrolidine
1-{5-[4-(1-hydroxyethyl)-phenoxy]-pentyl}-pyrrolidine
1-[5-(4-cyanophenoxy)-pentyl]-diethylamine
1-[5-(4-cyanophenoxy)-pentyl]-piperidine
N-[5-(4-cyanophenoxy)-pentyl]-dimethylamine
N-[2-(4-cyanophenoxy)-ethyl]-diethylamine
N-[3-(4-cyanophenoxy)-propyl]-dimethylamine
N-[4-(4-cyanophenoxy)-butyl]-diethylamine
N-[5-(4-cyanophenoxy)-pentyl]-dipropylamine
1-[3-(4-cyanophenoxy)-propyl]-pyrrolidine
1-[3-(4-cyanophenoxy)-propyl]-piperidine
N-[3-(4-cyanophenoxy)-propyl]-hexamethyleneimine
N-[6-(4-cyanophenoxy)-hexyl]-diethylamine
N-[3-(4-cyanophenoxy)-propyl]-dipropylamine
N-3-[4-(1-hydroxyethyl)-phenoxy]-propyl-diethylamine
4-(3-diethylaminopropoxy)-acetophenone-oxime
1-[3-(4-acetylphenoxy)-propyl]-piperidine
1-[3-(4-acetylphenoxy)-propyl]-3-methyl-piperidine
1-[3-(4-acetylphenoxy)-propyl]-3,5-trans-dimethyl-piperidine
1-[3-(4-acetylphenoxy)-propyl]4-methyl-piperidine
1-[3-(4-propionylphenoxy)-propyl]-piperidine
1-[3-(4-acetylphenoxy)-propyl]-3,5-cis-dimethyl-piperidine
1-[3-(4-formylphenoxy)-propyl]-piperidine
1-[3-(4-isobutyrylphenoxy)-propyl]-piperidine
N-[3-(4-propionylphenoxy)-propyl]-diethylamine
1-[3-(4-butyrylphenoxy)-propyl]-piperidine
1-[3-(4-acetylphenoxy)-propyl]-1,2,3,6-tetrahydropyridine
α-(4-Acetylphenoxy)-α'-(4-methylpiperidino)p-xylol
α-(4-Acetyl phenoxy)-α'-(3,5-cis-dimethylpiperidino)p-xylol
α-(4-Acetylphenoxy)-α'-(3,5-trans-dimethylpiperidino)p-xylol
α-(4-Acetylphenoxy)-α'-(2-methylpyrrolidino)p-xylol
α-(4-Cyclopropylcarbonylphenoxy)-α'-piperidino-p-xylol
α-(4-Cyclopropylcarbonylphenoxy)-α'-(4-methylpiperidino)p-xylol
α-(4-Cyclopropylcarbonylphenoxy)-α'-pyrrolidino-p-xylol
3-Phenylpropyl 3-(4-methylpiperidino)propylether
3-Phenylpropyl 3-(3,5-cis-dimethylpiperidino)propylether
3-Phenylpropyl 3-(3,5-trans-dimethylpiperidino)propylether
3-Phenylpropyl 3-(3-methylpiperidino)propylether
3-Phenylpropyl 3-pyrrolidinopropylether
3-(4-Chlorophenyl)propyl 3-(4-methylpiperidino)propylether
3-(4-Chlorophenyl)propyl 3-(3,5-cis-dimethylpiperidino)propylether
3-(4-Chlorophenyl)propyl 3-(3,5-trans-dimethylpiperidino)propylether
4-(6-Piperidinohexylamino)quinoline
2-Methyl 4-(3-piperidinopropylamino)quinoline
2-Methyl 4-(6-piperidinohexylamino)quinoline
7-Chloro-4-(3-piperidinopropylamino)quinoline
7-Chloro-4-(4-piperidinobutylamino)quinoline
7-Chloro-4-(8-piperidinooctylamino)quinoline
7-Chloro-4-(10-piperidinodecylamino)quinoline
7-Chloro-4-(12-piperidinododecylamino)quinoline
7-Chloro-4-(4-(3-piperidinopropoxy)phenylamino)quinoline
7-Chloro-4-(2-(4-(3-piperidinopropoxy)phenyl)ethylamino)quinoline
4-(6-Piperidinohexanoyl)phenyl 3-piperidinopropylether
5-Nitro-2-(5-piperidinopentylamino)pyridine
3-Nitro-2-(6-piperidinopentylamino)pyridine
5-Amino-2-(6-piperidinopentylamino)pyridine
2-(6-Piperidinohexylamino)quinoline
N-(4-Chlorobenzyl)-N'-cyclohexyl-3-piperidinopropyl isothiourea
2-(6-Piperidinohexylamino)benzothiazole
10-Piperidinodecylamine
3-Phenylpropyl 3-(N,N-diethylamino)propylether
N-(3-(N,N-Diethylamino)propyl)N'-phenylurea
N-Cyclohexylmethyl-N'-(3-piperidinopropyl)guanidine
N-(4-Bromobenzyl)-N'-(4-piperidinobutyl)sulphamide
3-Chloro-N-(4-piperidinobutyl)-N-methyl-benzenesulphonamide
N-(4-Chlorobenzyl)-2-(4-piperidinomethyl) phenyl)ethanamidine
1-(5-Cyclohexylpentanoyl)-1,4-bipiperidine
cis-1-(6-Cyclohexyl-3-hexen-1-yl)piperidine
trans-1-(6-Cyclohexyl-3-hexen-1-yl)piperidine
1-(2-(5,5-Dimethyl-1-hexin-1-yl)cyclopropyl)piperidine for the preparation of a medicament acting as a ligand for the histamine $H_3$-receptor and in particular as an antagonist and/or agonist of the histamine $H_3$-receptors.

The antagonists are advantageously used as active ingredient in particular, of medicaments having psychotropic effects, promoting wakefulness, attention, memory and improving mood, in treatment of pathologies such as Alzheimer disease and other cognitive disorders in aged persons, depressive or simply asthenic states.

Their nootropic effects can be useful to stimulate attention and memorization capacity in healthy humans.

In addition, these agents can be useful in treatment of obesity, vertigo and motion sickness.

It can also be useful to associate the compounds of the invention with other psychiatric agents such as neuroleptics to increase their efficiency and reduce their side effects.

Application in certain form of epilepsy is also foreseen.

Their therapeutic applications involve also peripheral organs mainly a stimulant of secretions or gastro-intestinal motricity.

The compounds of the invention are particularly useful for the treatment of CNS disorders of aged persons.

The said compounds may also be used as an agonist or partial agonist action on the said histamine receptors.

$H_3$ receptor agonists and partial agonists, through their cerebral effects, mainly exert sedative, tranquillizing, anti-stress and analgesic activity, indicating their use as mild sedative psychotropics, in particular in various psychosomatic disorders.

$H_3$ agonists and partial agonists are also indicated in the treatment of migraine states and other headaches.

Through their peripheral effects, $H_3$ receptor agonists and partial agonists will be mainly indicated in the treatment of respiratoy, allergic or inflammatory conditions (asthma, bronchitis, rhinitis, tracheitis, and the like), cardiac conditions (myocardial dysfunction and infarction), gastrointestinal conditions as a result of their antisecretory and anti-inflammatory actions (gastric and duodenal ulcers, ulcerative colitis, Crohn's disease, irritable bowel, faecal incontinence, and the like), conditions of the urogenital system (cystitis, metritis, premenstrual syndrome, as prostatic inflammations, urinary incontinence, genital disorders) and conditions of the cutaneous system (urticaria, itching). The anti-inflammatory and analgesic effect may usefully be turned to good account in the treatment of arthritis and other rheumatic conditions, conjunctivitis and other ocular inflammations, and sialorrhoea.

Compounds which are histamine $H_3$ receptor agonists or partial agonists are advantageously used as active principle of medicinal products, in particular having mild sedative, antisecretory, anti-inflammatory, steep-regulating and anti-convulsant effects, regulatory effects on hypothalamohypo-physeal secretion, antidepressant effects, modulatory effects on cerebral circulation, modulatory effects on the immune system, and anti-allergic and antimigraine effects.

Hence the present invention also relates to pharmaceutical compositions which contain as active principle a therapeutically effective amount of one of the agonist or partial agonist compounds of formule (A).

The present invention also relates to medicaments having the above-mentioned effects comprising as active ingredient, a therapeutically effective amount of a compound of formula (A).

The present invention relates more particularly to such medicaments containing a compound of formula (I) to (XVIII).

The present invention also relates to pharmaceutical compositions containing as active ingredient, a therapeutically effective amount of a compound (A) together with a pharmaceutically acceptable vehicle or excipient.

The invention is directed to such pharmaceutical compositions containing as active-ingredient, a compound of formula (I) to (XVIII).

The medicaments or pharmaceutical compositions according to the invention can be administered via oral, parenteral or topical routes, the active ingredient being combined with a therapeutically suitable excipient or vehicle.

According to the invention, oral administration is advantageously used.

Another subject of the present invention is the use of the compounds of formula (A) for the preparation of $H_3$-antagonist and/or agonist medicaments according to the above-mentioned forms.

The invention further relates to the use of the compounds of formula (A) for preparing medicaments having the precited effects.

The invention also concerns the use of a compound of formula (I) to (XVIII).

Still another subject of the invention is a method for the treatment of precited ailments comprising administering a therapeutically effective dose of a compound (I), optionally in combination with a therapeutically acceptable vehicle or excipient.

The invention is also directed to such a method comprising administering a therapeutically effective dose of a compound of formula (I) to (XVIII).

For each of the above-indications, the amount of the active ingredient will depend upon the condition of the patient.

However, a suitable effective dose will be in general in the range of from 10 to 500 mg per day and of from 1 to 10 mg/day for particularly active compounds.

These doses are given on the basis of the compound and should be adapted for the salts, hydrates or hydrated salts thereof.

The invention is now illustrated by the following examples.

EXAMPLES

The structure of the synthesized compounds and their method of preparation as well as their melting point, recrystalisation solvent and elemental analysis are summarized in the following Table I:

TABLE 1

| N | FORMULA STRUCTURE NAME | mp (recryst. solv) | analysis (calc.) | method |
|---|---|---|---|---|
| 1 | $C_{16}H_{25}NO; C_2H_2O_4$ 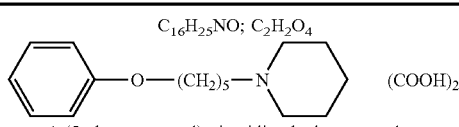 1-(5-phenoxypentyl)-piperidine hydrogen oxalate | 143–145° C. (absolute ethanol) | C: 64.06 (64.07) H: 8.09 (8.16) N: 4.14 (4.15) | A |
| 2 | $C_{15}H_{23}NO; C_2H_2O_4$ 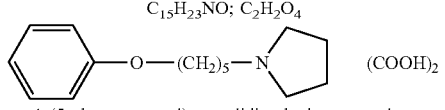 1-(5-phenoxypentyl)-pyrrolidine hydrogen oxalate | 153–155° C. (absolute ethanol) | C: 63.06 (63.14) H: 7.78 (7.79) N: 4.42 (4.33) | A |

TABLE 1-continued

| N | FORMULA STRUCTURE NAME | mp (recryst. solv) | analysis (calc.) | method |
|---|---|---|---|---|
| 3 | C$_{14}$H$_{23}$NO; C$_2$H$_2$O$_4$ 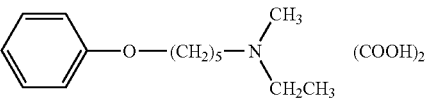 N-methyl-N-(5-phenoxypentyl)-ethylamine hydrogen oxalate | 122–124° C. (absolute ethanol) | C: 61.74 (61.72) H: 8.24 (8.09) N: 4.52 (4.50) | A |
| 4 | C$_{15}$H$_{23}$NO$_2$; C$_2$H$_2$O$_4$ 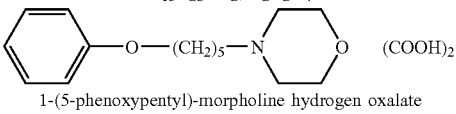 1-(5-phenoxypentyl)-morpholine hydrogen oxalate | 166–168° C. (absolute ethanol) | C: 60.10 (60.16) H: 7.45 (7.31) N: 4.08 (4.13) | A |
| 5 | C$_{17}$H$_{27}$NO; C$_2$H$_2$O$_4$ 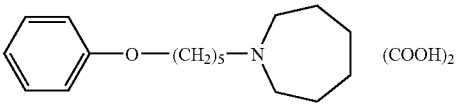 N-(5-phenoxypentyl)-hexamethyleneimine hydrogen oxalate | 132–134° C. (absolute ethanol) | C: 64.70 (64.93) H: 8.34 (8.32) N: 3.85 (3.99) | A |
| 6 | C$_{16}$H$_{27}$NO; C$_2$H$_2$O$_4$ 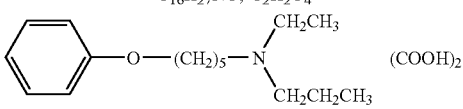 N-ethyl-N-(5-phenoxypentyl)-propylamine hydrogen oxalate | 90–91° C. (isopropyl alcohol) | C: 63.60 (63.69) H: 8.81 (8.61) N: 3.97 (4.13) | B |
| 7 | C$_{17}$H$_{27}$NO; 1.1 C$_2$H$_2$O$_4$ 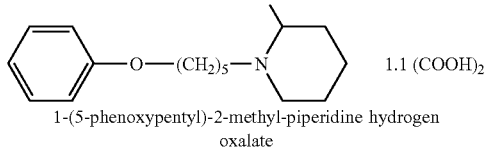 1-(5-phenoxypentyl)-2-methyl-piperidine hydrogen oxalate | 80–83° C. (isopropyl alcohol) | C: 64.15 (63.98) H: 8.42 (8.17) N: 3.97 (3.89) | B |
| 8 | C$_{19}$H$_{31}$NO; C$_2$H$_2$O$_4$ 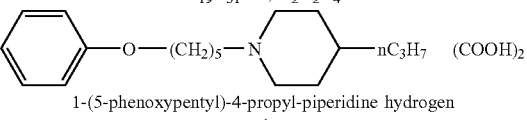 1-(5-phenoxypentyl)-4-propyl-piperidine hydrogen oxalate | 165–166° C. (absolute ethanol) | C: 66.27 (66.46) H: 8.94 (8.76) N: 3.72 (3.69) | B |
| 9 | C$_{17}$H$_{27}$NO; C$_2$H$_2$O$_4$ 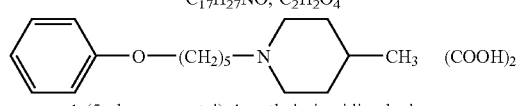 1-(5-phenoxypentyl)-4-methyl-piperidine hydrogen oxalate | 151–152° C. (absolute ethanol) | C: 64.87 (64.93) H: 8.41 (8.32) N: 4.01 (3.99) | B |
| 10 | C$_{17}$H$_{27}$NO; C$_2$H$_2$O$_4$ 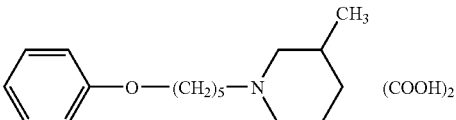 1-(5-phenoxypentyl)-3-methyl-piperidine hydrogen oxalate | 140–141° C. (isopropyl alcohol) | C: 65.35 (64.93) H: 8.49 (8.32) N: 4.00 (3.99) | B |

TABLE 1-continued

| N | FORMULA STRUCTURE NAME | mp (recryst. solv) | analysis (calc.) | method |
|---|---|---|---|---|
| 11 | $C_{17}H_{26}N_2O_2$; $C_2H_2O_4$ 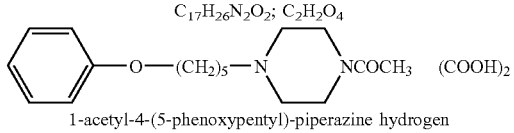 1-acetyl-4-(5-phenoxypentyl)-piperazine hydrogen oxalate | 186–188° C. (absolute ethanol) | C: 59.78 (59.99) H: 7.47 (7.42) N: 7.35 (7.36) | B |
| 12 | $C_{18}H_{29}NO$; 1.05 $C_2H_2O_4$ 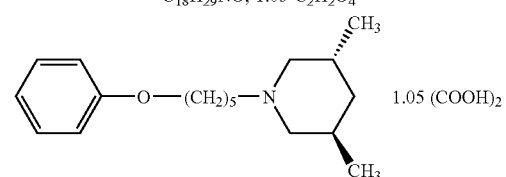 1-(5-phenoxypentyl)-3,5-trans-dimethyl-piperidine hydrogen oxalate | 154–155° C. (absolute ethanol) | C: 65.16 (65.25) H: 8.61 (8.47) N: 3.66 (3.79) | B |
| 13 | $C_{18}H_{29}NO$; $C_2H_2O_4$ 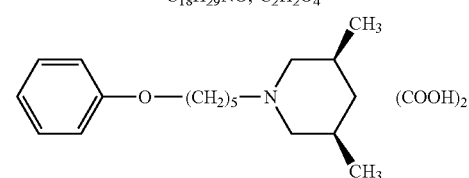 1-(5-phenoxypentyl)-3,5-cis-dimethyl-piperidine hydrogen oxalate | 154–155° C. (isopropyl alcohol) | C: 65.62 (65.73) H: 8.64 (8.55) N: 3.63 (3.83) | B |
| 14 | $C_{18}H_{29}NO$; HCl 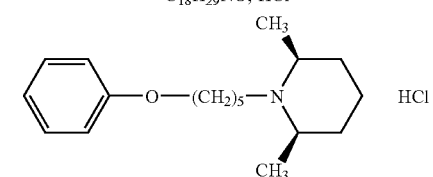 1-(5-phenoxypentyl)-2,6-cis-dimethyl-piperidine hydrochloride | 135–136° C. (acetone) | C: 69.18 (69.32) H: 9.79 (9.70) N: 4.28 (4.49) | B |
| 15 | $C_{19}H_{29}NO_3$; $C_2H_2O_4$ 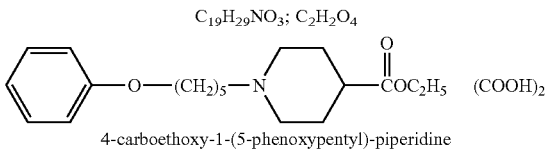 4-carboethoxy-1-(5-phenoxypentyl)-piperidine hydrogen oxalate | 149–150° C. (absolute ethanol) | C: 61.16 (61.60) H: 7.76 (7.63) N: 3.40 (3.42) | B |
| 16 | $C_{19}H_{29}NO_3$; $C_2H_2O_4$ 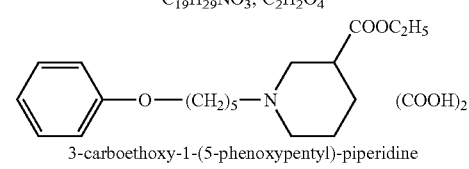 3-carboethoxy-1-(5-phenoxypentyl)-piperidine hydrogen oxalate | 117–118° C. (isopropyl alcohol) | C: 61.54 (61.60) H: 7.87 (7.63) N: 3.29 (3.42) | B |
| 17 | $C_{16}H_{23}NO$; $C_2H_2O_4$ 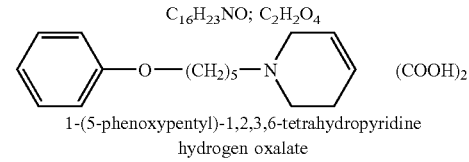 1-(5-phenoxypentyl)-1,2,3,6-tetrahydropyridine hydrogen oxalate | 177–179° C. (methanol) | C: 64.19 (64.46) H: 7.49 (7.51) N: 4.25 (4.18) | B |

TABLE 1-continued

| N | FORMULA STRUCTURE NAME | mp (recryst. solv) | analysis (calc.) | method |
|---|---|---|---|---|
| 18 | $C_{15}H_{22}N_2O_3$; $C_2H_2O_4$; 0.2 $H_2O$<br>$O_2N$—C6H4—O—$(CH_2)_5$—N(pyrrolidine) $(COOH)_2$ 0.2 $H_2O$<br>1-[5-(4-nitrophenoxy)-pentyl]-pyrrolidine hydrogen oxalate | 145–147° C. (absolute ethanol) | C: 54.89 (54.89)<br>H: 6.68 (6.61)<br>N: 7.41 (7.53) | C |
| 19 | $C_{15}H_{22}ClNO$; $C_2H_2O_4$<br>Cl—C6H4—O—$(CH_2)_5$—N(pyrrolidine) $(COOH)_2$<br>1-[5-(4-chlorophenoxy)-pentyl]-pyrrolidine hydrogen oxalate | 139–141° C. (absolute ethanol) | C: 57.00 (57.06)<br>H: 6.63 (6.76)<br>N: 3.79 (3.91)<br>Cl: 10.24 (9.91) | C |
| 20 | $C_{16}H_{25}NO_2$; $C_2H_2O_4$<br>$H_3CO$—C6H4—O—$(CH_2)_5$—N(pyrrolidine) $(COOH)_2$<br>1-[5-(4-methoxyphenoxy)-pentyl]-pyrrolidine hydrogen oxalate | 115–116° C. (absolute ethanol) | C: 61.22 (61.17)<br>H: 7.72 (7.70)<br>N: 4.03 (3.96) | C |
| 21 | $C_{16}H_{25}NO$; $C_2H_2O_4$<br>$H_3C$—C6H4—O—$(CH_2)_5$—N(pyrrolidine) $(COOH)_2$<br>1-[5-(4-methylphenoxy)-pentyl]-pyrrolidine hydrogen oxalate | 138–140° C. (absolute ethanol) | C: 64.05 (64.07)<br>H: 8.00 (8.07)<br>N: 4.10 (4.15) | C |
| 22 | $C_{16}H_{22}N_2O$; 1.1 $C_2H_2O_4$<br>NC—C6H4—O—$(CH_2)_5$—N(pyrrolidine) 1.1 $(COOH)_2$<br>1-[5-(4-cyanophenoxy)-pentyl]-pyrrolidine hydrogen oxalate | 129–130° C. (absolute ethanol) | C: 61.24 (61.16)<br>H: 6.81 (6.82)<br>N: 7.95 (7.84) | C |
| 23 | $C_{19}H_{25}NO$; $C_2H_2O_4$<br>(2-naphthyl)—O—$(CH_2)_5$—N(pyrrolidine) $(COOH)_2$<br>1-[5-(2-naphthyloxy)-pentyl]-pyrrolidine hydrogen oxalate | 166–167° C. (methanol) | C: 67.42 (67.54)<br>H: 7.26 (7.29)<br>N: 3.66 (3.75) | C |
| 24 | $C_{19}H_{25}NO$; 1.25 $C_2H_2O_4$<br>(1-naphthyl)—O—$(CH_2)_5$—N(pyrrolidine) 1.25 $(COOH)_2$<br>1-[5-(1-naphthyloxy)-pentyl]-pyrrolidine hydrogen oxalate | 160–163° C. (methanol) | C: 65.12 (65.22)<br>H: 7.17 (7.00)<br>N: 3.52 (3.54) | C |
| 25 | $C_{15}H_{22}ClNO$; $C_2H_2O_4$<br>(3-Cl-C6H4)—O—$(CH_2)_5$—N(pyrrolidine) $(COOH)_2$<br>1-[5-(3-chlorophenoxy)-pentyl]-pyrrolidine hydrogen oxalate | 131–132° C. (absolute ethanol) | C: 56.94 (57.06)<br>H: 6.67 (6.76)<br>N: 3.74 (3.91)<br>Cl: 9.64 (9.91) | C |

TABLE 1-continued

| N | FORMULA STRUCTURE NAME | mp (recryst. solv) | analysis (calc.) | method |
|---|---|---|---|---|
| 26 | C$_{21}$H$_{27}$NO; C$_2$H$_2$O$_4$<br>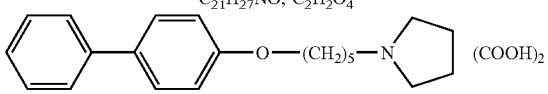<br>1-[5-(4-phenylphenoxy)-pentyl]-pyrrolidine hydrogen oxalate | 189–190° C. (methanol) | C: 69.16 (69.15)<br>H: 7.39 (7.32)<br>N: 3.39 (3.51) | C |
| 27 | C$_{19}$H$_{29}$NO; C$_2$H$_2$O$_4$<br>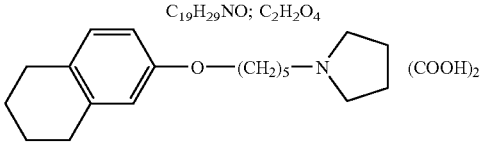<br>1-{5-[2-(5,6,7,8-tetrahydronaphthyl)-oxy]-pentyl}-pyrrolidine hydrogen oxalate | 131–132° C. (absolute ethanol) | C: 66.73 (66.82)<br>H: 8.37 (8.28)<br>N: 3.68 (3.71) | C |
| 28 | C$_{21}$H$_{27}$NO; 1.1 C$_2$H$_2$O$_4$<br>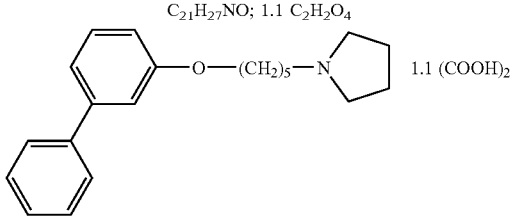<br>1-[5-(3-phenylphenoxy)-pentyl]-pyrrolidine hydrogen oxalate | 155–157° C. (absolute ethanol) | C: 68.40 (68.22)<br>H: 7.04 (7.21)<br>N: 3.45 (3.43) | C |
| 29 | C$_{15}$H$_{21}$NO; C$_2$H$_2$O$_4$<br>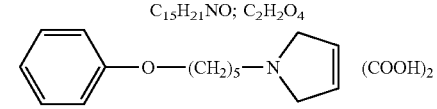<br>1-(5-phenoxypentyl)-2,5-dihydropyrrole hydrogen oxalate | 140–141° C. (absolute ethanol) | C: 63.45 (63.54)<br>H: 7.26 (7.21)<br>N: 4.26 (4.36) | B |
| 30 | C$_{19}$H$_{29}$NO; C$_2$H$_2$O$_4$<br>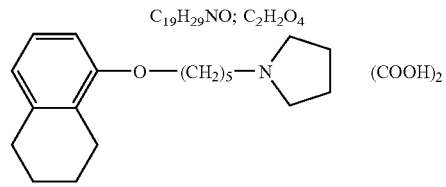<br>1-{5-[1-(5,6,7,8-tetrahydronaphthyl)-oxy]-pentyl}-pyrrolidine hydrogen oxalate | 148–149° C. (absolute ethanol) | C: 66.99 (66.82)<br>H: 8.47 (8.28)<br>N: 3.72 (3.71) | C |
| 31 | C$_{14}$H$_{21}$NO; C$_2$H$_2$O$_4$<br>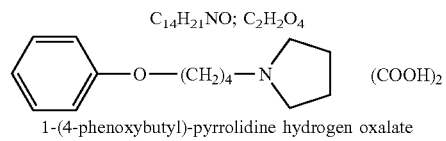<br>1-(4-phenoxybutyl)-pyrrolidine hydrogen oxalate | 143–144° C. (absolute ethanol) | C: 62.25 (62.12)<br>H: 7.46 (7.49)<br>N: 4.49 (4.53) | C |
| 32 | C$_{16}$H$_{25}$NO; 1.1 C$_2$H$_2$O$_4$<br>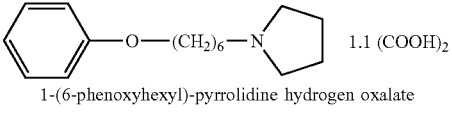<br>1-(6-phenoxyhexyl)-pyrrolidine hydrogen oxalate | 146–147° C. (absolute ethanol) | C: 63.06 (63.10)<br>H: 8.03 (7.91)<br>N: 4.32 (4.04) | C |
| 33 | C$_{15}$H$_{23}$NS; 1.1 C$_2$H$_2$O$_4$<br>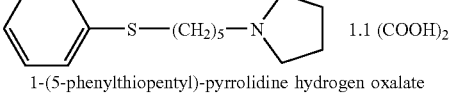<br>1-(5-phenylthiopentyl)-pyrrolidine hydrogen oxalate | 150–152° C. (absolute ethanol) | C: 59.52 (59.29)<br>H: 7.44 (7.29)<br>N: 4.06 (4.02) | C |

TABLE 1-continued

| N | FORMULA STRUCTURE NAME | mp (recryst. solv) | analysis (calc.) | method |
|---|---|---|---|---|
| 34 | $C_{14}H_{21}NS$; $C_2H_2O_4$ 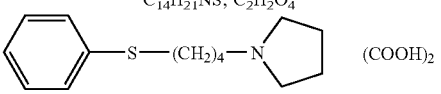 1-(4-phenylthiobutyl)-pyrrolidine hydrogen oxalate | 114–116° C. (absolute ethanol) | C: 59.24 (59.05) H: 7.16 (7.12) N: 4.16 (4.30) S: 9.79 (9.85) | C |
| 35 | $C_{13}H_{19}NO$; $C_2H_2O_4$ 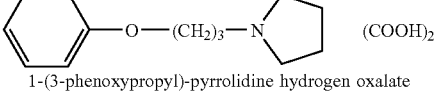 1-(3-phenoxypropyl)-pyrrolidine hydrogen oxalate | 169–170° C. (absolute ethanol) | C: 60.98 (61.00) H: 7.14 (7.17) N: 4.64 (4.74) | C |
| 36 | $C_{15}H_{22}N_2O_3$; $C_2H_2O_4$ 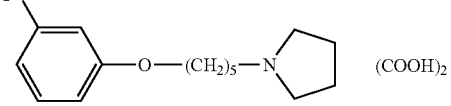 1-[5-(3-nitrophenoxy)-pentyl]-pyrrolidine hydrogen oxalate | 130–131° C. (absolute ethanol) | C: 55.30 (55.43) H: 6.55 (6.57) N: 7.49 (7.60) | C |
| 37 | $C_{15}H_{22}FNO$; $C_2H_2O_4$ 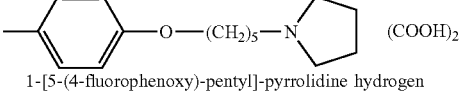 1-[5-(4-fluorophenoxy)-pentyl]-pyrrolidine hydrogen oxalate | 149–150° C. (absolute ethanol) | C: 59.52 (59.81) H: 7.12 (7.09) N: 4.05 (4.10) | C |
| 38 | $C_{17}H_{26}N_2O_3$; $C_2H_2O_4$ 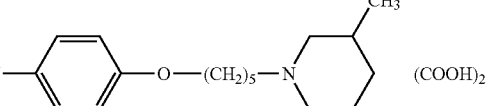 1-[5-(4-nitrophenoxy)-pentyl]-3-methyl-piperidine hydrogen oxalate | 148–149° C. (absolute ethanol) | C: 57.32 (57.55) H: 7.19 (7.12) N: 6.89 (7.07) | C |
| 39 | $C_{17}H_{25}NO_2$; $C_2H_2O_4$ 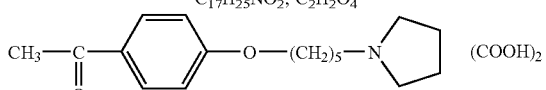 1-[5-(4-acetylphenoxy)-pentyl]-pyrrolidine hydrogen oxalate | 130–134° C. (absolute ethanol) | C: 62.43 (62.45) H: 7.41 (7.45) N: 3.75 (3.83) | D |
| 40 | $C_{15}H_{24}N_2O$; 2.1 $C_2H_2O_4$ 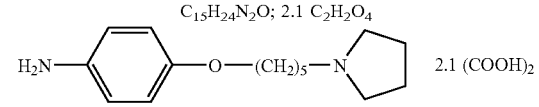 1-[5-(4-aminophenoxy)-pentyl]-pyrrolidine di-(hydrogen oxalate) | 120–122° C. (absolute ethanol) | C: 52.49 (52.72) H: 6.74 (6.50) N: 6.32 (6.40) | $E_1$ |
| 41 | $C_{16}H_{22}N_2O$; $C_2H_2O_4$ 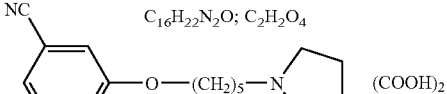 1-[5-(3-cyanophenoxy)-pentyl]-pyrrolidine hydrogen oxalate | 119–120° C. (absolute ethanol) | C: 61.95 (62.05) H: 6.88 (6.94) N: 8.00 (8.04) | C |
| 42 | $C_{13}H_{20}N_2O_3$; $C_2H_2O_4$ 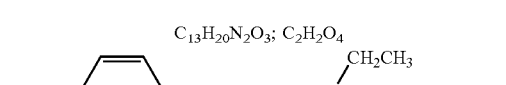 N-[3-(4-nitrophenoxy)-propyl]-diethylamine hydrogen oxalate | 160–161° C. (absolute ethanol/ methanol 1:1) | C: 52.46 (52.63) H: 6.49 (6.48) N: 8.10 (8.12) | F |

TABLE 1-continued

| N | FORMULA STRUCTURE NAME | mp (recryst. solv) | analysis (calc.) | method |
|---|---|---|---|---|
| 43 | $C_{14}H_{20}N_2O$; $C_2H_2O_4$ 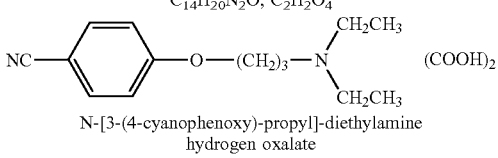<br>N-[3-(4-cyanophenoxy)-propyl]-diethylamine hydrogen oxalate | 148–150° C. (absolute ethanol) | C: 59.40 (59.62)<br>H: 6.82 (6.88)<br>N: 8.60 (8.69) | F |
| 44 | $C_{22}H_{27}NO_3$; $C_2H_2O_4$ 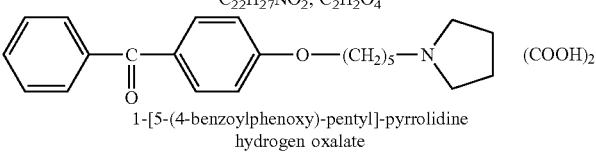<br>1-[5-(4-benzoylphenoxy)-pentyl]-pyrrolidine hydrogen oxalate | 141–142° C. (absolute ethanol) | C: 67.17 (67.43)<br>H: 6.80 (6.84)<br>N: 3.18 (3.28) | D |
| 45 | $C_{23}H_{29}NO_2$; $C_2H_2O_4$ 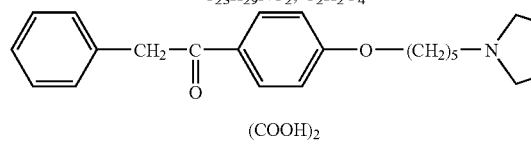<br>1-{5-[4-(phenylacetyl)-phenoxy]-pentyl}-pyrrolidine hydrogen oxalate | 177–178° C. (absolute ethanol) | C: 67.77 (68.01)<br>H: 7.09 (7.08)<br>N: 3.26 (3.17) | D |
| 46 | $C_{15}H_{23}NO_2$; 1.1 $C_2H_2O_4$ 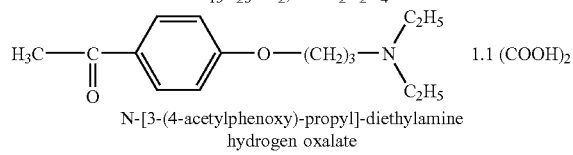<br>N-[3-(4-acetylphenoxy)-propyl]-diethylamine hydrogen oxalate | 108–110° C. (absolute ethanol) | C: 59.30 (59.30)<br>H: 7.47 (7.29)<br>N: 4.18 (4.02) | F |
| 47 | $C_{17}H_{26}N_2O_2$; $C_2H_2O_4$ 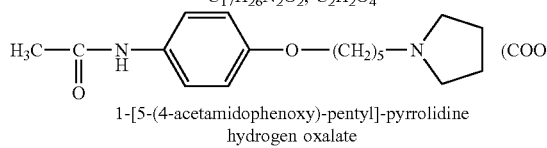<br>1-[5-(4-acetamidophenoxy)-pentyl]-pyrrolidine hydrogen oxalate | 142–144° C. (absolute ethanol) | C: 59.67 (59.99)<br>H: 7.55 (7.42)<br>N: 7.25 (7.36) | C |
| 48 | $C_{21}H_{27}NO_2$; $C_2H_2O_4$ 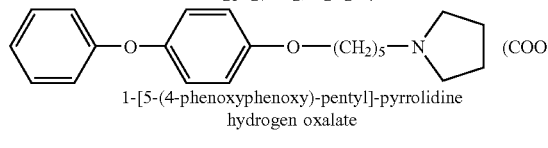<br>1-[5-(4-phenoxyphenoxy)-pentyl]-pyrrolidine hydrogen oxalate | 135–136° C. (absolute ethanol) | C: 66.49 (66.49)<br>H: 7.05 (7.04)<br>N: 3.24 (3.37) | D |
| 49 | $C_{22}H_{28}N_2O_2$; 1.1 $C_2H_2O_4$ 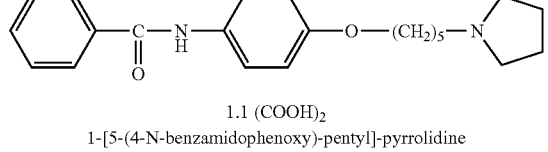<br>1-[5-(4-N-benzamidophenoxy)-pentyl]-pyrrolidine hydrogen oxalate | 176–178° C. (absolute ethanol) | C: 64.56 (64.38)<br>H: 6.89 (6.74)<br>N: 6.26 (6.20) | $E_2$ |
| 50 | $C_{17}H_{27}NO_2$; $C_2H_2O_4$ 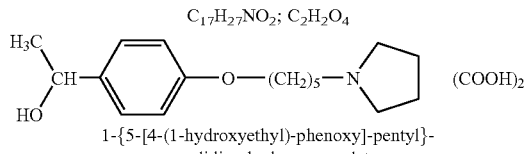<br>1-{5-[4-(1-hydroxyethyl)-phenoxy]-pentyl}-pyrrolidine hydrogen oxalate | 102–104° C. (absolute ethanol) | C: 61.89 (62.11)<br>H: 7.94 (7.96)<br>N: 3.77 (3.81) | G |

TABLE 1-continued

| N | FORMULA STRUCTURE NAME | mp (recryst. solv) | analysis (calc.) | method |
|---|---|---|---|---|
| 51 | C₁₆H₂₄N₂O; C₂H₂O₄<br>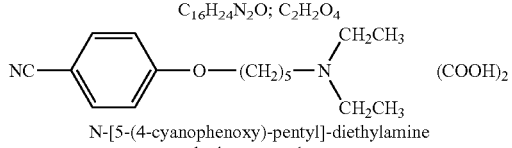<br>N-[5-(4-cyanophenoxy)-pentyl]-diethylamine hydrogen oxalate | 120–122° C. (absolute ethanol) | C: 61.56 (61.70)<br>H: 7.54 (7.48)<br>N: 7.87 (7.99) | H |
| 52 | C₁₇H₂₄N₂O; C₂H₂O₄<br>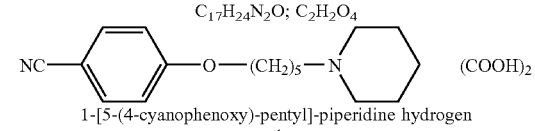<br>1-[5-(4-cyanophenoxy)-pentyl]-piperidine hydrogen oxalate | 115–116° C. (absolute ethanol) | C: 62.62 (62.97)<br>H: 7.20 (7.23)<br>N: 7.76 (7.73) | H |
| 53 | C₁₄H₂₀N₂O; C₂H₂O₄<br>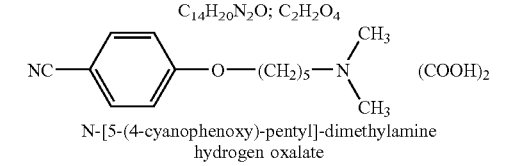<br>N-[5-(4-cyanophenoxy)-pentyl]-dimethylamine hydrogen oxalate | 148–149° C. (absolute ethanol) | C: 59.68 (59.62)<br>H: 6.76 (6.88)<br>N: 8.57 (8.69) | H |
| 54 | C₁₃H₁₈N₂O; C₂H₂O₄<br>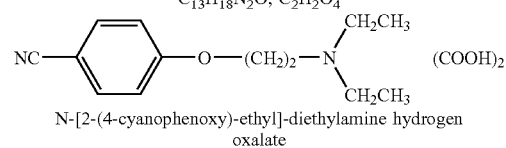<br>N-[2-(4-cyanophenoxy)-ethyl]-diethylamine hydrogen oxalate | 124–125° C. (absolute ethanol) | C: 58.15 (58.43)<br>H: 6.30 (6.54)<br>N: 8.95 (9.09) | H |
| 55 | C₁₂H₁₆N₂O; C₂H₂O₄<br>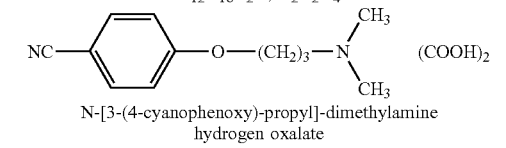<br>N-[3-(4-cyanophenoxy)-propyl]-dimethylamine hydrogen oxalate | 166–167° C. (absolute ethanol/ methanol 1:1) | C: 57.01 (57.14)<br>H: 6.02 (6.16)<br>N: 9.46 (9.52) | H |
| 56 | C₁₅H₂₂N₂O; C₂H₂O₄<br>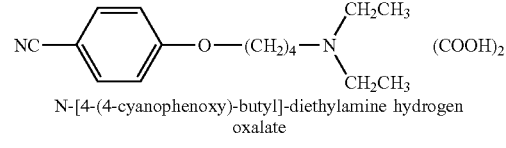<br>N-[4-(4-cyanophenoxy)-butyl]-diethylamine hydrogen oxalate | 143–145° C. (absolute ethanol) | C: 60.80 (60.70)<br>H: 7.11 (7.19)<br>N: 8.22 (8.33) | H |
| 57 | C₁₈H₂₈N₂O; C₂H₂O₄<br>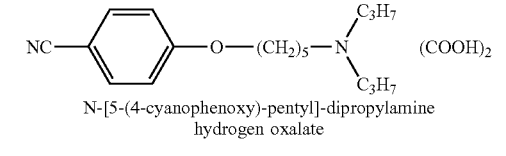<br>N-[5-(4-cyanophenoxy)-pentyl]-dipropylamine hydrogen oxalate | 134–136° C. (absolute ethanol) | C: 63.38 (63.47)<br>H: 8.11 (7.99)<br>N: 7.29 (7.40) | H |
| 58 | C₁₄H₁₈N₂O; 1.1 C₂H₂O₄<br>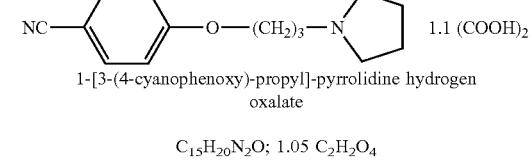<br>1-[3-(4-cyanophenoxy)-propyl]-pyrrolidine hydrogen oxalate | 163–165° C. (absolute ethanol) | C: 58.95 (59.08)<br>H: 6.23 (6.18)<br>N: 8.43 (8.51) | H |
| 59 | C₁₅H₂₀N₂O; 1.05 C₂H₂O₄<br>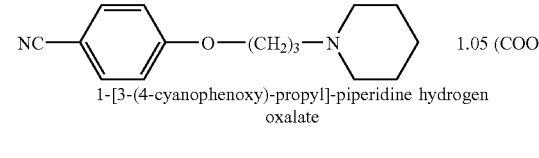<br>1-[3-(4-cyanophenoxy)-propyl]-piperidine hydrogen oxalate | 151–153° C. (absolute ethanol) | C: 60.62 (60.61)<br>H: 6.66 (6.57)<br>N: 8.25 (8.27) | H |

TABLE 1-continued

| N | FORMULA STRUCTURE NAME | mp (recryst. solv) | analysis (calc.) | method |
|---|---|---|---|---|
| 60 | $C_{16}H_{22}N_2O$; 1.05 $C_2H_2O_4$<br>NC—⟨phenyl⟩—O—$(CH_2)_3$—N⟨hexamethyleneimine⟩  1.05 $(COOH)_2$<br>N-[3-(4-cyanophenoxy)-propyl]-hexamethyleneimine hydrogen oxalate | 124–125° C.<br>(absolute ethanol) | C: 61.62 (61.60)<br>H: 6.94 (6.88)<br>N: 7.87 (7.94) | H |
| 61 | $C_{17}H_{26}N_2O$; $C_2H_2O_4$<br>NC—⟨phenyl⟩—O—$(CH_2)_6$—N(CH$_2$CH$_3$)$_2$  $(COOH)_2$<br>N-[6-(4-cyanophenoxy)-hexyl]-diethylamine hydrogen oxalate | 110–112° C.<br>(absolute ethanol) | C: 62.90 (62.62)<br>H: 7.76 (7.74)<br>N: 7.61 (7.69) | H |
| 62 | $C_{16}H_{24}N_2O$; $C_2H_2O_4$<br>NC—⟨phenyl⟩—O—$(CH_2)_3$—N($C_3H_7$)$_2$  $(COOH)_2$<br>N-[3-(4-cyanophenoxy)-propyl]-dipropylamine hydrogen oxalate | 127–128° C.<br>(absolute ethanol) | C: 61.57 (61.70)<br>H: 7.57 (7.48)<br>N: 7.91 (7.99) | H |
| 63 | $C_{15}H_{25}NO_2$; $C_2H_2O_4$; 0.5 $H_2O$<br>H$_3$C—CH(OH)—⟨phenyl⟩—O—$(CH_2)_3$—N($C_2H_5$)$_2$  $(COOH)_2$  0.5 $H_2O$<br>N-3-[4-(1-hydroxyethyl)-phenoxy]-propyl-diethylamine hydrogen oxalate hemihydrate | 33–36° C.<br>(isopropyl alcohol) | C: 58.15 (58.27)<br>H: 8.15 (8.05)<br>N: 4.21 (4.00) | G |
| 64 | $C_{15}H_{24}N_2O_2$; $C_2H_2O_4$<br>H$_3$C—C(=N—OH)—⟨phenyl⟩—O—$(CH_2)_3$—N($C_2H_5$)$_2$  $(COOH)_2$<br>4'-(3-diethylaminopropoxy)-acetophenone-oxime hydrogen oxalate | 99–100° C.<br>(absolute ethanol) | C: 57.26 (57.61)<br>H: 7.47 (7.39)<br>N: 7.72 (7.90) | J |
| 65 | $C_{16}H_{23}NO_2$; $C_2H_2O_4$<br>H$_3$C—C(=O)—⟨phenyl⟩—O—$(CH_2)_3$—N⟨piperidine⟩  $(COOH)_2$<br>1-[3-(4-acetylphenoxy)-propyl]-piperidine hydrogen oxalate | 159–160° C.<br>(absolute ethanol) | C: 61.18 (61.52)<br>H: 7.11 (7.17)<br>N: 3.96 (3.99) | K |
| 66 | $C_{17}H_{25}NO_2$; $C_2H_2O_4$<br>H$_3$C—C(=O)—⟨phenyl⟩—O—$(CH_2)_3$—N⟨3-methyl-piperidine⟩  $(COOH)_2$<br>1-[3-(4-acetylphenoxy)-propyl]-3-methyl-piperidine hydrogen oxalate | 143–144° C.<br>(absolute ethanol) | C: 62.11 (62.45)<br>H: 7.41 (7.45)<br>N: 3.79 (3.83) | K |
| 67 | $C_{18}H_{27}NO_2$; $C_2H_2O_4$<br>H$_3$C—C(=O)—⟨phenyl⟩—O—$(CH_2)_3$—N⟨3,5-trans-dimethyl-piperidine⟩  $(COOH)_2$<br>1-[3-(4-acetylphenoxy)-propyl]-3,5-trans-dimethyl-piperidine hydrogen oxalate | 171–172° C.<br>(absolute ethanol) | C: 63.06 (63.31)<br>H: 7.44 (7.70)<br>N: 3.64 (3.69) | K |

TABLE 1-continued

| N | FORMULA STRUCTURE NAME | mp (recryst. solv) | analysis (calc.) | method |
|---|---|---|---|---|
| 68 | $C_{17}H_{25}NO_2$; $C_2H_2O_4$ 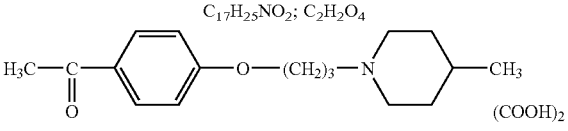 1-[3-(4-acetylphenoxy)-propyl]-4-methyl-piperidine hydrogen oxalate | 160–161° C. (absolute ethanol) | C: 62.47 (62.45) H: 7.46 (7.45) N: 3.77 (3.83) | K |
| 69 | $C_{17}H_{25}NO_2$; $C_2H_2O_4$ 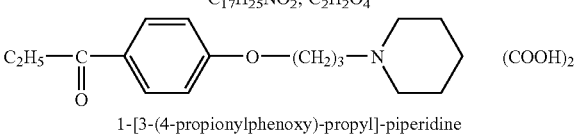 1-[3-(4-propionylphenoxy)-propyl]-piperidine hydrogen oxalate | 148–149° C. (absolute ethanol) | C: 62.54 (62.45) H: 7.51 (7.45) N: 3.79 (3.83) | L |
| 70 | $C_{18}H_{27}NO_2$; $C_2H_2O_4$ 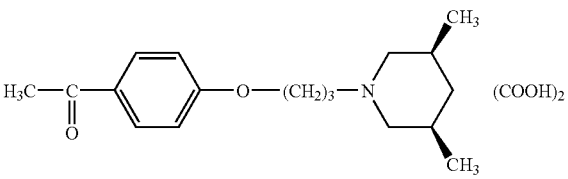 1-[3-(4-acetylphenoxy)-propyl]-3,5-cis-dimethyl-piperidine hydrogen oxalate | 174–175° C. (absolute ethanol) | C: 63.22 (63.31) H: 7.60 (7.70) N: 3.64 (3.69) | K |
| 71 | $C_{15}H_{21}NO_2$; $C_2H_2O_4$ 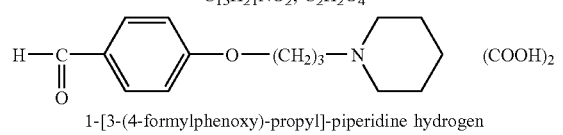 1-[3-(4-formylphenoxy)-propyl]-piperidine hydrogen oxalate | 152–153° C. (absolute ethanol) | C: 60.23 (60.52) H: 6.81 (6.87) N: 4.15 (4.15) | L |
| 72 | $C_{18}H_{27}NO_2$; $C_2H_2O_4$ 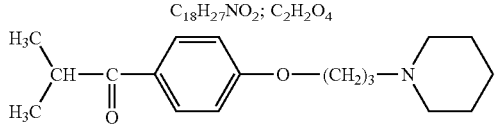 1-[3-(4-isobutyrylphenoxy)-propyl]-piperidine hydrogen oxalate | 121–122° C. (absolute ethanol) | C: 63.02 (63.31) H: 7.73 (7.70) N: 3.66 (3.69) | L |
| 73 | $C_{16}H_{25}NO_2$; 1.5 $C_2H_2O_4$ 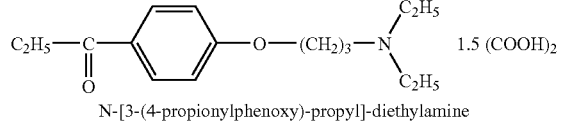 N-[3-(4-propionylphenoxy)-propyl]-diethylamine hydrogen oxalate | 118–120° C. (absolute ethanol) | C: 57.27 (57.28) H: 7.00 (7.08) N: 3.47 (3.52) | L |
| 74 | $C_{18}H_{27}NO_2$; $C_2H_2O_4$ 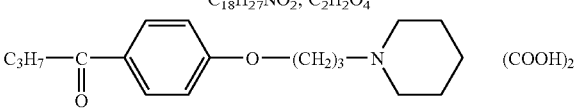 1-[3-(4-butyrylphenoxy)-propyl]-piperidine hydrogen oxalate | 138–139° C. (absolute ethanol) | C: 63.09 (63.31) H: 7.78 (7.70) N: 3.75 (3.69) | L |

TABLE 1-continued

| N | FORMULA STRUCTURE NAME | mp (recryst. solv) | analysis (calc.) | method |
|---|---|---|---|---|
| 75 | C₁₆H₂₁NO₂; 1.1 C₂H₂O₄ 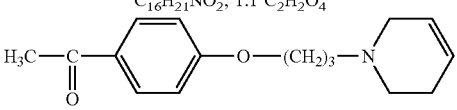 1.1 (COOH)₂ 1-[3-(4-acetylphenoxy)-propyl]-1,2,3,6-tetrahydropyridine hydrogen oxalate | 143–144° C. (absolute ethanol) | C: 61.21 (61.00) H: 6.25 (6.52) N: 4.00 (3.91) | K |
| 76 | C₁₈H₂₅NO₂; 1.05 C₂H₂O₄ 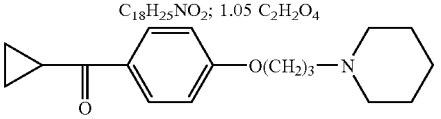 1.05 (COOH)₂ 1-[3-(4-cyclopropanecarbonylphenoxy) propyl]-piperidine hydrogen oxalate | 177–179° C. (absolute ethanol) | C: 63.10 (63.21) H: 7.28 (7.15) N: 3.61 (3.67) | L |
| 77 | C₁₇H₂₅NO₂; 1.1 C₂H₂O₄ 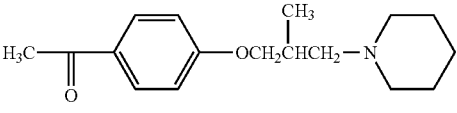 1.1 (COOH)₂ 1-[3-(4-acetylphenoxy)-2-R-methylpropyl]piperidine hydrogen oxalate | 149–151° C. (absolute ethanol) | C: 61.72 (61.59) H: 7.59 (7.32) N: 3.74 (3.74) | M |
| 78 | C₁₆H₂₂N₂O; HCl; 0.1 H₂O 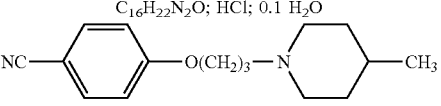 HCl; 0.1 H₂O 1-[3-(4-cyanophenoxy)propyl]-4-methylpiperidine hydrochloride | 200–202° C. (absolute ethanol/diethyl ether 1:1) | C: 64.57 (64.79) H: 8.02 (7.88) N: 9.30 (9.44) | N |
| 79 | C₁₆H₂₂N₂O; HCl 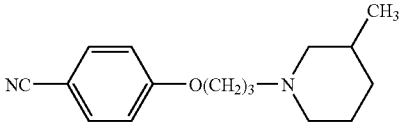 HCl 1-[3-(4-cyanophenoxy)propyl]-3-methylpiperidine hydrochloride | 171–173° C. (absolute ethanol/diethyl ether 1:1) | C: 64.87 (65.18) H: 8.01 (7.86) N: 9.40 (9.50) | N |
| 80 | C₁₇H₂₅NO₂; C₂H₂O₄ 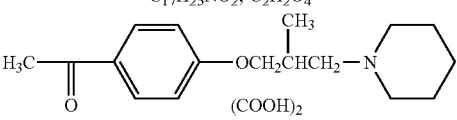 (COOH)₂ 1-[3-(4-acetylphenoxy)-2-S-methylpropyl] piperidine hydrogen oxalate | 148–150° C. (absolute ethanol) | C: 62.20 (62.45) H: 7.46 (7.45) N: 3.73 (3.83) | M |
| 81 | C₁₈H₂₇NO₂; HCl 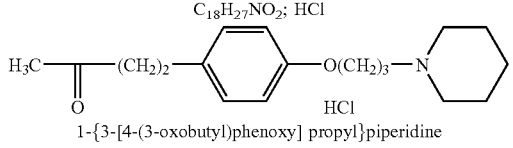 HCl 1-{3-[4-(3-oxobutyl)phenoxy] propyl}piperidine hydrochloride | 148–150° C. (acetone) | C: 66.10 (66.34) H: 8.92 (8.66) N: 4.16 (4.30) | O |

TABLE 1-continued

| N | FORMULA STRUCTURE NAME | mp (recryst. solv) | analysis (calc.) | method |
|---|---|---|---|---|
| 82 | $C_{15}H_{19}FN_2O$; HCl; 0.25 $H_2O$<br><br>NC—⟨3-F,4⟩—$O(CH_2)_3$—N(piperidine)<br>HCl; 0.25 $H_2O$<br>1-[3-(4-cyano-3-fluorophenoxy)propyl] piperidine hydrochloride | 157–159° C.<br>(absolute ethanol/diethyl ether 1:4) | C: 59.13 (59.40)<br>H: 6.60 (6.81)<br>N: 8.94 (9.24) | L |
| 83 | $C_{15}H_{22}N_2O_3$; $C_2H_2O_4$<br><br>$O_2N$—⟨⟩—$O(CH_2)_3$—N(3-CH$_3$-piperidine)<br>(COOH)$_2$<br>1-[3-(4-nitrophenoxy)propyl]-3-methylpiperidine hydrogen oxalate | 172–174° C.<br>(absolute ethanol) | C: 55.45 (55.43)<br>H: 6.53 (6.57)<br>N: 7.58 (7.60) | N |
| 84 | $C_{16}H_{22}N_2O$; HCl<br><br>NC—⟨⟩—$O(CH_2)_3$—N(2-CH$_3$-piperidine)<br>HCl<br>1-[3-(4-cyanophenoxy)propyl]-2-methylpiperidine hydrochloride | 177–180° C.<br>(absolute ethanol/diethyl ether 1:5) | C: 64.96 (65.18)<br>H: 7.79 (7.86)<br>N: 9.44 (9.50) | N |
| 85 | $C_{15}H_{22}N_2O_3$; $C_2H_2O_4$<br><br>$O_2N$—⟨⟩—$O(CH_2)_3$—N(2-CH$_3$-piperidine)<br>(COOH)$_2$<br>1-[3-(4-nitrophenoxy)propyl]-2-methylpiperidine hydrogen oxalate | 151–153° C.<br>(absolute ethanol) | C: 55.38 (55.43)<br>H: 6.57 (6.57)<br>N: 7.40 (7.60) | N |
| 86 | $C_{15}H_{22}N_2O_3$; 1.1 $C_2H_2O_4$<br><br>$O_2N$—⟨⟩—$O(CH_2)_3$—N(piperidine)—CH$_3$<br>1.1 (COOH)$_2$<br>1-[3-(4-nitrophenoxy)propyl]-4-methylpiperidine hydrogen oxalate | 119–121° C.<br>(absolute ethanol) | C: 54.52 (54.74)<br>H: 6.55 (6.46)<br>N: 7.19 (7.42) | N |

TABLE 1-continued

| N | FORMULA STRUCTURE NAME | mp (recryst. solv) | analysis (calc.) | method |
|---|---|---|---|---|
| 87 | $C_{16}H_{22}N_2O$; 1.4 HCl; 1.5 $H_2O$ 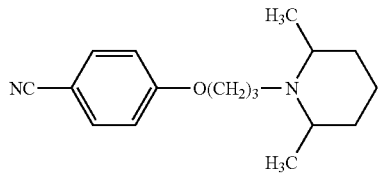 1.4 HCl; 1.5 $H_2O$ 1-[3-(4-cyanophenoxy)propyl]-2,6-dimethylpiperidine hydrochloride | 180–1825° C. (absolute ethanol/diethyl ether 1:5) | C: 58.52 (58.26) H: 8.20 (8.17) N: 7.90 (7.99) | N |
| 88 | $C_{18}H_{27}NO_2$; $C_2H_2O_4$ 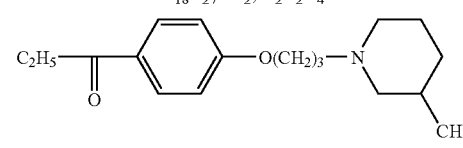 (COOH)$_2$ 1-[3-(4-propionylphenoxy)propyl]-3-methylpiperidine hydrogen oxalate | 135–136° C. (methanol/ absolute ethanol 1:1) | C: 63.34 (63.31) H: 7.63 (7.70) N: 3.65 (3.69) | N |
| 89 | $C_{19}H_{27}NO_2$; 1.8 $C_2H_2O_4$ 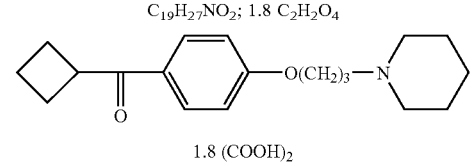 1.8 (COOH)$_2$ 1-[3-(4-cyclobutanecarbonylphenoxy)propyl] piperidine hydrogen oxalate | 80–82° C. (absolute ethanol) | C: 58.54 (58.57) H: 6.57 (6.65) N: 2.97 (3.02) | L |
| 90 | $C_{20}H_{29}NO_2$; 1.1 $C_2H_2O_4$ 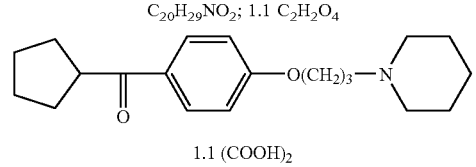 1.1 (COOH)$_2$ 1-[3-(4-cyclopentanecarbonylphenoxy) propyl]piperidine hydrogen oxalate | 143–145° C. (absolute ethanol/diethyl ether 1:1) | C: 64.39 (64.33) H: 7.78 (7.59) N: 3.36 (3.38) | L |
| 91 | $C_{18}H_{26}N_2O$; 1.05 $C_2H_2O_4$ 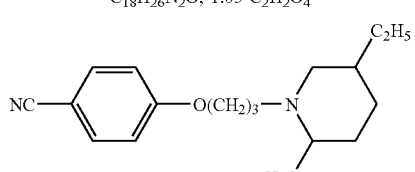 1.05 (COOH)$_2$ 1-[3-(4-cyanophenoxy)propyl]-cis-2-methyl-5-ethylpiperidine hydrogen oxalate | 158–159° C. (absolute ethanol) | C: 63.38 (63.37) H: 7.19 (7.43) N: 7.22 (7.35) | N |

TABLE 1-continued

| N | FORMULA STRUCTURE NAME | mp (recryst. solv) | analysis (calc.) | method |
|---|---|---|---|---|
| 92 | $C_{18}H_{26}N_2O$; 1.4 $C_2H_2O_4$; 0.6 $C_2H_5OH$<br><br>NC—⟨phenyl⟩—O(CH$_2$)$_3$—N(piperidine with 2-CH$_3$, 5-C$_2$H$_5$)<br><br>1.4 (COOH)$_2$; 0.6 $C_2H_5OH$<br>1-[3-(4-cyanophenoxy)propyl]-trans-2-methyl-5-ethylpiperidine hydrogen oxalate | sticky oil (after removal of absolute ethanol) | C: 59.89 (60.04)<br>H: 7.39 (7.42)<br>N: 6.31 (6.37) | N |
| 93 | $C_{17}H_{24}N_2O$; $C_2H_2O_4$<br><br>NC—⟨phenyl⟩—O(CH$_2$)$_3$—N(piperidine with 3,5-diCH$_3$)<br><br>(COOH)$_2$<br>1-[3-(4-cyanophenoxy)propyl]-cis-3,5-dimethylpiperidine hydrogen oxalate | 161–163° C. (absolute ethanol) | C: 62.73 (62.97)<br>H: 7.28 (7.23)<br>N: 7.64 (7.73) | N |
| 94 | $C_{18}H_{27}NO_2$; 1.1 $C_2H_2O_4$<br><br>$C_2H_5$—C(=O)—⟨phenyl⟩—O(CH$_2$)$_3$—N(piperidine)—CH$_3$<br><br>1.1 (COOH)$_2$<br>1-[3-(4-propionylphenoxy)propyl]-4-methylpiperidine hydrogen oxalate | 163–165° C. (methanol/ absolute ethanol 1:1) | C: 62.43 (62.46)<br>H: 7.67 (7.58)<br>N: 3.53 (3.61) | N |
| 95 | $C_{18}H_{27}NO_2$; $C_2H_2O_4$<br><br>$C_2H_5$—C(=O)—⟨phenyl⟩—O(CH$_2$)$_3$—N(piperidine with 2-CH$_3$)<br><br>(COOH)$_2$<br>1-[3-(4-propionylphenoxy)propyl]-2-methylpiperidine hydrogen oxalate | 92–94° C. (methanol/ absolute ethanol 1:1) | C: 63.01 (63.31)<br>H: 7.79 (7.70)<br>N: 3.61 (3.69) | N |
| 96 | $C_{18}H_{29}NO_2$; $C_2H_2O_4$<br><br>$C_2H_5$—CH(OH)—⟨phenyl⟩—O(CH$_2$)$_3$—N(piperidine with 3-CH$_3$)<br><br>(COOH)$_2$<br>1-{3-[4-(1-hydroxypropyl)phenoxy]propyl}-3-methylpiperidine hydrogen oxalate | 144–145° C. (methanol/ absolute ethanol 1:1) | C: 62.95 (62.97)<br>H: 8.13 (8.19)<br>N: 3.54 (3.67) | P |
| 97 | $C_{18}H_{29}NO_2$; $C_2H_2O_4$<br><br>$C_2H_5$—CH(OH)—⟨phenyl⟩—O(CH$_2$)$_3$—N(piperidine)—CH$_3$<br><br>(COOH)$_2$<br>1-{3-[4-(1-hydroxypropyl)phenoxy]propyl}-4-methylpiperidine hydrogen oxalate | 182–183° C. (methanol/ absolute ethanol 1:1) | C: 62.64 (62.97)<br>H: 8.31 (8.19)<br>N: 3.62 (3.67) | P |

TABLE 1-continued

| N | FORMULA STRUCTURE NAME | mp (recryst. solv) | analysis (calc.) | method |
|---|---|---|---|---|
| 98 | C$_{18}$H$_{28}$N$_2$O$_2$; HCl; 0.1 H$_2$O 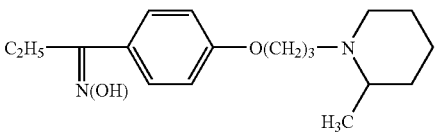 HCl; 0.1 H$_2$O 1-[3-(4-propionylphenoxy)propyl]-2-methylpiperidine oxime hydrochloride | 151–153° C. (absolute ethanol/diethyl ether 1:1) | C: 62.91 (63.09) H: 8.64 (8.59) N: 8.28 (8.17) | J |
| 99 | C$_{19}$H$_{30}$N$_2$O$_2$; C$_2$H$_2$O$_4$ 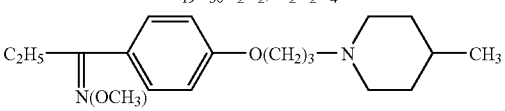 (COOH)$_2$ 1-[3-(4-propionylphenoxy)propyl]-4-methylpiperidine methoxime hydrogen oxalate | 179–181° C. (methanol/ absolute ethanol 1:1) | C: 61.86 (61.75) H: 7.81 (7.90) N: 6.82 (6.86) | Q |
| 100 | C$_{17}$H$_{24}$N$_2$O; C$_2$H$_2$O$_4$ 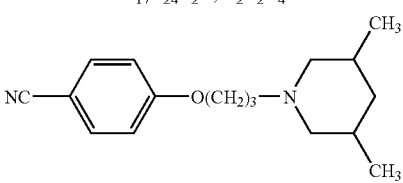 (COOH)$_2$ 1-[3-(4-cyanophenoxy)propyl]-trans-3,5-dimethylpiperidine hydrogen oxalate | 163–165° C. (absolute ethanol) | C: 63.04 (62.97) H: 7.10 (7.23) N: 7.53 (7.73) | N |
| 101 | C$_{20}$H$_{29}$NO$_2$; C$_2$H$_2$O$_4$; 0.2 H$_2$O 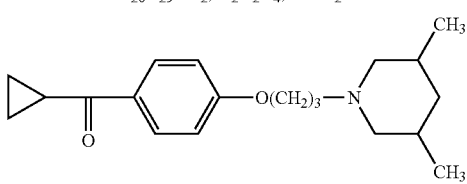 (COOH)$_2$; 0.2 H$_2$O 1-[3-(4-cyclopropylcarbonylphenoxy)propyl]-trans-3,5-dimethylpiperidine hydrogen oxalate | 136–138° C. (absolute ethanol/diethyl ether 1:1) | C: 64.54 (64.59) H: 7.70 (7.74) N: 3.44 (3.42) | N |
| 102 | C$_{20}$H$_{29}$NO$_2$; 1.1 C$_2$H$_2$O$_4$ 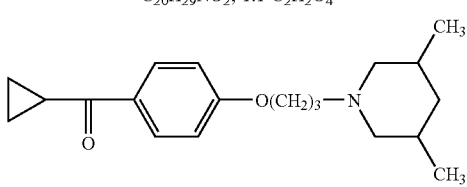 1.1 (COOH)$_2$ 1-[3-(4-cyclopropylcarbonylphenoxy)propyl]-cis-3,5-dimethylpiperidine hydrogen oxalate | 130–132° C. (absolute ethanol/diethyl ether 1:1) | C: 64.50 (64.33) H: 7.82 (7.59) N: 3.33 (3.38) | N |

TABLE 1-continued

| N | FORMULA STRUCTURE NAME | mp (recryst. solv) | analysis (calc.) | method |
|---|---|---|---|---|
| 103 | C₁₆H₂₃NO₃; C₂H₂O₄ 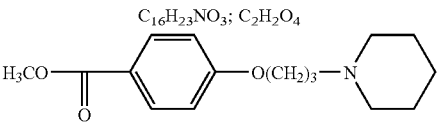 (COOH)₂ 1-[3-(4-carbomethoxyphenoxy)propyl] piperidine hydrogen oxalate | 156–158° C. (methanol) | C: 59.03 (58.85) H: 6.76 (6.86) N: 3.77 (3.81) | L |
| 104 | C₁₈H₂₇NO; C₇H₈SO₃ 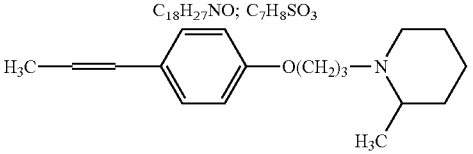 CH₃C₆H₄SO₃H 1-[3-(4-propenylphenoxy)propyl]-2-methyl piperidine hydrogen p-toluene sulfonate | 118–120° C. (absolute ethanol/diethyl ether 1:3) | C: 67.26 (67.38) H: 7.83 (7.92) N: 3.08 (3.14) | R |
| 105 | C₁₉H₃₀N₂O₂; HCl 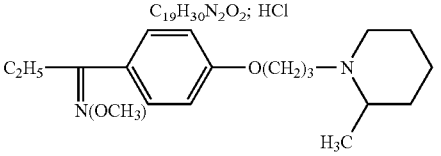 HCl 1-[3-(4-propionylphenoxy)propyl]-2-methylpiperidine methoxime hydrochloride | 185–187° C. (absolute ethanol/diethyl ether 1:3) | C: 64.28 (64.30) H: 8.77 (8.80) N: 7.80 (7.89) | Q |
| 106 | C₂₀H₃₃NO₂; C₇H₈SO₃; 0.3 H₂O 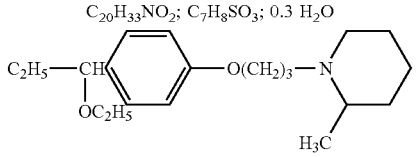 CH₃C₆H₄SO₃H; 0.3 H₂O 1-{3-[4-(1-ethoxypropyl)phenoxy]propyl}-2-methyl piperidine hydrogen p-toluene sulfonate | 105–107° C. (absolute ethanol/diethyl ether 1:3) | C: 65.25 (65.24) H: 8.44 (8.44) N: 2.80 (2.82) | S |
| 107 | C₁₈H₂₈N₂O₂; C₂H₂O₄; 0.5 CH₃OH 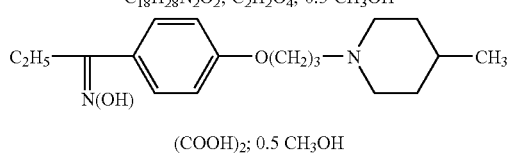 (COOH)₂; 0.5 CH₃OH 1-[3-(4-propionylphenoxy)propyl]-4-methylpiperidine oxime hydrogen oxalate | 157–160° C. (methanol) | C: 59.92 (59.98) H: 8.00 (7.86) N: 6.74 (6.82) | J |
| 108 | C₁₄H₂₀BrNO; C₂H₂O₄ 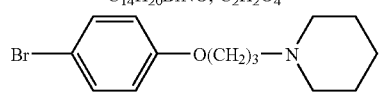 (COOH)₂ 1-[3-(4-bromophenoxy)propyl]piperidine hydrogen oxalate | 175–177° C. (absolute ethanol) | C: 49.52 (49.50) H: 5.62 (5.71) N: 3.50 (3.61) | L |

TABLE 1-continued

| N | FORMULA STRUCTURE NAME | mp (recryst. solv) | analysis (calc.) | method |
|---|---|---|---|---|
| 109 | $C_{14}H_{20}N_2O_3$; $C_2H_2O_4$ 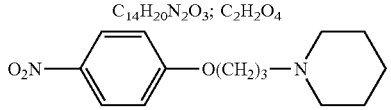 (COOH)$_2$ 1-[3-(4-nitrophenoxy)propyl]piperidine hydrogen oxalate | 148–151° C. (absolute ethanol) | C: 54.14 (54.23) H: 6.26 (6.26) N: 7.88 (7.91) | L |
| 110 | $C_{16}H_{26}SN_2O_3$; $C_2H_2O_4$ 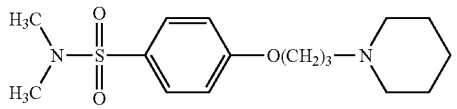 (COOH)$_2$ 1-[3-(4-N,N-dimethylsulfonamidophenoxy) propyl]piperidine hydrogen oxalate | 149–153° C. (absolute ethanol) | C: 51.58 (51.91) H: 6.80 (6.78) N: 6.84 (6.73) | L |
| 111 | $C_{17}H_{27}NO$; $C_2H_2O_4$ 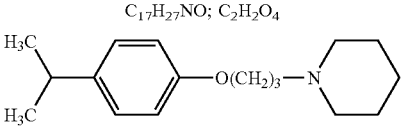 (COOH)$_2$ 1-[3-(4-isopropylphenoxy)propyl]piperidine hydrogen oxalate | 131–134° C. (absolute ethanol) | C: 64.68 (64.93) H: 8.50 (8.32) N: 3.96 (3.99) | L |
| 112 | $C_{18}H_{29}NO$; 1.1 $C_2H_2O_4$ 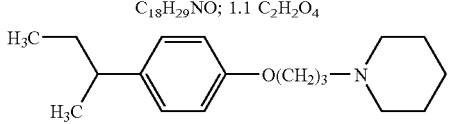 1.1 (COOH)$_2$ 1-[3-(4-sec-butylphenoxy)propyl]piperidine hydrogen oxalate | 133–136° C. (absolute ethanol) | C: 64.67 (64.79) H: 8.47 (8.40) N: 3.76 (3.74) | L |
| 113 | $C_{17}H_{27}NO$; $C_2H_2O_4$; 0.5 $H_2O$ 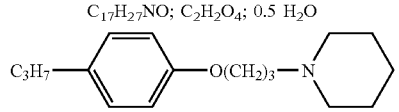 (COOH)$_2$; 0.5 $H_2O$ 1-[3-(4-propylphenoxy)propyl]piperidine hydrogen oxalate | 121–124° C. (absolute ethanol) | C: 63.46 (63.31) H: 8.36 (8.39) N: 3.92 (3.89) | L |
| 114 | $C_{16}H_{25}NO$; $C_2H_2O_4$; 0.5 $H_2O$ 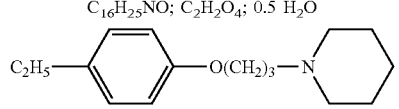 (COOH)$_2$; 0.5 $H_2O$ 1-[3-(4-ethylphenoxy)propyl]piperidine hydrogen oxalate | 148–151° C. (absolute ethanol) | C: 62.65 (62.41) H: 7.88 (8.15) N: 4.42 (4.04) | L |

| No | Structure | Synthesis |
|---|---|---|
| 115 | piperidine-(CH₂)₃-O-CH₂-C(CH₃)₃ | piperidine-(CH₂)₃-OH  $\xrightarrow{NaH, (a)}$  (CH₃)₃C-CH₂-Cl  $\xrightarrow{(b)}$ |
| 116 | piperidine-(CH₂)₂-O-(CH₂)₂-Ph | piperidine-(CH₂)₂-OH  $\xrightarrow{NaH, (a)}$  Ph-(CH₂)₂-Br  $\xrightarrow{(b)}$ |
| 117 | piperidine-(CH₂)₃-O-(CH₂)₂-C₆H₄-Cl | piperidine-(CH₂)₃-OH  $\xrightarrow{NaH, (a)}$  H₃C-SO₃-(CH₂)₂-C₆H₄-Cl  $\xrightarrow{(b)}$ |
| 118 | piperidine-(CH₂)₃-O-benzothiazole | piperidine-(CH₂)₃-OH  $\xrightarrow{NaH, (a)}$  2-Cl-benzothiazole  $\xrightarrow{(c)}$ |
| 119 | piperidine-(CH₂)₃-O-C(=O)-NH-Ph | piperidine-(CH₂)₃-OH  $\xrightarrow{}$  Ph-N=C=O  $\xrightarrow{(d)}$ |
| 120 | piperidine-(CH₂)₃-O-C(=O)-NH-C₅H₁₁ | piperidine-(CH₂)₃-OH  $\xrightarrow{}$  C₅H₁₁-N=C=O  $\xrightarrow{(d)}$ |

-continued

| No | Structure | Synthesis |
|---|---|---|
| 126 | cyclohexyl-NH-C(=O)-NH-(CH₂)₃-pyrrolidinyl | cyclohexyl-N=C=O + H₂N-(CH₂)₃-pyrrolidinyl → (k) |
| 127 | 4-acetylphenyl-O-CH₂-(4-phenyl)-CH₂-piperidinyl | 4'-hydroxyacetophenone + 1,4-bis(bromomethyl)benzene, K₂CO₃ (l); then piperidine (m) |
| 128 | 4-acetylphenyl-O-CH₂-(4-phenyl)-CH₂-pyrrolidinyl | 4'-hydroxyacetophenone + 1,4-bis(bromomethyl)benzene, K₂CO₃ (l); then pyrrolidine (m) |
| 129 | PhCH₂CH₂CH₂-O-CH₂-(4-phenyl)-CH₂-piperidinyl | 4-(piperidinylmethyl)benzyl alcohol + 3-phenylpropyl bromide, NaH (a) |
| 130 | 3-(4-chlorobenzyl)-5-[2-(piperidinyl)ethyl]-1,2,4-oxadiazole | (4-chlorophenyl)-C(=NOH)-NH₂ + piperidine + methyl 4-bromobutanoate (o), (p) |

-continued

| No | Structure | Synthesis |
|---|---|---|
| 131 | benzothiazole-NH-CH2CH2-N(piperidine) | benzothiazole-2-Cl + H2N-CH2CH2-N(piperidine) →(q) |
| 132 | H2N-(CH2)5-N(piperidine) | piperidine-NH + Cl-(CH2)4-CN →(r) then LiAlH4 →(c) |
| 133 | 5-NO2-pyridin-2-yl-NH-(CH2)6-N(piperidine) | HO-(CH2)6-NH2 →(s) with 2-Cl-5-NO2-pyridine; →(t) with piperidine-NH |
| 134 | 3-NO2-pyridin-2-yl-NH-(CH2)6-N(piperidine) | HO-(CH2)6-NH2 →(s) with 2-Cl-3-NO2-pyridine; →(t) with piperidine-NH |
| 135 | pyrimidin-2-yl-NH-(CH2)6-N(piperidine) | HO-(CH2)6-NH2 →(s) with 2-Cl-pyrimidine; →(t) with piperidine-NH |

-continued

| No | Structure | Synthesis |
|---|---|---|
| 136 | 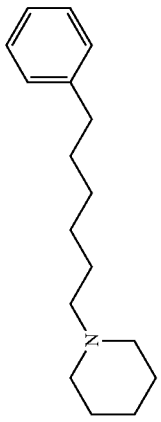 | 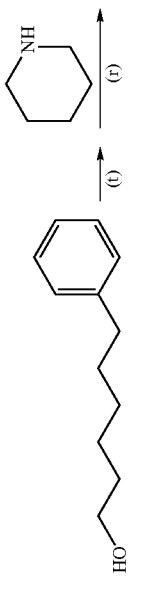 |

(a) toluene, 12 h, r.t.
(b) toluene, tetrabutylammonium iodide, 15-crown-5, 12 h, 80° C.
(c) THF, 12 h, reflux.
(d) acetonitrile, 4 h, 80° C.
(e) ethyl acetate, 3 h, 60° C.
(f) diethyl ether, 2 h, r.t.
(g) $H_2O$/EtOH, 2 h, reflux.
(h) KI, EtOH, 2 d, reflux.
(i) dioxane/$H_2O$ (1 + 1), 4 h, 0° C.
(k) acetonitrile, 5 min, r.t.
(l) acetone/DMF (10:1), 10 min, r.t.
(m) 12 h, r.t.
(n) 1 h, reflux.
(o) triethylamine, acetone, 8 h, 50° C.
(p) Na, MeOH, DMF, 6 h, 80° C.
(q) triethylamine, MeOH, 24 h, 50° C.
(r) $K_2CO_3$, KI, EtOH, 6 h, reflux.
(s) triethylamine, KI, EtOH, 12 h, reflux.
(t) thionyl chloride, THF, 2 h, 0° C.

| No | Structure | Synthesis |
|---|---|---|
| 137 | 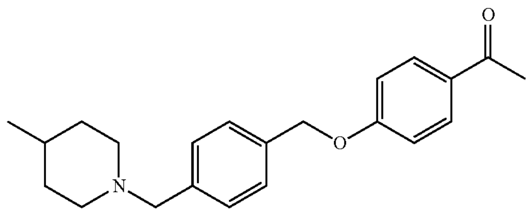 | |
| 138 | cis | |
| 139 | trans | |
| 140 | 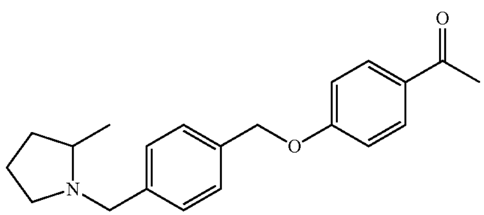 | |

-continued

| No | Structure | Synthesis |
|---|---|---|
| 141 | (cyclopropyl ketone on phenyl-O-CH2-phenyl-CH2-N-piperidine) | HO-C6H4-CH2-OH —NaH (a)→ ; 4-F-C6H4-C(O)-cyclopropyl (c)→ ; (d)→ ; piperidine NH (e)→ |
| 142 | (cyclopropyl ketone on phenyl-O-CH2-phenyl-CH2-N-(4-methylpiperidine)) | HO-C6H4-CH2-OH —NaH (a)→ ; 4-F-C6H4-C(O)-cyclopropyl (c)→ ; (d)→ ; 4-methylpiperidine NH (e)→ |
| 143 | (cyclopropyl ketone on phenyl-O-CH2-phenyl-CH2-N-pyrrolidine) | HO-C6H4-CH2-OH —NaH (a)→ ; 4-F-C6H4-C(O)-cyclopropyl (c)→ ; (d)→ ; pyrrolidine NH (e)→ |
| 144 | (phenyl-(CH2)3-O-(CH2)3-N-(4-methylpiperidine)) | HO-(CH2)3-OH —NaH (b)→ ; H3C-O3S-(CH2)3-phenyl (c)→ ; 4-methylpiperidine NH (e)→ |
| 145 | (phenyl-(CH2)3-O-(CH2)3-N-(3,5-dimethylpiperidine)) cis | HO-(CH2)3-OH —NaH (b)→ ; H3C-O3S-(CH2)3-phenyl (c)→ ; 3,5-dimethylpiperidine NH (e)→ |

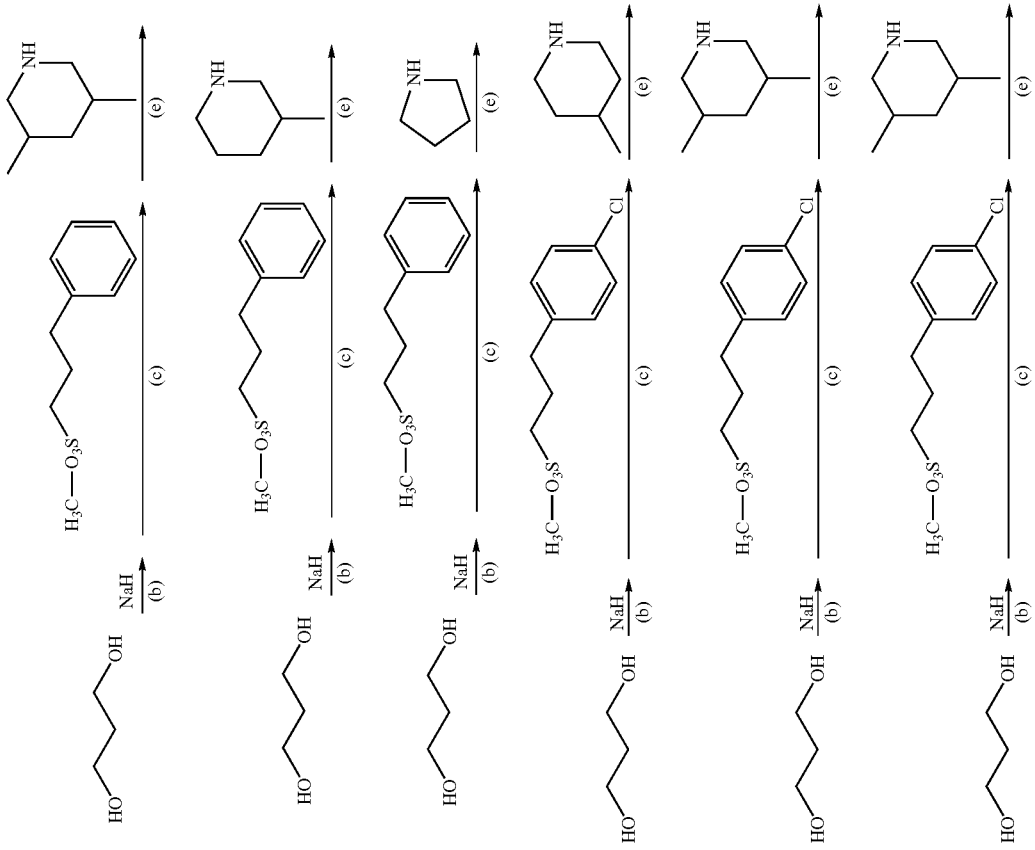

| No | Structure | Synthesis |
|---|---|---|
| 152 | 4-(quinolin-4-ylamino)hexyl-piperidine structure | 4-chloroquinoline + H₂N-(CH₂)₅-OH →(l) →(d) piperidine (e) |
| 153 | 2-methyl-4-(aminopropyl-piperidine)quinoline structure | 2-methyl-4-chloroquinoline + H₂N-(CH₂)₃-OH →(l) →(d) piperidine (e) |
| 154 | 2-methyl-4-(aminohexyl-piperidine)quinoline structure | 2-methyl-4-chloroquinoline + H₂N-(CH₂)₅-OH →(l) →(d) piperidine (e) |
| 155 | 7-chloro-4-(aminopropyl-piperidine)quinoline structure | 7-chloro-4-chloroquinoline + H₂N-(CH₂)₃-OH →(l) →(d) piperidine (e) |
| 156 | 7-chloro-4-(aminobutyl-piperidine)quinoline structure | 7-chloro-4-chloroquinoline + H₂N-(CH₂)₄-OH →(l) →(d) piperidine (e) |

-continued

| No | Structure | Synthesis |
|----|-----------|-----------|
| 157 | 7-chloro-4-(piperidinyl-alkyl-amino)quinoline | piperidine + Br-(CH2)n-Br + phthalimide →(h)→(e)→(i)→ 4,7-dichloroquinoline →(r)→ |
| 158 | 7-chloro-4-(piperidinyl-alkyl-amino)quinoline | piperidine + Br-(CH2)n-Br + phthalimide →(h)→(e)→(i)→ 4,7-dichloroquinoline →(r)→ |
| 159 | 7-chloro-4-(piperidinyl-alkyl-amino)quinoline | piperidine + Br-(CH2)n-Br + phthalimide →(h)→(e)→(i)→ 4,7-dichloroquinoline →(r)→ |
| 160 | 7-chloro-4-[(4-(3-piperidinylpropoxy)phenyl)amino]quinoline | 4-aminophenol + 4,7-dichloroquinoline →(e)→; 1-(3-chloropropyl)piperidine →(o)→ |

| No | Structure | Synthesis |
|---|---|---|
| 161 | 7-chloroquinolin-4-yl aminoethyl-phenoxy-propyl-piperidine | 4-(2-aminoethyl)phenol + 4,7-dichloroquinoline (h); then 1-(3-chloropropyl)piperidine (o) |
| 162 | 1-[4-(3-piperidin-1-yl-propoxy)phenyl]-(piperidinyl)pentanone | 3-(3-bromophenoxy)propyl + piperidine (e); 5-chloro-5-oxopentanoyl chloride (m); piperidine (e) |
| 163 | 5-nitro-N-(5-piperidin-1-yl-pentyl)pyridin-2-amine | 5-aminopentan-1-ol + 2-chloro-5-nitropyridine (l); (d); piperidine (e) |
| 164 | 3-nitro-N-(5-piperidin-1-yl-pentyl)pyridin-2-amine | 5-aminopentan-1-ol + 2-chloro-3-nitropyridine (l); (d); piperidine (e) |
| 165 | 5-amino-N-(5-piperidin-1-yl-pentyl)pyridin-2-amine | 5-aminopentan-1-ol + 2-chloro-5-nitropyridine (l); (d); piperidine (e); (q) |

| No | Structure | Synthesis |
|---|---|---|
| 166 | | |
| 167 | | |
| 168 | | |
| 169 | | |

-continued

| No | Structure | Synthesis |
|---|---|---|
| 170 | 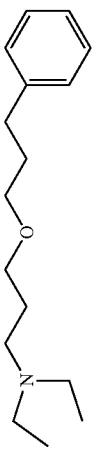 | 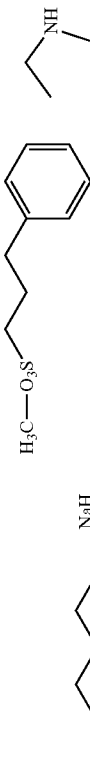 |

(a) THF, 10 h, r.t.
(b) THF, 10 h, reflux
(c) THF, tetrabutylammonium iodide, 15-crown-5, 24 h, reflux
(d) thionyl chloride, 3 h, 0° C.–70° C.
(e) acetone, KI, 12 h, reflux
(f) acetone, 10 min., r.t.
(g) acetone, 12 h, reflux
(h) acetone, KI, 3 d, reflux
(i) 6N HCl, 12 h, reflux
(k) ether, 2 h, r.t.
(l) ethanol, KI, triethylamine, 12 h, reflux
(m) nitrobenzol, AlCl₃, 3 d, r.t.
(n) DMF, KI, K₂CO₃, 22 h, reflux
(o) acetone, KI, K₂CO₃, 22 h, reflux
(p) ethanol, KI, 6 d, reflux
(q) THF, Pd/C, 1 bar, 12 h
(r) phenol, KI, 12 h, 150° C.

The following compounds can be prepared according to the synthesis schemes:

| No. | Structure | Synthesis |
|---|---|---|
| 171 | N-(3-(N,N-Diethylamino)propyl)N'-phenylurea | scheme 7 |
| 172 | N-Cyclohexylmethyl-N'-(3-piperidinopropyl)guanidine | scheme 7 |
| 173 | N-(4-Bromobenzyl)-N'-(4-piperidinobutyl)sulphamide | scheme 12 |
| 174 | 3-Chloro-N-(4-piperidinobutyl)-N-methyl-benzene sulphonamide | scheme 12 |
| 175 | N-(4-Chlorobenzyl)-2-(4-piperidinomethyl)phenyl) ethan amidine | scheme 11 |
| 176 | 1-(5-Cyclohexylpentanoyl)-1,4-bipiperidine | scheme 9 |
| 177 | cis-1-(6-Cyclohexyl-3-hexen-1-yl)piperidine | |

| No. | Structure | Synthesis |
|---|---|---|
| 178 | trans-1-(6-Cyclohexyl-3-hexen-1-yl)piperidine | (u) (v) |
| 179 | 1-(6-Cyclohexyl-3-hexin-1-yl)piperidine | (w) |
| 180 | 1-(2-(5,5-Dimethyl-1-hexin-1-yl)cyclopropyl)piperidine | scheme 14 |

(u) potassium tert. butanolate, THF, 24 h, 0–50° C.; (v) chromatographic separation; (w) NH$_3$ (fl.), MeOH, −78–0° C.

Compounds 1 to 114 are prepared according to the following procedures:

Method A:

A solution of 1-bromo-5-phenoxypentane (1.4 to 3.5 mmol) in ten equivalents of the suitable secondary amine was heated to reflux temperature with stirring for 48 hours (compds. 1, 3 and 4), 24 hours (compd. 2) or 4 hours (compd. 5). After cooling, the excess base was removed under reduced pressure and the residue diluted with aqueous sodium hydroxide. The product was extracted with diethyl ether, the organic extracts washed with water, dried over magnesium sulphate, filtered and concentrated under reduced pressure. The remaining oil was converted to oxalate salt by dissolving in a small amount of absolute ethanol and adding a solution of two equivalents oxalic acid in absolute ethanol. The precipitate formed was washed with diethyl ether and recrystallised from absolute ethanol.

Method B:

A solution of 1-bromo-5-phenoxypentane (0.9 to 1.7 mmol) and an excess of the suitable secondary amine (2.3 to 10 equivalents) in 10 ml absolute ethanol was heated to reflux temperature with stirring for 48 hours (compd. 6) or 24 hours (compds. 7, 8, 9, 10, 11, 12&13, 14, 15, 16, 17 and 29). After cooling, the solvent was removed under reduced pressure and the residue diluted with aqueous sodium hydroxide. The product was extracted with diethyl ether, the organic extracts washed with water, dried over magnesium sulphate, filtered and concentrated under reduced pressure. The cis and trans isomers 12 and 13 were separated by column chromatography on silica gel eluting with a solvent mixture of petroleum spirit (bp 60–80° C.), diethyl ether and triethylamine in the ratio 66:33:1, and the eluent was removed under reduced pressure to leave an oil. Compounds 14 and 16 were purified by column chromatography on silica gel eluting with diethyl ether and triethylamine in the ratio 99:1, and the eluent was removed under reduced pressure to leave an oil. The oil was converted to oxalate salt (compds. 6, 7, 8, 9, 11, 12, 13, 15, 16, 17 and 29) by dissolving in a small amount of absolute ethanol and adding a solution of two equivalents of oxalic acid in absolute ethanol. If no precipitate appeared, diethyl ether was added to form a precipitate. The solid was washed with diethyl ether and recrystallised from isopropyl alcohol (compds. 6, 7, 10, 13 and 16), absolute ethanol (compds. 8, 9, 11, 12, 15 and 29) or methanol (compd. 17). The oil was converted to hydrochloride salt (compd. 14) by adding 2N HCl. The precipitate was formed in a mixture of chloroform and diethyl ether (1:1) and recrystallised from acetone.

Method C:

A solution of the suitable α-bromo-ω-aryloxy alkane (0.4 to 1.4 mmol) or ω-bromoalkyl phenyl sulphide (1 mmol, compds. 33 and 34) and an excess of pyrrolidine (10 to 15 equivalents) or 3-methylpiperidine (10 equivalents, compd. 38) in 10 ml absolute ethanol was heated to reflux temperature with stirring for 24 hours or 16 hours (compd. 47). After cooling, the solvent was removed under reduced pressure and the residue diluted with aqueous sodium hydroxide. The product was extracted with diethyl ether, the organic extracts washed with water, dried over magnesium sulphate, filtered and concentrated under reduced pressure. The remaining oil was converted to oxalate salt by dissolving in a small amount of absolute ethanol and adding a solution of two equivalents oxalic acid in absolute ethanol. If no precipitate appeared, diethyl ether was added to form a precipitate. The solid was washed with diethyl ether and recrystallised from absolute ethanol.

Method D:

A solution of the suitable 4'-(5-bromopentoxy)phenyl ketone (0.7 to 1 mmol, compds. 39, 44 and 45) or 1-bromo, 5-(4-phenoxyphenoxy)pentane (0.6 mmol, compd. 48) and an excess of pyrrolidine (10 to 15 equivalents) in 10 ml absolute ethanol was heated to reflux temperature with stirring for 16 hours (compds. 39, 44 and 48) or 24 hours (compd. 45). After cooling, the solvent was removed under reduced pressure and the residue diluted with aqueous sodium hydroxide. The product was extracted with chloroform (compds. 39, 45 and 48) or dichloromethane (compd. 44), the organic extracts dried over magnesium sulphate, filtered and concentrated under reduced pressure. The remaining oil was converted to oxalate salt by dissolving in a small amount of absolute ethanol and adding a solution of two equivalents oxalic acid in absolute ethanol. The precipitate was washed with diethyl ether and recrystallised from absolute ethanol (recrystallised twice from absolute ethanol in the case of compd. 39).

Method E:

1. The oxalate 18 was prepared according to method C. A solution of compound 18 (0.57 mmol) in 10 ml methanol and 10 ml absolute ethanol was placed with 100 mg of palladium (5%) on carbon catalyst in a two-neck round-bottom flask fitted with a balloon filled with hydrogen. The mixture was stirred vigorously at room temperature and the flask was purged of air and filled with hydrogen. After 3 hours, the catalyst was filtered off on celite and the solvent removed under reduced pressure. The residual solid was converted to oxalate salt by dissolving in methanol and adding a solution of oxalic acid (2 equivalents) in absolute ethanol. Diethyl ether was added to form a precipitate. The product was recrystallised from absolute ethanol.

2. To a solution of compound 40 (0.35 mmol) in pyridine vigorously stirred at 0° C. was added dropwise a slight excess of benzoyl chloride (0.4 mmol). The stirring was allowed to continue 20 minutes after the end of the addition after which the mixture was placed in the refrigerator overnight (16 hours). The solvent was removed under reduced pressure and the residue diluted with aqueous sodium hydroxide. The product was extracted with chloroform, the organic extracts dried over magnesium sulphate, filtered and concentrated under reduced pressure. The remaining oil was converted to oxalate salt by dissolving in a small amount of absolute ethanol and adding a solution of two equivalents oxalic acid in absolute ethanol. The precipitate was dissolved in methanol, filtered, and concentrated under reduced pressure, the solid was recrystallised from absolute ethanol Method F:

In a three-neck flask kept under nitrogen was placed a solution of the suitable phenol (1.6 mmol), 3-(diethylamino)propanol (1.5 mmol), and triphenyl phosphine (1.9 mmol) in 10 ml freshly distilled tetrahydrofuran. The mixture was stirred and cooled to 0° C. with an ice and salt bath. A solution of diisopropyl azodicarboxylate (2 mmol) in 10 ml tetrahydrofuran was added very slowly (typically over 40 minutes) and the mixture was allowed to warm to room temperature after which it was stirred overnight at room temperature (16 hours). The solvent was then removed under reduced pressure, the residue dissolved in ethyl acetate (20 ml) and the product extracted with 2N HCl (2×10 ml). The aqueous solution was neutralised with sodium hydroxide and the product extracted with dichloromethane. After drying over magnesium sulphate and filtration, the solvent was removed under reduced pressure. The residue was converted to oxalate salt by dissolving in a small amount of absolute ethanol and adding a solution of two equivalents oxalic acid in absolute ethanol. If no precipitate appeared, diethyl ether was added to form a precipitate. The solid was washed with diethyl ether and recrystallised from absolute ethanol (compds. 43 and 46) or from a 1:1 mixture of methanol and absolute ethanol (compd. 42).

Method G:

A solution of the free base of compound 39 (0.6 mmol) or compound 46 (0.8 mmol) in 20 ml dry diethyl ether was added dropwise to a stirred suspension of lithium aluminium hydride (0.6 or 0.8 mmol) in 20 ml dry diethyl ether kept under nitrogen. The mixture was stirred at room temperature under nitrogen for two hours. Ice-cold water was carefully added and the organic layer decanted. The aqueous phase was extracted with diethyl ether. The combined organic solutions were dried over magnesium sulphate, filtered and concentrated under reduced pressure to leave a yellow oil. The oil was converted to oxalate salt by dissolving in a small amount of absolute ethanol and adding a solution of two equivalents oxalic acid in absolute ethanol. The precipitate was washed with diethyl ether and recrystallised from absolute ethanol (compd 50) or from isopropyl alcohol, giving a very hygroscopic solid (compd. 63).

Method H:

A solution of the suitable α-bromo-ω-(4-cyanophenoxy)alkane (0.5 to 0.7 mmol) and an excess of the suitable secondary amine (8 to 12 equivalents) in 10 ml absolute ethanol was heated to reflux temperature with stirring for 24 hours (compds. 54, 55, 57 and 60), 20 hours (compd. 52), 16 hours (compds. 56, 58, 59 and 61) or 8 hours (compd. 51) or was stirred at room temperature for 48 hours (compd. 53) or 24 hours (compd. 60). After cooling, the solvent was removed under reduced pressure and the residue diluted with aqueous sodium hydroxide. The product was extracted with diethyl ether, the organic extracts washed with water, dried over magnesium sulphate, filtered and concentrated under reduced pressure. Compound 62 was purified by column chromatography on silica gel eluting with ethyl acetate, and concentrated under reduced pressure. For all the compounds of method H, the remaining oil was converted to oxalate salt by dissolving in a small amount of absolute ethanol and adding a solution of two equivalents oxalic acid in absolute ethanol. If no precipitate appeared, diethyl ether was added to form a precipitate. The solid was washed with diethyl ether and recrystallised from absolute ethanol (two recrystallisations were required for compds. 58 and 59) or from a 1:1 mixture of methanol and absolute ethanol (compd. 55).

Method J:

A solution of compound 46 (1 mmol) in 10 ml methanol was stirred at room temperature and a solution of hydroxylamine hydrochloride (2 equivalents) in 2 ml water was added. The mixture was stirred at 50–70° C. in a water bath for 20 minutes. Methanol was removed under reduced pressure. The residue diluted with aqueous sodium hydroxide. The product was extracted with diethyl ether, the organic extracts washed with water, dried over magnesium sulphate, filtered and concentrated under reduced pressure. Compound 64 was purified by column chromatography on silica gel eluting with ethyl acetate, and concentrated under reduced pressure. The remaining oil was converted to oxalate salt by dissolving in a small amount of absolute ethanol and adding a solution of two equivalents oxalic acid in absolute ethanol. Diethyl ether was added to form a precipitate. The solid was washed with diethyl ether and recrystallised from absolute ethanol.

For example 98, the product was converted to the hydrochloride salt by addition of 2N HCl. The salt was recrystallised from absolute ethanol/diethyl ether (1:1).

Method K:

A solution of 4'-(3-bromopropoxy)acetophenone (0.8 to 1.9 mmol) and an excess of the suitable piperidine (3 to 10 equivalents) in 10 ml absolute ethanol was heated to reflux temperature with stirring for 16 hours. After cooling, the solvent was removed under reduced pressure and the residue diluted with aqueous sodium hydroxide. The product was extracted with diethyl ether, the organic extracts washed with water, dried over magnesium sulphate, filtered and concentrated under reduced pressure. The cis and trans isomers 67 and 70 were separated by column chromatography on silica gel eluting with a solvent mixture of diethyl ether, petroleum spirits (bp 60–80° C.) and triethylamine in the ratio 66:33:1, and the eluent was removed under reduced pressure to leave an oil. Compound 75 was purified by column chromatography on silica gel eluting with chloroform and methanol (1:1), and concentrated under reduced pressure. The remaining oil was converted to oxalate salt by dissolving in a small amount of absolute ethanol and adding a solution of two equivalents of oxalic acid in absolute ethanol. If no precipitate appeared, diethyl ether was added to form a precipitate. The solid was washed with diethyl ether and recrystallised from absolute ethanol.

Method L:

In a three-neck flask kept under nitrogen was placed a solution of the suitable 4'-hydroxyphenyl ketone (0.9 to 3 mmol), 3-(1-piperidinyl)propanol (0.9 to 3 mmol), and triphenyl phosphine (1 to 3.5 mmol) in 10 ml freshly distilled tetrahydrofuran. The mixture was stirred and cooled to 0° C. with an ice and salt bath. A solution of diethyl azodicarboxylate (1 to 3.6 mmol) in 10 ml tetrahydrofuran was added very slowly (typically over 40 minutes) and the mixture was allowed to warm to room temperature after which it was stirred overnight at room temperature (16 hours). The solvent was then removed under reduced pressure, the residue dissolved in ethyl acetate (20 ml) and the product extracted with 2N HCl (2×10 ml). The aqueous solution was neutralised with sodium hydroxide and the product extracted with dichloromethane. After drying over magnesium sulphate and filtration, the solvent was removed under reduced pressure. The crude product was purified by column chromatography on silica gel eluting with diethyl ether containing 1% triethylamine, and concentrated under reduced pressure. The residue was converted to oxalate salt by dissolving in a small amount of absolute ethanol and adding a solution of two equivalents oxalic acid in absolute ethanol. If no precipitate appeared, diethyl ether was added to form a precipitate. The solid was washed with diethyl ether and recrystallised from absolute ethanol.

For example 82, the amine was converted to the hydrochloride salt by addition of 2N HCl. The salt was recrystallised from absolute ethanol/diethyl ether (1:14).

Method M:

A solution of 3-(4-acetylphenoxy)-2-(R or S)-methylpropyl para-toluene sulfonate (0.55 to 0.66 mmol) and piperidine (5 to 6 mmol) in 10 ml absolute ethanol was stirred and heated under reflux for 2 hours. After cooling, the solvent was removed under reduced pressure, the residue diluted with aqueous NaOH (10 ml) and the oil was extracted with diethyl ether (3×10 ml). The combined extracts were dried over magnesium sulfate, and the solvent removed under reduced pressure. The yellow oil was purified by column chromatography on silica gel eluting with a 1:1 mixture of chloroform and absolute ethanol (example 80). After concentration, the oil was dissolved in about 2 ml absolute ethanol and a solution of oxalic acid (1 to 1.1 mmol) in 2 ml absolute ethanol was added. The precipitate was recrystallised from absolute ethanol.

Method N:

A solution of 1-bromo-3-(4-substitutedphenoxy)propane (0.4 to 2 mmol) and the suitably substituted piperidine (2.5 to 8 mmol) in 10 ml absolute ethanol was stirred and heated under reflux for 6 to 24 hours. After cooling, the solvent was removed under reduced pressure, the residue diluted with aqueous NaOH (10 ml) and the oil was extracted with diethyl ether (3×10 ml). The combined extracts were dried over magnesium sulfate, and the solvent removed under reduced pressure. The residual oil was dissolved in about 5 ml diethyl ether and a solution of HCl in 10 ml diethyl ether was added. The precipitate was recrystallised from a 1:1 or 1:5 mixture of absolute ethanol and diethyl ether (examples 78, 79, 84, 87). The oil was purified by column chromatography on silica gel eluting with a mixture of 33% petroleum ether (60–80° C.), 66% diethyl ether and 1% triethylamine (examples 101 and 102) or with 99% diethyl ether and 1% triethylamine (examples 88, 94 and 95) and concentrated. The residual oil was dissolved in about 5 ml absolute ethanol and a solution of oxalic acid (1 to 1.6 mmol) in 5 ml absolute ethanol was added. The precipitate was recrystallised from absolute ethanol or from a 1:1 mixture of methanol and absolute ethanol (examples 83, 85, 86, 91, 93, 100, 101 and 102). The product was obtained as a sticky oil after removal of absolute ethanol (example 92).

Method O:

A mixture of 4-(4-hydroxyphenyl)-2-butanone (200 mg, 1.2 mmol), 3-chloropropyl piperidine hydrochloride (200 mg, 1 mmol) and potassium carbonate (830 mg, 6 mmol) in 10 ml absolute ethanol was stirred and heated under reflux for 8 hours. After cooling, the reaction mixture was filtered and concentrated under reduced pressure. The residue was diluted with aqueous sodium hydroxide and extracted with diethyl ether (3×10 ml). The combined extracts were dried over magnesium sulfate, and the solvent removed under reduced pressure. The free base was dissolved in diethyl ether and a solution of HCl in diethyl ether was added. The precipitate was recrystallised from acetone.

Method P:

A solution of the ketone (0.4 mmol) in 10 ml methanol was stirred at 0° C. in an ice-bath. To this solution was added portionwise NaBH$_4$ (1 mmol). The mixture was left to stir at room temperature for 16 hours. The solvent was removed, water (10 ml) was added to the residue and the product was extracted with chloroform (4×10 ml). The combined extracts were dried over magnesium sulfate, and the solvent removed under reduced pressure. The free base was dissolved in absolute ethanol (5 ml) and a solution of oxalic acid (1 mmol) in 5 ml absolute ethanol was added. The precipitate was recrystallised from absolute ethanol.

Method Q:

Similar to method J using methoxy]amine in place of hydroxylamine. For example 105, the product was converted to the hydrochloride salt by addition of 2N HCl. The salt was recrystallised from absolute ethanol/diethyl ether (1:3).

Method R:

Similar to method P. The reduced product was converted to the hydrochloride salt by addition of 2N HCl. Then, the product was converted to the free base by addition of 10% aqueous NaOH. Then, the product was converted to the para-toluene sulfonate by addition of a solution of para-toluene sulfonic acid (1 mmol) in 5 ml absolute ethanol. The precipitate was recrystallised from absolute ethanol/diethyl ether (1:3).

Method S:

Similar to method P. The reduced product was converted to the para-toluene sulfonate by addition of a solution of para-toluene sulfonic acid (1 mmol) in 5 ml absolute ethanol. The precipitate was recrystallised from absolute ethanol/diethyl ether (1:3).

Intermediates:

(4-hydroxyphenyl)cyclopropyl ketone, intermediate for examples 76, 101 and 102.

S. N. Rastogi et al. *J. Med. Chem.* 15, 286–291 (1972)

4'-(3-hydroxy-2-(R)-methylpropoxy)acetophenone and 4'-(3-hydroxy-2-(S)methylpropoxy) acetophenone, intermediates for examples 77 and 80.

A mixture of 4'-hydroxyacetophenone (1.3 to 2.8 mmol), 3-bromo-2-(R or S)methyl-1-propanol (1.3 to 2.6 mmol) and potassium carbonate (1.7 to 3.6 mmol) in acetone (20 ml) was stirred and heated under reflux for 24 hours. The suspension was filtered hot and the solvent removed under reduced pressure to leave an oil that was purified by column chromatography on silica gel eluting with a mixture of diethyl ether and petroleum ether (60–80° C.). After concentration, a colourless oil was obtained.

NMR: 7.91 (m, 2H); 6.92 (m, 2H); 4.01 (m, 2H); 3.71 (br, 2H); 2.54 (s, 3H); 2.21 (m, 1H); 2.10 (br, 1H); 1.06 (d, 3H)

NMR: 7.91 (m, 2H); 6.93 (m, 2H); 4.01 (m, 2H); 3.71 (br, 2H); 2.55 (s, 3H); 2.23 (m, 1H); 2.09 (br, 1H); 1.06 (d, 3H)

3-(4-acetylphenoxy)-2-(S)-methylpropyl para-toluene sulfonate and 3-(4-acetylphenoxy)-2-(R)-methylpropyl para-toluene sulfonate, intermediates for examples 77 and 80.

A solution of 4'-(3-hydroxy-2-(R or S)-methylpropoxy)acetophenone (0.7 to 1.2 mmol) in pyridine (5 ml) was stirred at 0° C. and para-toluene sulfonyl chloride (1 to 1.6 mmol) was added portionwise. The mixture was subsequently placed in the refrigerator overnight. The solvent was then removed under reduced pressure and the residue purified by column chromatography on silica gel eluting with a mixture of 50% diethyl ether and 50% petroleum ether 60–80° C. After concentration, a colourless oil was obtained. In the case of the R-isomer, the oil formed a white solid that was recrystallised from absolute ethanol.

NMR: 7.91 (m, 2H); 7.74 (m, 2H); 7.23 (m, 2H); 6.79 (m, 2H); 4.11 (m, 2H); 3.87 (m, 2H); 2.57 (s, 3H); 2.38 (s, 3H); 2.33 (m, 1H); 1.07 (d, 3H)

NMR: 7.88 (m, 2H); 7.71 (m, 2H); 7.21 (m, 2H); 6.75 (m, 2H); 4.07 (m, 2H); 3.83 (m, 2H); 2.53 (s, 3H); 2.34 (s, 3H); 2.30 (m, 1H); 1.04 (d, 3H)

1-bromo-3-(4-nitrophenoxy)propane, intermediate for examples 83, 85 and 86.

J. N. Ashley et al. *J. Chem. Soc.* 3298–3304 (1958)

1-bromo-3-(4-propionylphenoxy)propane, intermediate for examples 88, 94 and 95.

To a stirred and heated mixture of 1,3-dibromopropane (80 mmol) and potassium carbonate (50 mmol) in acetone (200 ml) was added dropwise a solution of the hydroxy ketone (40 mmol) in acetone (80 ml). The reaction was allowed to continue overnight. The mixture was filtered hot and the solvent removed under reduced pressure to leave an oil that was dissolved in ethyl acetate. Addition of petroleum spirit (60–80° C.) formed a precipitate. The solid was filtered and dried under reduced pressure.

NMR: 7.96 (m, 2H); 6.93 (m, 2H); 4.18 (t, 2H); 3.62 (t, 2H); 2.96 (q, 2H); 2.34 (m, 2H); 1.22 (t, 3H)

(4-hydroxyphenyl)cyclobutyl ketone and (4-hydroxyphenyl)cyclopentyl ketone, intermediates for examples 89 and 90.

A mixture of cyclobutylcarbonyl chloride (5 mmol) or cyclopentylcarbonyl chloride (7 mmol) and aluminium chloride (15 mmol) in dry dichloromethane (40 ml) was stirred at 0° C. and a solution of phenol (8 mmol) in dry dichloromethane (20 ml) was added dropwise, the mixture was then stirred and heated under reflux for 3 hours. After cooling to 0° C., water was added with vigorous stirring. The organic layer was decanted off, dried over magnesium sulfate and concentrated. The crude product was purified by column chromatography on silica gel eluting with petroleum ether/diethyl ether (2:1).

NMR: 7.72 (m, 2H); 6.80 (m, 2H); 3.95 (m, 1H); 2.45 (m, 2H); 2.15 (m, 4H)

NMR: 7.92 (m, 2H); 7.25 (s, 1H); 6.92 (m, 2H); 3.70 (m, 1H); 2.00 (m, 4H); 1.75 (m, 4H)

1-bromo-3-(4-cyclopropanecarbonylphenoxy)propane, intermediate for examples 101 and 102.

To a stirred and heated mixture of 1,3-dibromopropane (5 mmol) and potassium carbonate (3.4 mmol) in acetone (40 ml) was added dropwise a solution of 4-cyclopropanecarbonylphenol (5 mmol) in acetone (20 ml). The reaction was allowed to continue overnight. The mixture was filtered hot and the solvent removed under reduced pressure to leave an oil. The oil was purified by column chromatography on silica gel eluting with petroleum ether/ethyl acetate (15:1).

4-(N,N-dimethylsulfonamido)phenol, intermediate for example 110.

N. Eliel *J. Org. Chem.* 20, 1657–1660 (1955)

Compounds 115 to 170 are prepared according to the following procedures:

Example 115

3,3-Dimethylbutyl 3-piperidinopropylether

Sodium 3-piperidinopropanolate (5 mmol), 5 mmol of 3,3-dimethylbutyl chloride, a catalytic amount of tetrabutylammonium iodide, and 0.5 mmol of 15-crown-5 in 10 ml of dry dimethyl sulfoxide were refluxed for 12 hours. Water was added, and it was extracted with diethyl ether. The organic layer was purified by column chromatography on silica gel (eluent: methylene chloride/methanol (90/10), ammonia atmosphere). The solvent was removed under reduced pressure and the residue crystallized with oxalic acid from diethyl ether/ethanol.

| SF: $C_{14}H_{29}NO \times 1.1\ C_2H_2O_4$ (326.4) mp: 143° C. | | | | | | | |
|---|---|---|---|---|---|---|---|
| CHN analysis | calculated: | C | 59.6 | H | 9.63 | N | 4.29 |
|  | found: | C | 59.7 | H | 9.61 | N | 4.30 |

Example 116

3-Phenylpropyl 3-piperidinopropylether

Sodium 3-piperidinopropanolate (20 mmol), 20 mmol of 3-phenylpropyl bromide, and 0.5 mmol of 15-crown-5 in 30 ml of dry toluene were refluxed for 4 hours. The solvent was evaporated and the residue purified by column chromatography on silica gel (eluent: methylene chloride/methanol/ aqueous ammonia (90/10/0.5)). After removing the solvent under reduced pressure the residue was crystallized with oxalic acid from diethyl ether/ethanol.

| SF: $C_{17}H_{27}NO \times C_2H_2O_4$ (351.4) mp: 125° C. | | | | | | | |
|---|---|---|---|---|---|---|---|
| CHN analysis | calculated: | C | 64.9 | H | 8.32 | N | 3.99 |
|  | found: | C | 64.9 | H | 8.13 | N | 4.02 |

Example 117

3-(4-Chlorophenyl)propyl 3-piperidinopropylether

Sodium 3-piperidinopropanolate (20 mmol), 7 mmol of 3-(4-chlorophenyl)propyl-mesylate, and 0.5 mmol of 15-crown-5 in 30 ml of dry toluene were refluxed for 4 hours. The solvent was evaporated and the residue purified by column chromatography on silica gel (eluent: methylene chloride/methanol (90/10)). After removing the solvent under reduced pressure the residue was crystallized with oxalic acid from diethyl ether/ethanol.

| SF: $C_{17}H_{26}NOCl \times C_2H_2O_4$ (385.9) mp: 147° C. | | | | | | | |
|---|---|---|---|---|---|---|---|
| CHN analysis | calculated: | C | 59.1 | H | 7.31 | N | 3.63 |
|  | found: | C | 59.0 | H | 7.34 | N | 3.60 |

Example 118

2-Benzothiazolyl 3-piperidinopropylether

Sodium 3-piperidinopropanolate (5 mmol) and 5 mmol of 2-chlorobenzothiazole in 20 ml of dry tetrahydrofurane were refluxed for 12 hours. The suspension was filtered and the solvent evaporated under reduced pressure. The product was crystallized with oxalic acid from diethyl ether/ethanol.

| SF: $C_{15}H_{20}N_2OS \times C_2H_2O_4$ (366.4) mp: 178.2–178.8° C. | | | | | | | |
|---|---|---|---|---|---|---|---|
| CHN analysis | calculated: | C | 55.7 | H | 6.05 | N | 7.64 |
|  | found: | C | 55.6 | H | 6.03 | N | 7.51 |

Example 119

N-Phenyl-3-piperidinopropyl carbamate

3-Piperidinopropanol hydrochloride (10 mmol) and 10 mmol of phenyl isocyanate in 40 ml of dry acetonitrile were refluxed for 3 hours. The solvent was evaporated, and then the residue was recrystallized in dry ethanol.

| SF: $C_{15}H_{22}N_2O_2 \times HCl \times 0.1\ H_2O$ (300.6) mp: 169–170° C. | | | | | | | |
|---|---|---|---|---|---|---|---|
| CHN analysis | calculated: | C | 59.9 | H | 7.78 | N | 9.32 |
|  | found: | C | 59.9 | H | 7.64 | N | 9.05 |

Example 120

N-Pentyl-3-piperidinopropyl carbamate

3-Piperidinopropanol hydrochloride (4 mmol) and 4 mmol of pentyl isocyanate in 20 ml of dry acetonitrile were refluxed for 3 hours. The solvent was evaporated and the residue purified by column chromatography on silica gel (eluent: methylene chloride/methanol/aqueous ammonia (90/10/0.5)). After removing the solvent under reduced pressure the residue was crystallized with hydrochloric acid in 2-propanol.

| SF: $C_{14}H_{28}N_2O_2 \times HCl \times 0.5\ H_2O$ (301.9) mp: 88–89° C. | | | | | | | |
|---|---|---|---|---|---|---|---|
| CHN analysis | calculated: | C | 55.7 | H | 10.0 | N | 9.28 |
|  | found: | C | 55.7 | H | 9.84 | N | 9.18 |

Example 121

(S)-(+)-N-[2-(3,3-Dimethyl)butyl]-3-piperidinopropyl carbamate

3-Piperidinopropanol hydrochloride (5 mmol) and 5 mmol of (S)-2-(3,3-dimethyl)butyl isocyanate in 10 ml of dry acetonitrile were refluxed for 12 hours. The solvent was evaporated and the residue purified by column chromatography on silica gel (eluent: methylene chloride/methanol (90/10), ammonia atmosphere). The solvent was removed and the residue crystallized with oxalic acid from diethyl ether/ethanol.

| SF: $C_{15}H_{30}N_2O_2 \times C_2H_2O_4 \times 0.25\ H_2O$ (365.0) mp: 148° C. $[\alpha]_D^{23} = +10.4°$ (c = 0.495, Methanol) | | | | | | | |
|---|---|---|---|---|---|---|---|
| CHN analysis | calculated: | C | 56.0 | H | 8.98 | N | 7.68 |
|  | found: | C | 56.0 | H | 9.01 | N | 7.64 |

Example 122

N-(4-Chlorobenzyl)-S-(3-piperidinopropyl)isothiourea

4-Chlorobenzylamine (10 mmol) was added dropwise to 10 mmol of benzoylisothiocyanate dissolved in 20 ml of dry ether followed by stirring for 2 hours. The precipitated product was filtered off and crystallized from ethyl acetate (Yield: 60%). Potassium carbonate (10 mmol) in 30 ml of water was added dropwise to 5 mmol of the product in 20 ml of ethanol and refluxed for 2 hours. The precipitated product was filtered off and crystallized from ethyl acetate/petroleum ether (Yield: 65%). 3-Piperidinopropyl chloride hydrochloride (3 mmol), 3 mmol of the product, and a catalytic amount of potassium iodide were refluxed in 20 ml of ethanol for 2 days. Subsequently the ethanol was evaporated and the residue purified by column chromatography using methanol/ethyl acetate (2/8) as eluent. After evaporation of the solvent, the product was crystallized with hydrochloric acid from diethyl ether/ethanol.

| SF: $C_{16}H_{24}ClN_3S \times 2\ HCl \times H_2O$ (416.8) mp: 104–107.5° C. | | | | | | | |
|---|---|---|---|---|---|---|---|
| CHN analysis | calculated: | C | 46.1 | H | 6.77 | N | 10.1 |
|  | found: | C | 45.9 | H | 6.87 | N | 9.69 |

Example 123

N'-Cyclohexylthiocarbamoyl-N-1,4'-bipiperidine 1,4'-Bipiperidine (5 mmol) in 10 ml of dry ether was added dropwise to 5 mmol of cyclohexyl isothiocyanate in 30 ml of dry ether followed by stirring for 2 hours. Filtration gave a residue, which was dissolved in ethanol and crystallized with oxalic acid. Recrystallization resulted in the pure product.

| SF: $C_{17}H_{31}N_3S \times H_2C_2O_4 \times 0.25\ H_2O$ (404.1) mp: 225–226° C. | | | | | | | |
|---|---|---|---|---|---|---|---|
| CHN analysis | calculated: | C | 56.5 | H | 8.35 | N | 10.39 |
|  | found: | C | 56.2 | H | 8.25 | N | 10.33 |

Example 124

N-Heptanoyl-1,4'-bipiperidine 1,4'-Bipiperidine (10 mmol) in 5 ml of water was added dropwise to a solution of 5 mmol of n-heptanoyl chloride in 20 ml of dioxane. After stirring for 15 minutes the solvent was evaporated under reduced pressure and the residue purified by column chromatography on silica gel (eluent: methylene chloride/methanol/aqueous ammonia (90/10/0.5)). The solvent was removed under reduced pressure, and the residue was crystallized with oxalic acid.

| SF: $C_{17}H_{32}N_2O \times H_2C_2O_4$ (370.5) mp: 131–132° C. | | | | | | | |
|---|---|---|---|---|---|---|---|
| CHN analysis | calculated: | C | 61.6 | H | 9.25 | N | 7.56 |
|  | found: | C | 61.6 | H | 9.36 | N | 7.50 |

Example 125

3-Cyclopentyl-N-(3-(1-pyrrolidinyl)propyl)propanamide

3-Cyclopentyl propionylchloride (5 mmol) in 10 ml of dioxane was added dropwise to a solution of 10 mmol of 1-(3-aminopropyl)pyrrolidine in water. After stirring for 4 hours the solvent was evaporated under reduced pressure and the residue purified by column chromatography on silica gel (eluent: methylene chloride/methanol/aqueous ammonia (90/10/1)). The solvent was removed under reduced pressure and the residue was crystallized with oxalic acid from diethyl ether/ethanol.

| SF: $C_{17}H_{28}N_2O \times H_2C_2O_4 \times 0.5\ H_2O$ (351.2) mp: 89.5° C. | | | | | | | |
|---|---|---|---|---|---|---|---|
| CHN analysis | calculated: | C | 58.1 | H | 8.83 | N | 7.97 |
|  | found: | C | 58.1 | H | 8.76 | N | 7.87 |

Example 126

N-Cyclohexyl-N'-(1-pyrrolidinyl-3-propyl)urea

In an argon atmosphere 10 mmol of cyclohexylisocyanate was added slowly to 10 mmol of 1-(3-aminopropyl)pyrrolidine in 10 ml of acetonitrile. The product precipitated instantly as a pure white solid. The solvent was removed under reduced pressure and the product was crystallized with oxalic acid from diethyl ether/ethanol.

| SF: $C_{14}H_{27}N_3O \times C_2H_2O_4 \times 0.25\ H_2O$ (347.7) Yield: 83% mp: 113.3° C. | | | | | | | |
|---|---|---|---|---|---|---|---|
| CHN analysis | calculated: | C | 56.0 | H | 8.45 | N | 12.2 |
|  | found: | C | 55.6 | H | 8.27 | N | 12.0 |

Example 127

α-(4-Acetylphenoxy)-α'-piperidino p-xylol

Hydroxyacetophenone (2 mmol) and 5 mmol of $K_2CO_3$ were stirred in 20 ml of acetone with 2 ml of DMF for 10 minutes. After addition of 3.5 mmol of α,α'-dibromoxylol the reaction was stirred at ambient temperature for 12 hours and after addition of 7 mmol of piperidine for 1 hour under reflux. The solvent was evaporated under reduced pressure. The residue was suspended in water, extracted with methylene chloride. The combined organic extracts were crystallized with oxalic acid. Recrystallization resulted in the pure product.

| SF: C₂₁H₂₅NO₂ × C₂H₂O₄ (413.5) mp: 136–137° C. | | | | | | | |
|---|---|---|---|---|---|---|---|
| CHN analysis | calculated: | C | 66.8 | H | 6.58 | N | 3.39 |
|  | found: | C | 66.7 | H | 6.70 | N | 3.40 |

Example 128

α-(4-Acetylphenoxy)-α'-(1-pyrrolidinyl)p-xylol

Hydroxyacetophenone (2 mmol) and 5 mmol of K₂CO₃ were stirred in 20 ml of acetone with 2 ml of DMF for 10 minutes. After addition of 3.5 mmol of α,α'-dibromoxylol the reaction was stirred at ambient temperature for 12 hours and after addition of 7 mmol of pyrrolidine for 1 hour under reflux. The solvent was evaporated under reduced pressure. The residue was suspended in water, extracted with methylene chloride. The combined organic extracts were crystallized with oxalic acid. Recrystallization resulted in the pure product.

| SF: C₂₀H₂₃NO₂ × C₂H₂O₄ × 0.25 H₂O (404.0) mp: 136–137° C. | | | | | | | |
|---|---|---|---|---|---|---|---|
| CHN analysis | calculated: | C | 65.4 | H | 6.36 | N | 3.47 |
|  | found: | C | 65.6 | H | 6.29 | N | 3.47 |

Example 129

α-(3-Phenylpropoxy)-α'-piperidino p-xylol 4-(Piperidinomethyl)benzoic acid methyl ester (22 mmol) in dry tetrahydrofurane was added dropwise to a suspension of 44 mmol of lithium aluminium hydride in 30 ml of dry tetrahydrofurane at 0° C. After refluxing for 2 hours a saturated solution of ammonium chloride in water was added dropwise. After stirring for 12 hours at ambient temperature the organic layer was isolated and the aqueous layer extracted with methylene chloride. The organic extracts were combined and the solvent was evaporated under reduced pressure. The residue was crystallized with maleic acid from diethyl ether/2-propanol (Yield: 91%). Sodium 4-(piperidinomethyl)benzyl alcoholate (5 mmol) and 6 mmol of 3-phenylpropyl bromide in 10 ml of dry toluene were refluxed for 6 hours. The solvent was evaporated under reduced pressure. The residue was purified by rotatory chromatography on silica gel using methylene chloride/ammonia atmosphere as eluent. The product was crystallized with oxalic acid from diethyl ether/ethanol.

| SF: C₂₂H₂₉NO × C₂H₂O₄ × 0.5 H₂O (422.5) mp: 104–105° C. | | | | | | | |
|---|---|---|---|---|---|---|---|
| CHN analysis | calculated: | C | 68.2 | H | 7.63 | N | 3.32 |
|  | found: | C | 68.3 | H | 7.26 | N | 3.36 |

Example 130

3-(4-Chlorobenzyl)-5-(2-piperidinoethyl)-1,2,4-oxadiazole

Hydroxylamine hydrochloride (20 mmol) was added dropwise to a solution of 20 mmol of sodium in 50 ml of methanol at 0° C. After stirring for 30 minutes at ambient temperature 10 mmol of 4-chlorobenzyl cyanide was added dropwise at 0° C. After refluxing for 6 hours the suspension was filtered and the solvent evaporated under reduced pressure. The residue was crystallized from diethyl ether (Yield: 41%). To a solution of 4 mmol of the product and 6 mmol of 3-piperidinopropionic acid methyl ester in 15 ml of dry methanol 5 mmol of sodium in 20 ml of methanol was added dropwise at 0° C. After stirring for 1 hour under argon atmosphere followed by refluxing for 18 hours the solvent was evaporated under reduced pressure. The residue was suspended in DMF and stirred for 6 hours at 80° C. The solvent was evaporated under reduced pressure. The residue was suspended in water and extracted with methylene chloride. The residue of the organic layer was purified by rotatory chromatography on silica gel using methylene chloride/ammonia atmosphere as eluent. The product was crystallized with oxalic acid from diethyl ether/ethanol.

| SF: C₁₆H₂₀ClN₃O × C₂H₂O₄ (395.8) mp: 152–154° C. | | | | | | | |
|---|---|---|---|---|---|---|---|
| CHN analysis | calculated: | C | 54.6 | H | 5.60 | N | 10.6 |
|  | found: | C | 54.3 | H | 5.60 | N | 10.5 |

Example 131

2-((2-Piperidinoethyl)amino)benzothiazole

2-Chlorobenzothiazole (10 mmol), 10 mmol of 2-piperidinoethanamine, and 30 mmol of triethylamine in 50 ml of dry ethanol were refluxed for 6 hours. The product was crystallized with hydrochloric acid in 2-propanol and recrystallized in methanol.

| SF: C₁₄H₁₉N₃S × 2 HCl × 0.25 H₂O (338.8) Yield: 95% mp: 225° C. | | | | | | | |
|---|---|---|---|---|---|---|---|
| CHN analysis | calculated: | C | 49.6 | H | 6.40 | N | 12.4 |
|  | found: | C | 49.5 | H | 6.49 | N | 12.3 |

Example 132

5-Piperidinopentylamine

5-Chlorovaleronitrile (10 mmol), 20 mmol of piperidine, 20 mmol of potassium carbonate and a catalytic amount of potassium iodide in 50 ml of ethanol were refluxed for 6 hours. The solvent was removed under reduced pressure, the residue suspended in water and extracted with methylene chloride. The organic layer was purified by column chromatography on silica gel using methylene chloride/methanol/aqueous ammonia (90/10/1) as eluent (Yield: 59%). The product was added dropwise to a suspension of 25 mmol of lithium aluminium hydride in 25 ml of dry tetrahydrofurane at 0° C. After refluxing for 1 hour 10 ml of a saturated solution of sodium/potassium tartrate in water was added dropwise. The residue was filtered off and the filtrate purified by column chromatography on silica gel using methylene chloride/methanol/aqueous ammonia (90/10/1) as eluent. The residue was crystallized with hydrochloric acid from diethyl ether/2-propanol.

| SF: $C_{10}H_{22}N_2 \times 2\ HCl \times 0.5\ H_2O$ (252.2) mp: 187° C. | | | | | | | |
|---|---|---|---|---|---|---|---|
| CHN analysis | calculated: | C | 47.6 | H | 9.99 | N | 11.1 |
|  | found: | C | 47.8 | H | 9.70 | N | 11.0 |

Example 133

5-Nitro-2-(6-piperidinohexyl)pyridine

6-Aminohexanol (15 mmol), 15 mmol of 2-chloro-5-nitropyridine, 5 ml of triethylamine, and a catalytic amount of potassium iodide were refluxed in 30 ml of ethanol for 12 hours. The solvent was evaporated, and the residue was purified by column chromatography on silica gel (eluent: methylene chloride/methanol (95/5), ammonia atmosphere). The solvent was removed under reduced pressure (Yield: 66%). The product (5 mmol) was dissolved in tetrahydrofurane, stirred at 0° C. and 10 mmol of thionyl chloride was added dropwise. After 1 hour at ambient temperature the mixture was warmed to 60° C. for 2 hours. The solvent and the excess of thionyl chloride were evaporated. The oily residue was crystallized with hydrochloric acid from diethyl ether/ethanol (Yield: 95%). The product (5 mmol), 10 mmol of piperidine, 15 mmol of potassium carbonate, and a catalytic amount of potassium iodide were refluxed in 30 ml of ethanol for 12 hours. The solvent was evaporated and the residue purified by column chromatography (eluent: methylene chloride/methanol (95/5), ammonia atmosphere). The solvent was removed under reduced pressure, and the residue was crystallized with oxalic acid from diethyl ether/ethanol.

| SF: $C_{16}H_{26}N_4O_2 \times C_2H_2O_4$ (396.4) mp: 118.6–119.7° C. | | | | | | | |
|---|---|---|---|---|---|---|---|
| CHN analysis | calculated: | C | 54.5 | H | 7.12 | N | 14.1 |
|  | found: | C | 54.4 | H | 7.18 | N | 14.2 |

Example 134

3-Nitro-2-(6-piperidinohexylamino)pyridine

6-Aminohexanol (15 mmol), 15 mmol of 2-chloro-3-nitropyridine, 5 ml of triethylamine and a catalytic amount of potassium iodide were refluxed in 30 ml of ethanol for 12 hours. The solvent was evaporated and the residue was purified by column chromatography on silica gel (eluent: methylene chloride/methanol (98/2), ammonia atmosphere). The solvent was removed under reduced pressure (Yield: 55%). The product (5 mmol) was dissolved in tetrahydrofurane, stirred at 0° C. and 10 mmol of thionyl chloride was added dropwise. After 1 hour at ambient temperature the mixture was warmed to 60° C. for 2 hours. The solvent and the excess of thionyl chloride were evaporated. The oily residue was crystallized with hydrochloric acid from diethyl ether/ethanol (Yield: 95%). The product (5 mmol), 10 mmol of piperidine, 15 mmol of potassium carbonate, and a catalytic amount of potassium iodide were refluxed in 30 ml of ethanol for 12 hours. The solvent was evaporated and the residue purified by column chromatography (eluent: methylene chloride/methanol (95/5), ammonia atmosphere). The solvent was removed under reduced pressure, and the residue was crystallized with oxalic acid from diethyl ether/ethanol

| SF: $C_{16}H_{26}N_4O_2 \times C_2H_2O_4$ (396.4) mp: 130.3–130.7° C. | | | | | | | |
|---|---|---|---|---|---|---|---|
| CHN analysis | calculated: | C | 54.5 | H | 7.12 | N | 14.1 |
|  | found: | C | 54.3 | H | 7.14 | N | 13.9 |

Example 135

2-(6-Piperidinohexylamino)pyrimidine

6-Aminohexanol (15 mmol), 15 mmol of 2-chloropyrimidine, 5 ml of triethylamine, and a catalytic amount of potassium iodide were refluxed in 30 ml of ethanol for 12 hours. The solvent was evaporated, and the residue was purified by column chromatography on silica gel (eluent: methylene chloride/methanol (98/2), ammonia atmosphere). The solvent was removed under reduced pressure (Yield: 40%). The product (5 mmol) was dissolved in tetrahydrofurane, stirred at 0° C. and 10 mmol of thionyl chloride was added dropwise. After 1 hour at ambient temperature the mixture was warmed to 60° C. for 2 hours. The solvent and the excess of thionyl chloride were evaporated. The oily residue was crystallized with hydrochloric acid from diethyl ether/ethanol (Yield: 95%). The product (5 mmol), 10 mmol of piperidine, 15 is mmol of potassium carbonate, and a catalytic amount of potassium iodide were refluxed in 30 ml of ethanol for 12 hours. The solvent was evaporated and the residue purified by column chromatography (eluent: methylene chloride/methanol (95/5), ammonia atmosphere). The solvent was removed under reduced pressure, and the residue was crystallized with oxalic acid from diethyl ether/ethanol.

| SF: $C_{15}H_{26}N_4 \times C_2H_2O_4$ (352.4) mp: 150.3–150.9° C. | | | | | | | |
|---|---|---|---|---|---|---|---|
| CHN analysis | calculated: | C | 57.9 | H | 8.00 | N | 15.9 |
|  | found: | C | 58.0 | H | 8.14 | N | 15.8 |

Example 136

N-(6-Phenylhexyl)piperidine

6-Phenylhexanol (5 mmol) was stirred at 0° C., and thionyl chloride (10 mmol) was added dropwise. After 1 hour at ambient temp. the mixture was warmed to 60° C. for 2 hours. The excess of thionyl chloride was evaporated. The oily residue was purified by column chromatography on silica gel (eluent: methylene chloride) (Yield: 98%). The product was dissolved in 50 ml of ethanol, and 10 mmol of $K_2CO_3$, 1 mmol of Kl, and 10 mmol of piperidine were added. After refluxing for 6 hours the solvent was evaporated under reduced pressure. The residue was suspended in water and extracted with methylene chloride. The organic extracts were combined, dried with $MgSO_4$ and the residue purified by column chromatography on silica gel (eluent: methylene chloride/methanol/aqueous ammonia (90/10/1)). The residue was crystallized with oxalic acid from diethyl ether/methanol.

| SF: $C_{17}H_{27}N \times C_2H_2O_4$ (335.5) mp: 152° C. | | | | | | | |
|---|---|---|---|---|---|---|---|
| CHN analysis | calculated: | C | 68.0 | H | 8.71 | N | 4.18 |
| | found: | C | 68.0 | H | 8.67 | N | 4.05 |

Example 137

α-(4-Acetylphenoxy)-α'-(4-methylpiperidino)p-xylol

α,α'-Dibromo-para-xylene (30 mmol), 4-hydroxyacetophenone (20 mmol), and potassium carbonate (50 mmol) were refluxed in 50 ml of acetone for 12 hours. The solvent was removed under reduced pressure and the residue purified by column chromatography on silica gel (eluent: methylene chloride/petroleum ether/methanol (60/38/2)).

The product (2 mmol), 4-methylpiperidine (6 mmol), potassium carbonate (8 mmol), and catalytic amounts of potassium iodide were refluxed in acetone for 12 hours. The solvent was evaporated. The residue was washed with water and extracted with ethyl acetate. The solvent was removed under reduced pressure. The product was crystallized with oxalic acid from diethyl ether/ethanol.

| SF: $C_{22}H_{27}NO_2 \times C_2H_2O_4 \times 0.75\ H_2O$ (440.7) mp: 145° C. | | | | | | | |
|---|---|---|---|---|---|---|---|
| CHN analysis | calculated: | C | 65.41 | H | 6.92 | N | 3.18 |
| | found: | C | 65.12 | H | 6.69 | N | 3.17 |

Example 138

α-(4-Acetylphenoxy)-α'-(3,5-cis-dimethylpiperidino)p-xylol

Following the procedure described in example 137, the ether obtained (2 mmol), 3,5-dimethylpiperidine (mixture of cis and trans, 8 mmol), potassium carbonate (8 mmol), and catalytic amounts of potassium iodide were refluxed in acetone for 12 hours. After evaporating the solvent the product was purified by column chromatography on silica gel and thereby separated from the corresponding diastereomer (eluent: diethyl ether/petroleum ether/triethylamine (66/33/1)). The product was crystallized with oxalic acid from diethyl ether/ethanol.

| SF: $C_{23}H_{29}NO_2 \times C_2H_2O_4 \times 0.5\ H_2O$ (450.2) mp: 148° C. | | | | | | | |
|---|---|---|---|---|---|---|---|
| CHN analysis | calculated: | C | 66.69 | H | 7.11 | N | 3.11 |
| | found: | C | 66.95 | H | 7.30 | N | 3.20 |

Example 139

α-(4-Acetylphenoxy)-α'-(3,5-trans-dimethylpiperidino)p-xylol

Following the procedure described in example 137, the ether obtained (2 mmol), 3,5-dimethylpiperidine (mixture of cis and trans, 8 mmol), potassium carbonate (8 mmol), and catalytic amounts of potassium iodide were refluxed in acetone for 12 hours. After evaporating the solvent the product was purified by column chromatography on silica gel and thereby separated from the corresponding diastereomer (eluent: diethyl ether/petroleum ether/triethylamine (66/33/1)). The product was crystallized with oxalic acid from diethyl ether/ethanol.

| SF: $C_{23}H_{29}NO_2 \times C_2H_2O_4 \times 0.5\ H_2O$ (450.2) mp: 141° C. | | | | | | | |
|---|---|---|---|---|---|---|---|
| CHN analysis | calculated: | C | 66.69 | H | 7.11 | N | 3.11 |
| | found: | C | 66.94 | H | 7.17 | N | 3.19 |

Example 140

α-(4-Acetylphenoxy)-α'-(2-methylpyrrolidino)p-xylol

Following the procedure described in example 137, the ether obtained (2 mmol), 2-methylpyrrolidine (6 mmol), potassium carbonate (8 mmol) and catalytic amounts of potassium iodide were refluxed in acetone for 12 hours. The solvent was evaporated. The residue was washed with water and extracted with ethyl acetate. The solvent was removed under reduced pressure. The product was crystallized with hydrochloric acid from diethyl ether/ethanol. Recrystallization resulted in the pure product.

| SF: $C_{21}H_{25}NO_2 \times HCl \times 0.25\ H_2O$ (361.1) mp: 324° C. | | | | | | | |
|---|---|---|---|---|---|---|---|
| CHN analysis | calculated: | C | 69.26 | H | 7.00 | N | 3.85 |
| | found: | C | 69.52 | H | 7.12 | N | 3.85 |

Example 141

α-(4-Cyclopropylcarbonylphenoxy)-α'-piperidino-p-xylol

A solution containing 1,4-benzenedimethanol (30 mmol), sodium hydride (25 mmol), catalytic amounts of tetrabutylammonium iodide, and 15-crown-5 (0.5 mmol) in tetrahydrofuran was stirred for 10 minutes. Cyclopropyl-4-fluorophenylketone (20 mmol) was added dropwise, and the solution was refluxed for 24 hours. The solvent was removed under reduced pressure. The residue was purified by column chromatography on silica gel (eluent: methylene chloride/methanol (98/2)).

At 0° C. the product (4 mmol) was added to thionyl chloride (8 mmol). The temperature was raised to 70° C. for three hours. Excess thionyl chloride was evaporated and the residue purified by column chromatography on silica gel (eluent: methylene chloride/methanol (95/5)). The product (2 mmol), piperidine (4 mmol), catalytic amounts of potassium iodide, and potassium carbonate (6 mmol) dissolved in acetone were refluxed for 12 hours. The solvent was evaporated. The crude product was washed with water and extracted with ethyl acetate. The organic layer was removed under reduced pressure. The residue was crystallized with oxalic acid from diethyl ether/ethanol.

| SF: $C_{23}H_{27}NO_2 \times C_2H_2O_4$ (439.2) mp: 194° C. | | | | | | | |
|---|---|---|---|---|---|---|---|
| CHN analysis | calculated: | C | 68.33 | H | 6.61 | N | 3.19 |
| | found: | C | 68.38 | H | 6.78 | N | 3.29 |

Example 142

α-(4-Cyclopropylcarbonylphenoxy)-α'-(4-methylpiperidino)p-xylol

Following the procedure described in example 141, the chloride obtained (2 mmol), 4-methylpiperidine (4 mmol), potassium carbonate (6 mmol), and catalytic amounts of potassium iodide were refluxed in acetone for 12 hours. The solvent was evaporated. The crude product was washed with water and extracted with ethyl acetate. The organic layer was removed under reduced pressure, and the residue was crystallized with oxalic acid from diethyl ether/ethanol.

| SF: $C_{24}H_{29}NO_2 \times C_2H_2O_4 \times 0.75\ H_2O$ (466.7) mp: 169–170° C. | | | | | | | |
|---|---|---|---|---|---|---|---|
| CHN analysis | calculated: | C | 66.91 | H | 6.96 | N | 2.99 |
| | found: | C | 66.85 | H | 6.83 | N | 2.96 |

Example 143

α-(4-Cyclopropylcarbonylphenoxy)-α'-pyrrolidino-p-xylol

Following the procedure described in example 141, the chloride obtained (2 mmol), pyrrolidine (4 mmol), catalytic amounts of potassium iodide, and potassium carbonate (6 mmol) were refluxed in acetone for 12 hours. The solvent was evaporated. The crude product was washed with water and extracted with ethyl acetate. The organic layer was removed under reduced pressure, and the residue was crystallized with oxalic acid from diethyl ether/ethanol.

| SF: $C_{22}H_{25}NO_2 \times C_2H_2O_4 \times 0.5\ H_2O$ (434.2) mp: 179° C. | | | | | | | |
|---|---|---|---|---|---|---|---|
| CHN analysis | calculated: | C | 66.38 | H | 6.45 | N | 3.22 |
| | found: | C | 66.61 | H | 6.45 | N | 3.22 |

Example 144

3-Phenylpropyl 3-(4-methylpiperidino)propylether

3-Phenylpropylmesilate (18 mmol), catalytic amounts of tetrabutylammonium iodide, and 15-crown-5 (0.5 mmol) were added under argon atmosphere to a solution of 1,3-propanediol (25 mmol) and sodium hydride (25 mmol) in tetrahydrofuran which had been stirred over night. The mixture was refluxed for 24 hours. The solvent was evaporated and the oily residue purified by column chromatography (eluent: methylene chloride/methanol (95/5)). At 0° C. the product (8 mmol) was added to thionyl chloride (16 mmol). The temperature was raised to 70° C. for three hours. Excess thionyl chloride was evaporated. The residue was purified by column chromatography on silica gel (eluent: methylene chloride), and the solvent was evaporated under reduced pressure. The chloride obtained (5 mmol), 4-methylpiperidine (10 mmol), potassium carbonate (15 mmol), and catalytic amounts of potassium iodide were dissolved in acetone and refluxed for 12 hours. After evaporating the solvent the product was purified by column chromatography on silica gel (eluent: diethyl ether/petroleum ether/triethylamine (66/33/1)) and crystallized with oxalic acid from diethyl ether/ethanol.

| SF: $C_{18}H_{29}NO \times C_2H_2O_4$ (365.4) mp: 119–120° C. | | | | | | | |
|---|---|---|---|---|---|---|---|
| CHN analysis | calculated: | C | 65.73 | H | 8.55 | N | 3.83 |
| | found: | C | 65.44 | H | 8.83 | N | 3.79 |

Example 145

3-Phenylpropyl 3-(3,5-cis-dimethylpiperidino)propylether

Following the procedure described in example 144 the chloride obtained (5 mmol), 3,5-dimethylpiperidine (mixture of cis and trans, 10 mmol), potassium carbonate (15 mmol), and catalytic amounts of potassium iodide were dissolved in acetone and refluxed for 12 hours. After evaporating the solvent the product was purified by column chromatography on silica gel and thereby separated from the corresponding diastereomer (eluent: diethyl ether/petroleum ether/triethylamine (66/33/1)). The product was crystallized with oxalic acid from diethyl ether/ethanol.

| SF: $C_{19}H_{31}NO \times C_2H_2O_4$ (379.5) mp: 107–108° C. | | | | | | | |
|---|---|---|---|---|---|---|---|
| CHN analysis | calculated: | C | 66.46 | H | 8.76 | N | 3.69 |
| | found: | C | 66.42 | H | 8.54 | N | 3.67 |

Example 146

3-Phenylpropyl 3-(3,5-trans-dimethylpiperidino)propylether

Following the procedure described in example 143 the chloride obtained (5 mmol), 3,5-dimethylpiperidine (mixture of cis and trans, 10 mmol), potassium carbonate (15 mmol), and catalytic amounts of potassium iodide were dissolved in acetone and refluxed for 12 hours. After evaporating the solvent the product was purified by column chromatography on silica gel and thereby separated from the corresponding diastereomer (eluent: diethyl ether/petroleum ether/triethylamine (66/33/1)). The product was crystallized with oxalic acid from diethyl ether/ethanol.

| SF: $C_{19}H_{31}NO \times C_2H_2O_4$ 379.5) mp: 123.5° C. | | | | | | | |
|---|---|---|---|---|---|---|---|
| CHN analysis | calculated: | C | 66.46 | H | 8.76 | N | 3.69 |
| | found: | C | 66.35 | H | 8.72 | N | 3.75 |

Example 147

3-Phenylpropyl 3-(3-methylpiperidino)propylether

Following the procedure described in example 143 the chloride obtained (5 mmol), 3-methylpiperidine (10 mmol), potassium carbonate (15 mmol), and catalytic amounts of potassium iodide were dissolved in acetone and refluxed for 12 hours. After evaporating the solvent the product was purified by column chromatography on silica gel (eluent: diethyl ether/petroleum ether/triethylamine (66/33/1)). The product was crystallized with oxalic acid from diethyl ether/ethanol.

| SF: $C_{18}H_{29}NO \times C_2H_2O_4$ (365.4) mp: 123° C. | | | | | | | |
|---|---|---|---|---|---|---|---|
| CHN analysis | calculated: | C | 65.73 | H | 8.55 | N | 3.83 |
| | found: | C | 65.39 | H | 8.72 | N | 3.79 |

Example 148

3-Phenylpropyl 3-pyrrolidinopropylether

Following the procedure described in example 143 the chloride obtained (5 mmol), pyrrolidine (10 mmol), potassium carbonate (15 mmol), and catalytic amounts of potassium iodide were dissolved in acetone and refluxed for 12 hours. After evaporating the solvent the product was purified by column chromatography on silica gel (eluent: diethyl ether/petroleum ether/triethylamine (66/33/1)). The product was crystallized with oxalic acid from diethyl ether/ethanol.

| SF: $C_{15}H_{25}NO \times C_2H_2O_4$ (337.4) mp: 105.5° C. | | | | | | | |
|---|---|---|---|---|---|---|---|
| CHN analysis | calculated: | C | 64.07 | H | 8.07 | N | 4.15 |
| | found: | C | 63.85 | H | 7.84 | N | 4.13 |

Example 149

3-(4-Chlorophenyl)propyl 3-(4-methylpiperidino)propylether 3-(4-Chlorophenyl)propylmesilate (18 mmol), catalytic amounts of tetrabutylammonium iodide, and 15-crown-5 (0.5 mmol) were added under argon atmosphere to a solution of 1,3-propanediol (25 mmol) and sodium hydride (25 mmol) in tetrahydrofuran which had been stirred over night. The mixture was refluxed for 24 hours. The solvent was evaporated and the oily residue purified by column chromatography (eluent: methylene chloride/methanol (95/5)). At 0° C. the product (8 mmol) was added to thionyl chloride (16 mmol). The temperature was raised to 70° C. for three hours. Excess thionyl chloride was evaporated. The residue was purified by column chromatography on silica gel (eluent: methylene chloride) and the solvent was evaporated under reduced pressure. The chloride obtained (5 mmol), 4-methylpiperidine (10 mmol), potassium carbonate (15 mmol), and catalytic amounts of potassium iodide were dissolved in acetone and refluxed for 12 hours. After evaporating the solvent the product was purified by column chromatography on silica gel (eluent: diethyl ether/petroleum ether/triethylamine (66/33/1)) and crystallized with oxalic acid from diethyl ether/ethanol.

| SF: $C_{18}H_{28}NOCl \times C_2H_2O_4$ (399.9) mp: 116° C. | | | | | | | |
|---|---|---|---|---|---|---|---|
| CHN analysis | calculated: | C | 60.08 | H | 7.56 | N | 3.50 |
| | found: | C | 59.78 | H | 7.33 | N | 3.49 |

Example 150

3-(4-Chlorophenyl)propyl 3-(3,5-cis-dimethylpiperidino)propylether

Following the procedure described in example 149 the chloride obtained (5 mmol), 3,5-dimethylpiperidine (mixture of cis and trans, 10 mmol), potassium carbonate (15 mmol), and catalytic amounts of potassium iodide were dissolved in acetone and refluxed for 12 hours. After evaporating the solvent the product was purified by column chromatography on silica gel and thereby separated from the corresponding diastereomer (eluent: diethyl ether/petroleum ether/triethylamine (66/33/1)). The product was crystallized with oxalic acid from diethyl ether/ethanol.

| SF: $C_{19}H_{30}NOCl \times C_2H_2O_4 \times 0.25\ H_2O$ (418.5) mp: 117.5° C. | | | | | | | |
|---|---|---|---|---|---|---|---|
| CHN analysis | calculated: | C | 66.46 | H | 8.76 | N | 3.69 |
| | found: | C | 66.42 | H | 8.54 | N | 3.67 |

Example 151

3-(4-Chlorophenyl)propyl 3-(3,5-trans-dimethylpiperidino)propylether

Following the procedure described in example 149 the chloride obtained (5 mmol), 3,5-dimethylpiperidine (mixture of cis and trans, 10 mmol), potassium carbonate (15 mmol), and catalytic amounts of potassium iodide were dissolved in acetone and refluxed for 12 hours. After evaporating the solvent the product was purified by column chromatography on silica gel and thereby separated from the corresponding diastereomer (eluent: diethyl ether/petroleum ether/triethylamine (66/33/1)). The product was crystallized with oxalic acid from diethyl ether/ethanol.

| SF: $C_{19}H_{30}NOCl \times C_2H_2O_4$ (413.4) mp: 150° C. | | | | | | | |
|---|---|---|---|---|---|---|---|
| CHN analysis | calculated: | C | 60.93 | H | 7.79 | N | 3.38 |
| | found: | C | 60.95 | H | 7.39 | N | 3.34 |

Example 152

4-(6-Piperidinohexylamino)quinoline

6-Aminohexanol (15 mmol), 4-chloroquinoline (15 mmol), 5 ml of triethylamine and catalytic amounts of potassium iodide were refluxed in ethanol for 12 hours. The solvent was evaporated and the residue was purified by flash chromatography on silica gel (eluent: methylene chloride/methanol (98/2), ammonia atmosphere). The solvent was removed under reduced pressure. At 0° C. the product (5 mmol) was added to thionyl chloride (10 mmol). The temperature was raised to 70° C. for three hours. Excess thionyl chloride was evaporated. The residue was recrystallized from diethyl ether/ethanol. The product (5 mmol), piperidine (10 mmol), potassium carbonate (15 mmol), and catalytic amounts of potassium iodide were refluxed in acetone for 12 hours. The solvent was evaporated and the residue purified by flash chromatography (eluent: ethyl acetate/methanol/triethylamine (95/5/2)). The solvent was removed under reduced pressure. The residue was crystallized with oxalic acid from diethyl ether/ethanol.

| SF: $C_{20}H_{29}N_3 \times 2\ C_2H_2O_4 \times 0.5\ H_2O$ (500.6) mp: 167.3–168.1° C. | | | | | | | |
|---|---|---|---|---|---|---|---|
| CHN analysis | calculated: | C | 57.6 | H | 6.85 | N | 8.39 |
| | found: | C | 57.7 | H | 6.55 | N | 8.42 |

Example 153

2-Methyl 4-(3-piperidinopropylamino)quinoline

Synthesis and purification were performed according to the procedure stated in example 152 using reagents 3-aminopropanol (15 mmol), 4-chloro-2-methylquinoline (15 mmol), 5 ml of triethylamine, and catalytic amounts of potassium iodide in the first step. The final product was purified by flash chromatography (eluent: ethyl acetate/triethylamine (95/5)). The solvent was removed under reduced pressure. The residue was crystallized with oxalic acid from diethyl ether/ethanol.

| SF: $C_{18}H_{25}N_3 \times 2\ C_2H_2O_4$ (463.5) mp: 185.5–186.3° C. | | | | | | | |
|---|---|---|---|---|---|---|---|
| CHN analysis | calculated: | C | 57.0 | H | 6.31 | N | 9.07 |
| | found: | C | 56.9 | H | 6.19 | N | 8.98 |

Example 154

2-Methyl 4-(6-piperidinohexylamino)quinoline

Synthesis and purification were performed according to the procedure stated in example 152 using reagents 6-aminohexanol (15 mmol), 4-chloro-2-methylquinoline (15 mmol), 5 ml of triethylamine, and catalytic amounts of potassium iodide in the first step. The final product was purified by column chromatography (eluent: ethyl acetate/triethylamine (95/5)). The solvent was removed under reduced pressure. The residue was crystallized with oxalic acid from diethyl ether/ethanol.

| SF: $C_{21}H_{31}N_3 \times 2\ C_2H_2O_4 \times 0.75\ H_2O$ (519.1) mp: 193.6–194.0° C. | | | | | | | |
|---|---|---|---|---|---|---|---|
| CHN analysis | calculated: | C | 57.9 | H | 7.09 | N | 8.10 |
| | found: | C | 57.8 | H | 7.08 | N | 7.85 |

Example 155

7-Chloro-4-(3-piperidinopropylamino)quinoline

Synthesis and purification were performed according to the procedure stated in example 152 using reagents 3-aminohexanol (15 mmol), 4,7-dichloroquinoline (15 mmol), 5 ml of triethylamine, and catalytic amounts of potassium iodide in the first step. The final product was purified by column chromatography (eluent: ethyl acetate/triethylamine (90/10)). The solvent was removed under reduced pressure. The residue was crystallized with oxalic acid from diethyl ether/ethanol

| SF: $C_{17}H_{22}ClN_3 \times 2\ C_2H_2O_4$ (483.9) mp: 202.9–204.0° C. | | | | | | | |
|---|---|---|---|---|---|---|---|
| CHN analysis | calculated: | C | 52.1 | H | 5.42 | N | 8.68 |
| | found: | C | 51.9 | H | 5.25 | N | 8.65 |

Example 156

7-Chloro-4-(4-piperidinobutylamino)quinoline

Synthesis and purification were performed according to the procedure stated in example 152 using reagents 3-aminobutanol (15 mmol), 4,7-dichloroquinoline (15 mmol), 5 ml of triethylamine, and catalytic amounts of potassium iodide in the first step. The final product was purified by column chromatography (eluent: ethyl acetate/triethylamine (90/10)). The solvent was removed under reduced pressure. The residue was crystallized with oxalic acid from diethyl ether/ethanol.

| SF: $C_{18}H_{24}ClN_3 \times 2\ C_2H_2O_4 \times 0.5\ H_2O$ (506.9) mp: 162.6–163.5° C. | | | | | | | |
|---|---|---|---|---|---|---|---|
| CHN analysis | calculated: | C | 52.1 | H | 5.76 | N | 8.28 |
| | found: | C | 52.2 | H | 5.64 | N | 8.15 |

Example 157

7-Chloro-4-(8-piperidinooctylamino)quinoline 1,8-Dibromooctane (30 mmol), potassium phthalimide (15 mmol), and catalytic amounts of potassium iodide were refluxed in acetone for 3 days. The solvent was evaporated, and the residue was purified by flash chromatography on silica gel (eluent: methylene chloride/petroleum ether (60/40)). The solvent was removed under reduced pressure. The product (12,5 mmol), piperidine (50 mmol), and catalytic amounts of potassium iodide were refluxed in acetone for 12 hours. Solvent and piperidine were evaporated. The residue was treated with hydrochloric acid (2N), with potassium carbonate solution and was then extracted with methylene chloride. The solvent was removed under reduced pressure, and the residue was refluxed in hydrochloric acid (6N) for 12 hours. The solution was neutralized with potassium carbonate solution and extracted with methylene chloride. The organic layer was evaporated and the product was purified by flash chromatography on silica gel (eluent: methylene chloride/triethylamine/methanol (90/10/2)). The product (5 mmol), 4,7-dichloroquinoline (5 mmol), and catalytic amounts of potassium iodide were melted with 10 g of phenole for 12 hours. The residue was purified by flash chromatography (eluent: ethyl acetate/triethylamine (95/5)). The solvent was removed under reduced pressure. The residue was crystallized with oxalic acid from diethyl ether/ethanol.

SF: $C_{22}H_{32}ClN_3 \times 2\ C_2H_2O_4$ (554.0) mp: 150.7–150.9° C.

| CHN analysis | calculated: | C | 56.4 | H | 6.55 | N | 7.58 |
|---|---|---|---|---|---|---|---|
| | found: | C | 56.2 | H | 6.48 | N | 7.42 |

Example 158

7-Chloro-4-(10-piperidinodecylamino)quinoline

Synthesis and purification were performed according to the procedure described in example 157 using reagents 1,10-dibromodecane (30 mmol), potassium phthalimide (15 mmol), and catalytic amounts of potassium iodide in the first step. The final product was purified by column chromatography (eluent: ethyl acetate/triethylamine 95/5). The solvent was removed under reduced pressure. The residue was crystallized with oxalic acid from diethyl ether/ethanol.

SF: $C_{24}H_{36}ClN_3 \times 2\ C_2H_2O_4$ (582.1) mp: 151.2–151.5° C.

| CHN analysis | calculated: | C | 57.8 | H | 6.93 | N | 7.22 |
|---|---|---|---|---|---|---|---|
| | found: | C | 57.4 | H | 6.81 | N | 7.07 |

Example 159

7-Chloro-4-(12-piperidinododecylamino)quinoline

Synthesis and purification were performed according to the procedure described in example 157 using regents 1,12-dibromododecane (30 mmol), potassium phthalimide (15 mmol), and catalytic amounts of potassium iodide in the first step. The residue was purified by flash chromatography (eluent: ethyl acetate/triethylamine (95/5)). The solvent was removed under reduced pressure. The residue was crystallized with oxalic acid from diethyl ether/ethanol.

SF: $C_{26}H_{40}ClN_3 \times 2\ C_2H_2O_4$ (610.2) mp: 141.6–142.9° C.

| CHN analysis | calculated: | C | 59.1 | H | 7.27 | N | 6.89 |
|---|---|---|---|---|---|---|---|
| | found: | C | 58.7 | H | 7.30 | N | 6.78 |

Example 160

7-Chloro-4-(4-(3-piperidinopropoxy)phenylamino)quinoline

4-Hydroxyaniline (11 mmol), 4,7-dichloroquinoline (10 mmol), 1 ml of 2N hydrochloric acid, and catalytic amounts of potassium iodide were refluxed in acetone for 12 hours. The product was filtered. The product (5 mmol), 3-piperidinopropylchloride hydrochloride (5 mmol), potassium carbonate (15 mmol), and catalytic amounts of potassium iodide were refluxed in acetone for 22 hours. The product was filtered and purified by flash chromatography (eluent: methylene chloride/petroleum ether/triethylamine (95/25/5)). The solvent was removed under reduced pressure. The residue was crystallized with oxalic acid from diethyl ether/ethanol.

SF: $C_{23}H_{26}ClN_{30} \times 2\ C_2H_2O_4 \times 0.25\ H_2O$ (580.5) mp: 189.8–190.3° C.

| CHN analysis | calculated: | C | 55.9 | H | 5.29 | N | 7.23 |
|---|---|---|---|---|---|---|---|
| | found: | C | 55.7 | H | 5.43 | N | 7.14 |

Example 161

7-Chloro-4-(2-(4-(3-piperidinopropoxy)phenyl)ethylamino)quinoline

Tyramine (10 mmol), 4,7-dichloroquinoline, and catalytic amounts of potassium iodide were melted in 10 g of phenol at 150° C. for 12 hours. The residue was crystallized with hydrochloric acid from ethyl acetate/water. The product (5 mmol), 3-piperidinopropylchloride hydrochloride (5 mmol), potassium carbonate (15 mmol), and catalytic amounts of potassium iodide were refluxed in N,N-dimethylformamide for 22 hours. The solvent was evaporated and the residue purified by flash chromatography (eluent: ethyl acetate/petroleum ether/triethylamine (95/50/5)). The solvent was removed under reduced pressure. The residue was crystallized with oxalic acid from diethyl ether/ethanol.

SF: $C_{25}H_{30}ClN_{30} \times 2\ C_2H_2O_4 \times H_2O$ (622.1) mp: 149.8–150.2° C.

| CHN analysis | calculated: | C | 56.0 | H | 5.83 | N | 6.75 |
|---|---|---|---|---|---|---|---|
| | found: | C | 55.7 | H | 5.77 | N | 6.46 |

Example 162

4-(6-Piperidinohexanoyl)phenyl 3-piperidinopropylether

3-Phenoxypropylbromide (10 mmol), piperidine (20 mmol), and catalytic amounts of potassium iodide were refluxed in acetone for 12 hours. The solvent was evaporated. The residue was treated with ethyl acetate. The solvent was removed under reduced pressure, and the product was crystallized with hydrochloric acid from isopropanol/diethyl ether. The product (5 mmol) was added to a solution of 6-bromohexanoylchloride (7.5 mmol) and aluminumtrichloride (22.5 mmol) in 10 ml of nitrobenzol. The mixture was stirred at room temperature for 3 days. Ethyl acetate was added, and the mixture was extracted with hydrochloric acid (6N). The solution was neutralized with potassium carbonate solution and extracted with methylene chloride. The solvent was removed under reduced pressure. The product (2.5 mmol), piperidine (5 mmol), potassium carbonate (7.5 mmol), and catalytic amounts of potassium iodide were refluxed in acetone for 12 hours. The solvent was evaporated, and the residue was purified by flash chromatography (eluent: methylene chloride/petroleum ether/methanol (96/3/3)). The solvent was removed under reduced pressure. The residue was crystallized with oxalic acid from diethyl ether/ethanol.

| SF: $C_{25}H_{40}N_2O_2 \times 2\ C_2H_2O_4$ (580.7) mp: 149.1–149.5° C. | | | | | | | |
|---|---|---|---|---|---|---|---|
| CHN analysis | calculated: | C | 60.0 | H | 7.64 | N | 4.82 |
| | found: | C | 59.9 | H | 7.59 | N | 4.81 |

Example 163

5-Nitro-2-(5-piperidinopentylamino)pyridine

Synthesis and purification were performed according to the procedure stated in example 152 using reagents 5-aminopentanol (15 mmol), 2-chloro-5-nitropyridine (15 mmol), 5 ml of triethylamine, and catalytic amounts of potassium iodide in the first step. The final product was purified by column chromatography (eluent: ethyl acetate/triethylamine (90/10)). The solvent was removed under reduced pressure. The residue was crystallized with oxalic acid from diethyl ether/ethanol.

| SF: $C_{15}H_{24}N_4O_2 \times C_2H_2O_4$ (382.4) mp: 95.7–96.0° C. | | | | | | | |
|---|---|---|---|---|---|---|---|
| CHN analysis | calculated: | C | 53.4 | H | 6.85 | N | 14.65 |
| | found: | C | 53.6 | H | 7.00 | N | 14.55 |

Example 164

3-Nitro-2-(6-piperidinopentylamino)pyridine

Synthesis and purification were performed according to the procedure stated in example 152 using reagents 5-aminopentanol (15 mmol), 2-chloro-3-nitropyridine (15 mmol), 5 ml of triethylamine, and catalytic amounts of potassium iodide in the first step. The final product was purified by column chromatography (eluent: ethyl acetate/triethylamine (95/5), ammonia atmosphere). The solvent was removed under reduced pressure. The residue was crystallized with oxalic acid from diethyl ether/ethanol.

| SF: $C_{15}H_{24}N_4O_2 \times C_2H_2O_4 \times 0.25\ H_2O$ (386.9) mp: 148.5–149.2° C. | | | | | | | |
|---|---|---|---|---|---|---|---|
| CHN analysis | calculated: | C | 52.8 | H | 6.90 | N | 14.48 |
| | found: | C | 52.8 | H | 6.80 | N | 14.51 |

Example 165

5-Amino-2-(6-piperidinopentylamino)pyridine

Synthesis and purification were performed according to the procedure stated in example 152 using reagents 5-aminopentanol (15 mmol), 2-chloro-5-nitropyridine (15 mmol), 5 ml of triethylamine, and catalytic amounts of potassium iodide in the first step. The product was purified by column chromatography on silica gel (eluent: methylene chloride/methanol (95/5), ammonia atmosphere) and dissolved in 20 ml of tetrahydrofuran. 100 mg of palladium/active charcoal (10%) was added, and the mixture was hydrogenated at 1 bar $H_2$ for 12 hours. The solvent was removed under reduced pressure, and the residue was crystallized with oxalic acid from diethyl ether/ethanol.

| SF: $C_{15}H_{26}N_4 \times 2\ C_2H_2O_4$ (442.5) mp: 85.7–87.3° C. | | | | | | | |
|---|---|---|---|---|---|---|---|
| CHN analysis | calculated: | C | 51.6 | H | 6.83 | N | 12.66 |
| | found: | C | 51.4 | H | 6.81 | N | 12.83 |

Example 166

2-(6-Piperidinohexylamino)quinoline

Synthesis and purification were performed according to the procedure stated in example 152 using reagents 6-aminohexanol (15 mmol), 2-chloroquinolin (15 mmol), 5 ml of triethylamine, and catalytic amounts of potassium iodide in the first step. The final product was purified by flash chromatography (eluent: ethyl acetate/triethylamine (95/5)). The solvent was removed under reduced pressure, and the residue was crystallized with oxalic acid from diethyl ether/ethanol.

| SF: $C_{20}H_{29}N_3 \times 2\ C_2H_2O_4 \times 0.75\ H_2O$ (505.1) mp: 90.7–91.5° C. | | | | | | | |
|---|---|---|---|---|---|---|---|
| CHN analysis | calculated: | C | 57.1 | H | 6.88 | N | 8.32 |
| | found: | C | 57.1 | H | 6.54 | N | 8.17 |

Example 167

N-(4-Chlorobenzyl)-N'-cyclohexyl-3-piperidinopropyl isothiourea

Cyclohexylamine (10 mmol) was added dropwise to 4-chlorobenzylisothio-cyanate (10 mmol) dissolved in 20 ml of dry ether. The solution was stirred for 2 hours at room temperature. The precipitated product was filtered off and crystallized from ethyl acetate. 3-Piperidinopropyl chloride hydrochloride (3 mmol), the product (3 mmol), and ca-talytic amounts of potassium iodide were refluxed in ethanol for 6 days. Sub-sequently, ethanol was evaporated, and the residue was purified by column chromato-graphy (eluent: methylene chloride/methanol (95/5)). After evaporation of the solvent the product was crystallized with hydrochloric acid from diethyl ether/ethanol.

| SF: $C_{22}H_{34}ClN_3S \times 2\ HCl \times H_2O$ (499.0) mp: 103.0–107.0° C. | | | | | | | |
|---|---|---|---|---|---|---|---|
| CHN analysis | calculated: | C | 53.0 | H | 7.68 | N | 8.42 |
| | found: | C | 52.6 | H | 7.88 | N | 8.24 |

Example 168

2-(6-Piperidinohexylamino)benzothiazole

Synthesis and purification were performed according to the procedure stated in example 152 using reagents 6-aminohexanol (15 mmol), 2-chlorobenzothiazole (15 mmol), 5 ml of triethylamine, and catalytic amounts of potassium iodide in the first step. The final product was purified by flash chromatography (eluent: methylene chloride/methanol (95/5), ammonia atmosphere). The solvent was removed under reduced pressure, and the residue was crystallized with oxalic acid from diethyl ether/ethanol.

| SF: $C_{18}H_{27}N_3S \times 1.9\ C_2H_2O_4$ (488.6) mp: 98.5–101.8° C. | | | | | | |
|---|---|---|---|---|---|---|
| CHN analysis | calculated: | C | 53.6 | H | 6.35 | N | 8.60 |
| | found: | C | 54.0 | H | 6.43 | N | 8.33 |

Example 169

10-Piperidinodecylamine

The synthesis was performed according to the procedure described in example 157 using reagents 1,10-dibromodecane (30 mmol), potassium phthalimide (15 mmol), and catalytic amounts of potassium iodide in the first step. The product (12.5 mmol), piperidine (50 mmol) and catalytic amounts of potassium iodide were refluxed in acetone for 12 hours. Solvent and piperidine were evaporated. The residue was treated with hydrochloric acid (2N), with potassium carbonate solution and then extracted with methylene chloride. The solvent was removed under reduced pressure, and the residue was refluxed in hydrochloric acid (6N) for 12 hours. The solution was neutralized with potassium carbonate solution and extracted with methylene chloride. The organic layer was evaporated, and the final product purified by flash chromatography (eluent: methylene chloride/triethylamine/methanol (90/10/2)). The solvent was removed under reduced pressure. The residue was crystallized with oxalic acid from diethyl ether/ethanol.

| SF: $C_{15}H_{32}N_2 \times 2\ C_2H_2O_4 \times 0.75\ H_2O$ (434.0) mp: 116.1–117.2° C. | | | | | | |
|---|---|---|---|---|---|---|
| CHN analysis | calculated: | C | 52.6 | H | 8.71 | N | 6.45 |
| | found: | C | 52.5 | H | 8.70 | N | 6.35 |

Example 170

3-Phenylpropyl 3-(N,N-diethylamino)propylether

Following the procedure described in example 144 the chloride obtained (5 mmol), diethylamine (10 mmol), potassium carbonate (15 mmol), and catalytic amounts of potassium iodide were dissolved in acetone and refluxed for 12 hours. After evaporating the solvent the product was purified by column chromatography on silica gel (eluent: diethyl ether/petroleum ether/triethylamine (66/33/1)). The product was crystallized with oxalic acid from diethyl ether/ethanol.

| SF: $C_{16}H_{27}NO \times C_2H_2O_4$ (340.3) mp: 80° C. | | | | | | |
|---|---|---|---|---|---|---|
| CHN analysis | calculated: | C | 63.69 | H | 8.61 | N | 4.13 |
| | found: | C | 63.52 | H | 8.40 | N | 4.06 |

Pharmacological Study

Interaction of compounds with the $H_3$ receptor are evidenced in vitro by the measurement of the release of neosynthesized tritiated histamine from rat cerebral cortex synaptosomes preincubated with tritiated histidine (Garbarg et al., J. Pharmacol. Exp. Ther., 1992, 263: 304–310). The $H_3$ potency of agonists is measured by the inhibition of tritiated histamine release and that of antagonists by the progressive reversal of release inhibition by the selective $H_3$ agonist (R)α-methylhistamine (Arrang et al., Nature, 1987, 327: 117–123).

Interaction of compounds with the $H_3$ receptor are evidenced in vitro on guinea-pig ileum by the procedure described by Ligneau et al., J. Pharmacol. Exp. Ther. 271, 452–459 (1994).

Briefly, longitudinal muscle strips from guinea-pig small intestine were dissected out and incubated in a gassed $O_2/CO_2$ (95%/5%) modified Krebs-Ringer's bicarbonate medium at +37° C. in presence of 1 μM mepyramine to block the $H_1$ receptor. After equilibration, contractile activity under stimulation (rectangular pulses of 15 V, 0,5 msec, 0,1 Hz) was recorded.

Concentration-response curves of the effect of (R)α-Methylhistamine alone or together with the antagonist were established.

The effects of agonists and antagonists were estimated in vivo by the measurement of the tele-methylhistamine level variations in the brain of mice (Garbarg et al., J. Neurochem., 1989, 53: 1724–1730). At various time after p.o. administration of the compounds, the effect of agonists and antagonists are evidenced by the decrease and increase respectively in telemethylhistamine level induced.

The changes are compared to those induced by reference compounds given in high dosage and this allows the calculation of the $ED_{50}$ value for each compound which correspond to the dose responsible for an half maximal effect.

The results are listed here-below or reported in the following tables II and III:

Example 59

1-[3-(4-cyanophenoxy)propyl]piperidine, $ED_{50}$=0.02 mg/kg

Example 74

1-[3-(4-buyrylphenoxy)propyl]piperidine, $ED_{50}$=0.21 mg/kg

Example 76

1-[3-(4-cyclopropanecarbonylphenoxy)propyl]piperidine, $ED_{50}$=0.18 mg/kg

Example 88

1-[3-(4-propionylphenoxy)propyl]-3-methylpiperidine, $ED_{50}$=0.14 mg/kg

Example 101

1-[3-(4-cyclopropane carbonyl phenoxy)propyl]-trans-3,5 dimethylpiperidine, $ED_{50}$=0.17 mg/kg

TABLE II

| Ex No. | X | n | $R^1R^2$ | $R^3$ ($n_3$ = 1) | Ki (nM) | $ED_{50}$ (mg/kg/p.o.) |
|---|---|---|---|---|---|---|
| 18 | O | 5 | —(CH$_2$)$_4$— | p-NO$_2$ | 39 ± 11 | 1.1 |
| 43 | O | 3 | Et, Et | p-CN | 95 ± 28 | 0.50 |
| 46 | O | 3 | Et, Et | p-CH$_3$CO | 20 ± 7 | 0.44 |
| 50 | O | 5 | —(CH$_2$)$_4$— | p-CH$_3$CH(OH) | 28 ± 7 | 1.0 |
| 56 | O | 4 | Et, Et | p-CN | 62 ± 15 | 1.1 |
| 59 | O | 3 | —(CH$_2$)$_5$— | p-CN | 11 ± 2 | 0.20 |
| 60 | O | 3 | —(CH$_2$)$_6$— | p-CN | 8.7 ± 2.1 | 0.64 |
| 63 | O | 3 | Et, Et | p-CH$_3$CH(OH) | 60 ± 18 | 0.45 |
| 64 | O | 3 | Et, Et | p-CH$_3$C=N(OH) | 2.7 ± 0.9 | 0.8 |
| 66 | O | 3 | —(3-Me)—(CH$_2$)$_5$— | p-CH$_3$CO | 3.7 ± 0.5 | 0.3 |
| 68 | O | 3 | —(4-Me)—(CH$_2$)$_5$— | p-CH$_3$CO | 4.6 ± 2.0 | 0.5 |
| 69 | O | 3 | —(CH$_2$)$_5$— | p-C$_2$H$_5$CO | 4.7 ± 0.8 | 0.6 |

TABLE III

| Example No. | H$_3$-receptor antagonist activity pA$_2$ (guinea-pig ileum) |
|---|---|
| 120 | 6.3 |
| 124 | 6.4 |
| 130 | 7.2 |
| 131 | 6.6 |
| 136 | 6.5 |

All the above compounds were find to be H$_3$-antagonists.

Comparative data concerning the activity of imidazole derivatives and of the non-imidazole analogues according to the invention, are reported below in Table IV:

TABLE IV

| Imidazole derivative | Non-imidazole analogue according to the invention |
|---|---|
| Ki = 12 nM<br>$ED_{50}$ = 0.54 mg/kg | ex 59:<br>Ki = 11 nM<br>$ED_{50}$ = 0.20 mg/kg |
| | ex 43:<br>Ki = 95 nM<br>$ED_{50}$ = 0.50 mg/kg |
| | ex 58:<br>Ki = 20 nM |
| | ex 60:<br>Ki = 9 nM |
| | ex 116: |

TABLE IV-continued

| Imidazole derivative | Non-imidazole analogue according to the invention |
|---|---|
| 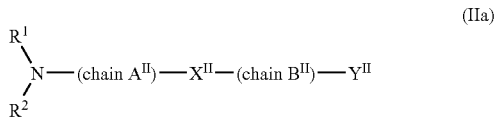 Ki = 17 nM | Ki = 15 nM |

The invention claimed is:

1. A method for treating symptoms associated with cognitive disorders selected from the group consisting of attention, wakefulness and memory disorders, said method comprising administering in an amount effective to inhibit $H_3$ receptor activity to a patient in need thereof a compound having the general formula (IIa)

(IIa)

wherein:
$R^1$ and $R^2$ may be identical or different and represent each independently a lower alkyl
or taken together with the nitrogen atom to which they are attached,
a saturated nitrogen-containing ring

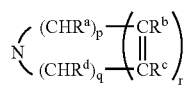
i)

with m ranging from 3 to 6, or
a non-aromatic unsaturated nitrogen-containing ring

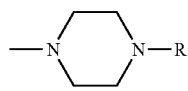
ii)

with p and q being 1 or 2 and r being 1,
$R^{a-d}$ being independently a hydrogen atom or a lower alkyl or carboalkoxy group, or
a morpholino group, or
a N-substituted piperazino group:

—N⟨  ⟩N—R with R being a lower alkyl, cycloalkyl, carboalkoxy, aryl, arylalkyl, an alkanoyl or aroyl group; and
(i) the chain $A^{II}$ selected from a saturated, straight or branched hydrocarbon chain containing 1 to 6 carbon atoms, the saturated hydrocarbon chain optionally may be interrupted by a hetero atom which may be a sulphur atom;
(ii) $X^{II}$ selected from an oxygen atom, —NHCO—, —O—CO—, —OCONH—, —CONH—, and —S—C(=NY$^{II}$)—NH—Y$^{II}$— with the Y$^{II}$ identical or different;
(iii) the chain $B^{II}$ selected from an aryl; a straight alkylene chain —(CH$_2$)$_{nII}$—, $n_{II}$ being an integer which can vary between 1 and 5 or a branched alkylene chain containing from 2 to 8 carbon atoms; and
(iv) $Y^{II}$ selected from a straight or branched alkyl group containing 1 to 8 carbon atoms; a cycloalkyl containing 3 to 6 carbon atoms; an aryl group such as an optionally substituted phenyl group; a 5- or 6-membered heterocyclic radical containing one or two heteroatoms chosen from nitrogen and sulphur atoms, the heterocyclic radical optionally being substituted; and a bicyclic radical resulting from the fusion of a benzene ring to a heterocycle as defined above;

or (i') the chain $A^{II}$ selected from an unbranched or branched alkyl group —(CH$_2$)$_{nIV}$— where $n_{IV}$ is an integer which can vary between 1 and 8;
(ii') the group $X^{II}$ selected from —OCONH—, —OCO—, —OCSNH—, —CH$_2$—, —O—, —OCH$_2$CO—, and saturated alkyl;
(iii') the chain $B^{II}$ selected from an unbranched, branched or unsaturated lower alkyl comprising from 1 to 8 carbon atoms; —(CH$_2$)$_{nII}$ (hetero atom)— where the hetero atom is preferably a sulphur or oxygen atom; nil being an integer which can vary between 1 and 5; and
(iv') the group $Y^{II}$ represents a phenyl group, unsubstituted or mono- or polysubstituted with one or more identical or different substituents selected from halogen atoms, CHO, SO$_2$N(alkyl)$_2$ such as SO$_2$N(CH$_3$)$_2$, NO$_2$, an unbranched or branched alkene, —O(alkyl), —O(aryl), a ketone, an aldehyde, an alcohol, a lower alkyl, —CH=CH—CHO, —C(alkyl)=N—OH, —C(alkyl)=N—O(alkyl) and other keto derivatives, —CH=NOH, —CH=NO(alkyl), and other aldehyde derivatives, an O-phenyl or —OCH$_2$(phenyl) group, —C(cycloalkyl)=NOH, —C(cycloalkyl)=N—O(alkyl); an optionally substituted heterocycle; a cycloalkyl; a phenyl ring fused to a heterocycle comprising a nitrogen hetero atom or to a carbocycle or a heterocycle bearing a keto function; an unbranched or branched lower alkyl comprising from 1 to 8 carbon atoms; a linear or branched alkyl mono- or polysubstituted with phenyl groups which are either unsubstituted or mono- or polysubstituted; a phenyl alkyl ketone in which the alkyl group is branched or unbranched or cyclic; a substituted or unsubstituted benzophenone; a substituted or unsubstituted, unbranched or branched or cyclic phenyl alcohol; an unbranched or branched alkene; a piperidyl group; a polycyclic group, in particular a fluorenyl group, a naphthyl or polyhydronaphthyl group or an indanyl group; a ketone or keto derivative; a diphenyl group; a phenoxyphenyl group; or its pharmaceutically acceptable salts, hydrates, or hydrated salts, or their optical isomers, racemates, diastereoisomers or enantiomers.

2. The method according to claim 1, wherein $R^1$ and $R^2$ are independently a lower alkyl group.

3. The method according to claim 2, wherein $R^1$ and $R^2$ are each an ethyl group.

4. The method according to claim 1, wherein —$NR^1R^2$ is a saturated nitrogen-containing ring:

i)

m being as defined in claim 1.

5. The method according to claim 4, wherein m is 4, 5 or 6.

6. The method according to claim 5, wherein —$NR^1R^2$ is a piperidyl group.

7. The method according to claim 5, wherein —$NR^1R^2$ is a pyrrolidinyl group.

8. The method according to claim 1, wherein —$NR^1R^2$ is a non-aromatic unsaturated nitrogen-containing ring:

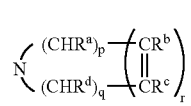

ii)

$R^{a-d}$ and p, q and r being defined in claim 1.

9. The method according to claim 8, wherein p is 2 and q and r are 1.

10. The method according to claim 4, wherein $R^{a-d}$ are each a hydrogen atom.

11. The method according to claim 5, wherein $R^{a-d}$ are each a hydrogen atom.

12. The method according to claim 6, wherein $R^{a-d}$ are each a hydrogen atom.

13. The method according to claim 7, wherein $R^{a-d}$ are each a hydrogen atom.

14. The method according to claim 8, wherein $R^{a-d}$ are each a hydrogen atom.

15. The method according to claim 8, wherein $R^{a-d}$ are each a hydrogen atom.

16. The method according to claim 4, wherein the nitrogen-containing ring i) or ii) is one of mono- and di-substituted.

17. The method according to claim 16, wherein the nitrogen-containing ring i) or ii) is monosubstituted with an alkyl group.

18. The method according to claim 16, wherein the nitrogen-containing ring is mono-substituted with a methyl group.

19. The method according to claim 16, wherein the substituent(s) is(are) in beta-position with respect to the nitrogen atom.

20. The method according to claim 1, wherein —$NR^1R^2$ is a morpholino group.

21. The method according to claim 1, wherein —$NR^1R^2$ is a N-substituted piperazino group.

22. The method according to claim 21, when the piperazino group is N-acetylpiperazino.

23. The method according to claim 1, wherein $X^{II}$ is selected from —O—, —NH—, —$CH_2$—, —OCONH—, —NHCO—, and —NHCONH—.

24. The method according to claim 23, wherein $X^{II}$ is —O—.

25. The method according to claim 1, wherein $Y^{II}$ is selected from a linear or branched alkyl group; a cycloalkyl group which may be selected from a particular cyclopentyl and cyclohexyl group; a phenyl group unsubstituted or mono-substituted; a heterocyclic radical; and a bicyclic radical.

26. The method according to claim 25, wherein $Y^{II}$ comprises a phenyl group unsubstituted or mono-substituted.

27. The method according to claim 1, wherein $Y^{II}$ represents a phenyl group at least mono-substituted with a keto-substituent which may include a linear or branched chain aliphatic ketone comprising from 1 to 8 carbon atoms and optionally bearing a hydroxyl group, a cycloalkylketone, an aryl alkyl ketone or arylalkenylketone in which the aryl group is optionally substituted, or a heteroaryl ketone.

28. The method according to claim 1, wherein $Y^{II}$ is a phenyl group at least mono-substituted with —CHO, a ketone, an aldehyde, —CH=CH—CHO, —C(alkyl)=N—OH, —C(alkyl)=N—O(alkyl) and other keto derivatives, —CH=N—OH, —CH=NO(alkyl) and other aldehyde derivatives, —C(cycloalkyl)=NOH, —C(cycloalkyl)=N—O(alkyl).

29. The method according to claim 1, wherein chain $A^{II}$ is a chain —$(CH_2)_{nIV}$— with $n_{IV}$ varying from 1 to 6.

30. The method according to claim 29, wherein the chain $A^{II}$ is —$(CH_2)$—.

31. The method according to claim 1, wherein the chain $B^{II}$ is —$(CH_2)_2$— or —$(CH_2)_3$—.

32. The method according to claim 1, wherein X is an oxygen atom, the chain $A^{II}$ and chain $B^{II}$ are both —$(CH_2)_3$—.

33. The method according to claim 1, wherein the compound is selected from:
3,3-Dimethylbutyl 3-piperidinopropylether
3-Phenylpropyl 3-piperidinopropylether
3-(4-Chlorophenyl)propyl 3-piperidinopropylether
2-Benzothiazolyl 3-piperidinopropylether
3-Phenylpropyl 3-(4-methylpiperidino)propylether
3-Phenylpropyl 3-(3,5-cis-dimethylpiperidino)propylether
3-Phenylpropyl 3-(3,5-trans-dimethylpiperidino)propylether
3-Phenylpropyl 3-(3-methylpiperidino)propylether
3-Phenylpropyl 3-pyrrolidinopropylether
3-(4-Chlorophenyl)propyl 3-(4-methylpiperidino)propylether
3-(4-Chlorophenyl)propyl 3-(3,5-cis-dimethylpiperidino)propylether
3-(4-Chlorophenyl)propyl 3-(3,5-trans-dimethylpiperidino)propylether
3-Phenylpropyl 3-(N,N-diethylamino)propylether
N-Phenyl-3-piperidinopropyl carbamate
N-Pentyl-3-piperidinopropyl carbamate
(S)-(+)-N-[2-(3,3-Dimethyl)butyl]-3-piperidinopropyl carbamate 3-Cyclopentyl-N-(3-(1-pyrrolidinyl)propyl)propanamide
N-Cyclohexyl-N'-(1-pyrrolidinyl-3-propyl)urea
2-((2-Piperidinoethyl)amino)benzothiazole
5-Piperidinopentylamine
2-Nitro-5-(6-piperidinohexyl)pyridine
3-Nitro-2-(6-piperidinohexylamino)pyridine
2-(6-Piperidinohexylamino)pyrimidine
N-6-Phenylhexyl)piperidine
N-phenyl-N'-(diethylamino-3-propyl)urea
N-benzyl-N'-(3-piperidinopropyl)guanidine
N-(3-(N,N-Diethylamino)propyl)N'-phenylurea
N-Cyclohexylmethyl-N'-(3-piperidinopropyl)guanidine,
or its pharmaceutically acceptable salts, hydrates, or hydrated salts, or the polymorphic crystalline structures of these compounds or their optical isomers, racemates, diastereomers or enantiomers.

34. The method of treatment according to claim 1 wherein the heterocycle comprises a sulphur hetero atom.

35. The method of treatment according to claim 1, wherein the symptoms occur in an aged person.

36. The method according to claim 1 wherein said compound is 3-(4-chlorophenyl)propyl-3-piperidinopropylether or its pharmaceutically acceptable salts, hydrates, or hydrated salts, or the polymorphic crystalline structures of these compounds or their optical isomers, racemates, diastereoisomers or enantiomers.

37. The method according to claim 1 wherein said compound is in the form of a pharmaceutically acceptable salt chosen from the group consisting in hydrochloride, hydrobromide, hydrogen maleate, hydrogen oxalate.

38. The method according to claim 1 wherein the symptoms associated with cognitive disorders are attention, wakefulness or memory disorders associated with Alzheimer's disease.

* * * * *

UNITED STATES PATENT AND TRADEMARK OFFICE
CERTIFICATE OF CORRECTION

| | | |
|---|---|---|
| PATENT NO. | : 7,138,413 B1 | Page 1 of 1 |
| APPLICATION NO. | : 09/622199 | |
| DATED | : November 21, 2006 | |
| INVENTOR(S) | : Schwartz et al. | |

It is certified that error appears in the above-identified patent and that said Letters Patent is hereby corrected as shown below:

On the first (cover/description) page, Section (75) should be corrected to include the corrected names of the Inventors as follows:

-- (75) Inventors: --    Jean-Charles Schwartz, Paris (FR);
　　　　　　　　　　　　 Monique Garbarg, Paris (FR);
　　　　　　　　　　　　 Jeanne-Marie Lecomte, Paris (FR);
　　　　　　　　　　　　 Xavier Ligneau, Paris (FR);
　　　　　　　　　　　　 Walter G. Schunack, Berlin (DE);
　　　　　　　　　　　　 Holger Stark, Berlin (DE);
　　　　　　　　　　　　 Charon Robin Ganellin, Welwyn (GB);
　　　　　　　　　　　　 Fabien Leurquin, London (GB);
　　　　　　　　　　　　 Sigurd Elz, Berlin (DE);
　　　　　　　　　　　　 Jean-Michel Arrang, Dourdan (FR) --

Signed and Sealed this

Third Day of July, 2007

JON W. DUDAS
*Director of the United States Patent and Trademark Office*